United States Patent
Reed et al.

(10) Patent No.: US 12,421,554 B2
(45) Date of Patent: *Sep. 23, 2025

(54) METHOD FOR THE ISOLATION OF DOUBLE-STRAND BREAKS

(71) Applicant: University College Cardiff Consultants Limited, Cardiff (GB)

(72) Inventors: Simon Reed, Cowbridge (GB); Felix Dobbs, Cambridge (GB); Patrick Van Eijk, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/620,644

(22) Filed: Mar. 28, 2024

(65) Prior Publication Data

US 2024/0309455 A1 Sep. 19, 2024

Related U.S. Application Data

(63) Continuation of application No. 18/042,193, filed as application No. PCT/EP2021/073203 on Aug. 20, 2021.

(30) Foreign Application Priority Data

Aug. 21, 2020 (GB) .................................... 2013141

(51) Int. Cl.
C12Q 1/6806 (2018.01)
C12Q 1/6874 (2018.01)
C12Q 1/6883 (2018.01)

(52) U.S. Cl.
CPC ......... *C12Q 1/6883* (2013.01); *C12Q 1/6806* (2013.01); *C12Q 1/6874* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,951,781 B2 | 2/2015 | Reed et al. | |
| 9,493,827 B2 | 11/2016 | Von Kalle et al. | |
| 9,518,293 B2 | 12/2016 | Alt et al. | |
| 10,329,574 B2 | 6/2019 | Deschamps et al. | |
| 10,640,820 B2 | 5/2020 | Alt et al. | |
| 10,689,691 B2 | 6/2020 | Zhang et al. | |
| 2010/0111768 A1 | 5/2010 | Banerjee et al. | |
| 2020/0115707 A1 | 4/2020 | Chen et al. | |
| 2020/0248229 A1 | 8/2020 | Zhang et al. | |
| 2020/0392473 A1 | 12/2020 | Zhang et al. | |
| 2021/0062248 A1 | 3/2021 | Bao et al. | |
| 2021/0147909 A1 | 5/2021 | Deschamps et al. | |
| 2022/0025365 A1 | 1/2022 | McNeill et al. | |
| 2024/0011095 A1 | 1/2024 | Reed et al. | |
| 2024/0309454 A1 | 9/2024 | Reed et al. | |

FOREIGN PATENT DOCUMENTS

| | | | |
|---|---|---|---|
| WO | WO-2010053587 A2 * | 5/2010 | ......... C12N 15/1072 |
| WO | WO-2014142841 A1 | 9/2014 | |
| WO | WO-2015134552 A1 | 9/2015 | |
| WO | WO-2015200378 A1 | 12/2015 | |
| WO | WO-2016138080 A1 | 9/2016 | |
| WO | WO-2017044843 A1 | 3/2017 | |
| WO | WO-2017083562 A1 | 5/2017 | |
| WO | WO-2017139672 A1 | 8/2017 | |
| WO | WO-2017218979 A1 | 12/2017 | |
| WO | WO-2018140695 A1 | 8/2018 | |
| WO | WO-2019217816 A1 | 11/2019 | |
| WO | WO-2022038291 A1 | 2/2022 | |

OTHER PUBLICATIONS

Cameron P, et al., "Mapping the genomic landscape of CRISPR-Cas9 cleavage", Nature methods, Jun. 2017, vol. 14 No. 6, pp. 600-606.

Dobbs et al., "Precision digital mapping of endogenous and induced genomic DNA breaks by Induce-seq", Nat Commun. Jul. 9, 2022; 13(1): 3989, 11 pages.

European Search Report for Application No. EP24165314 mailed Apr. 29, 2024, 9 pages.

International Preliminary Report on Patentability and Written Opinion dated Feb. 16, 2023 for International Patent Application No. PCT/EP2021/073203, 7 pages.

International Search Report and Written Opinion dated Oct. 31, 2021 for International Patent Application No. PCT/EP2021/073203, 5 pages.

Kozarewa I, et al., "Amplification-free Illumina sequencing-library preparation facilitates improved mapping and assembly of (G+C)-biased genomes", Nature methods, Apr. 2009, vol. 6 No. 4, pp. 291-295.

Kuzin A, et al., "RGEN-seq for highly sensitive amplification-free screen of off-target sites of gene editors", Scientific Reports, Dec. 2021, vol. 11 No. 1, pp. 1-9.

Office Action for European Application No. EP217664556 mailed Jun. 15, 2023, 4 pages.

Sriramachandran et al., "Genome-wide Nucleotide-Resolution Mapping of DNA Replication Patterns, Single-Strand Breaks, and Lesions by GLOE-Seq", Mol Cell. Jun. 4, 2020; 78(5): 975-985.e7, 19 pages.

(Continued)

*Primary Examiner* — Kimberly Chong
*Assistant Examiner* — Douglas Charles Ryan
(74) *Attorney, Agent, or Firm* — COOLEY LLP

(57) ABSTRACT

The invention relates to a method for determining the number and nature of DNA double-strand breaks (DSBs) in a nucleic acid sample, ideally gDNA; a kit of parts for performing the method including at least a plurality of oligonucleotides for ligating to the nucleic acid sample and providing at least a first hybridization site (RD1 SP or RD2 SP) to which at least one read sequencing primer can hybridise; and oligonucleotides for use in the kit and method.

20 Claims, 28 Drawing Sheets

Specification includes a Sequence Listing.

(56) References Cited

OTHER PUBLICATIONS

"Third Party Submission" submitted in EP application No. 4200443 on Dec. 15, 2023, 11 pages.
Yan et al., "Bliss is a versatile and quantitative method for genome-wide profiling of DNA double-strand breaks", Nat Commun. May 12, 2017; 8:15058, 9 pages.
Declaration of Dr. Alexei Slesarev and Exhibits dated Jan. 8, 2025, 26 pages.
Notice of Opposition for European Application No. 21766455.6 mailed Jan. 9, 2025, 10 pages.
Illumina, Data Processing of Nextera Mate Pair Reads on Illumina Sequencing Platforms, Illumina Technical Note, commercial publication, published 2012, 5 pages.
Non-Final Office Action for U.S. Appl. No. 18/620,640 mailed Dec. 31, 2024, 35 pages.

* cited by examiner

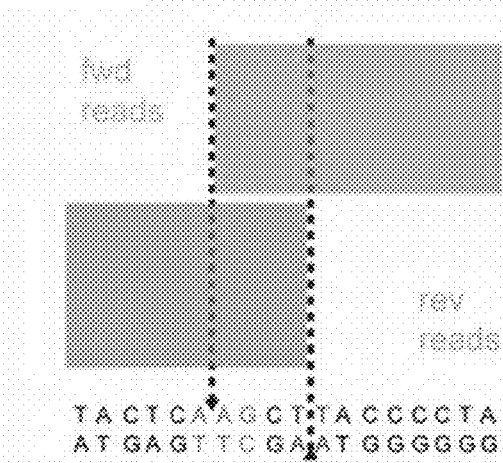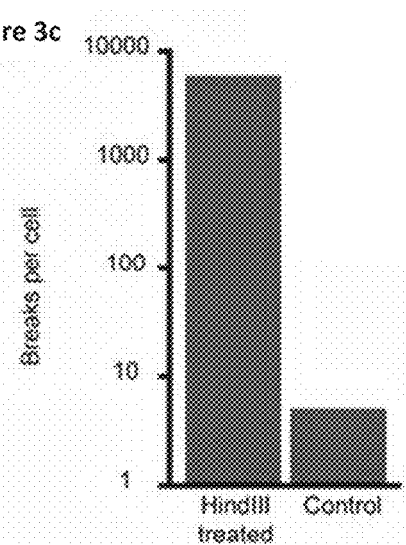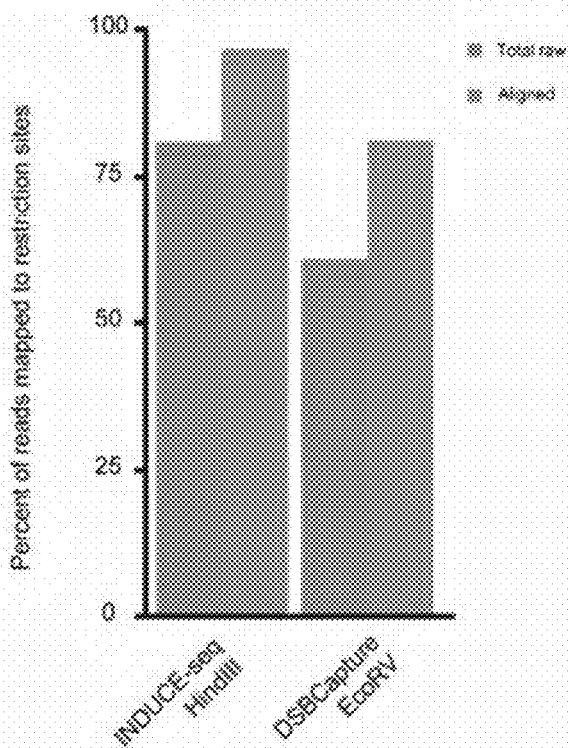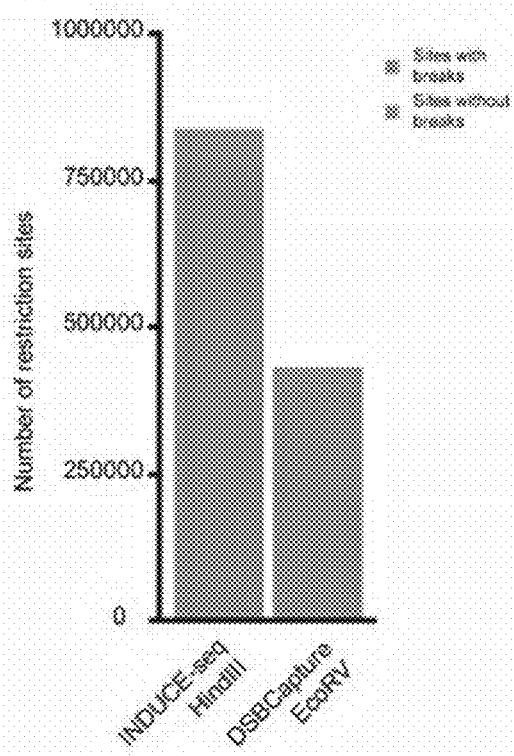

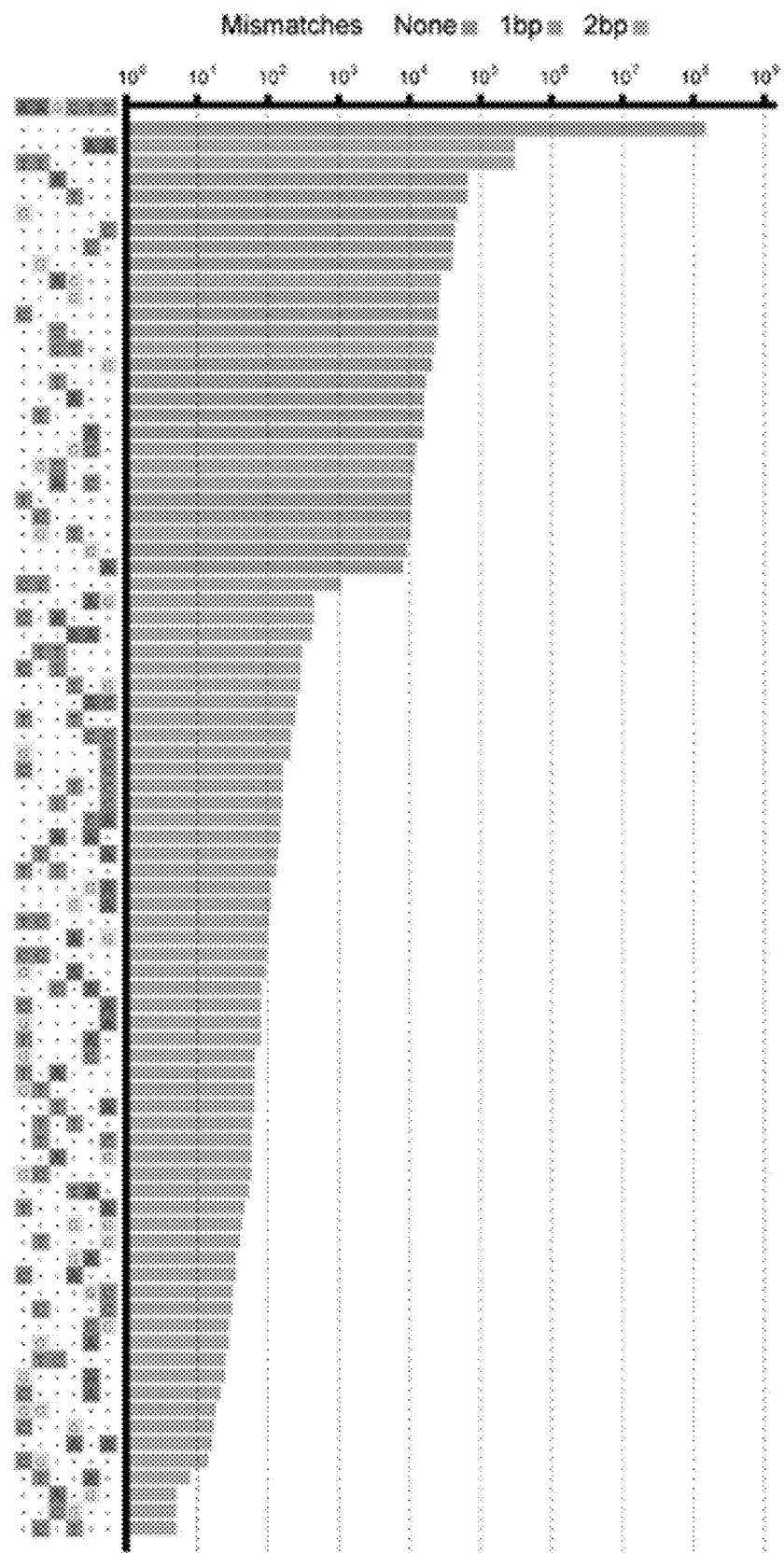
Figure 3f  Number of breaks detected at each restriction site

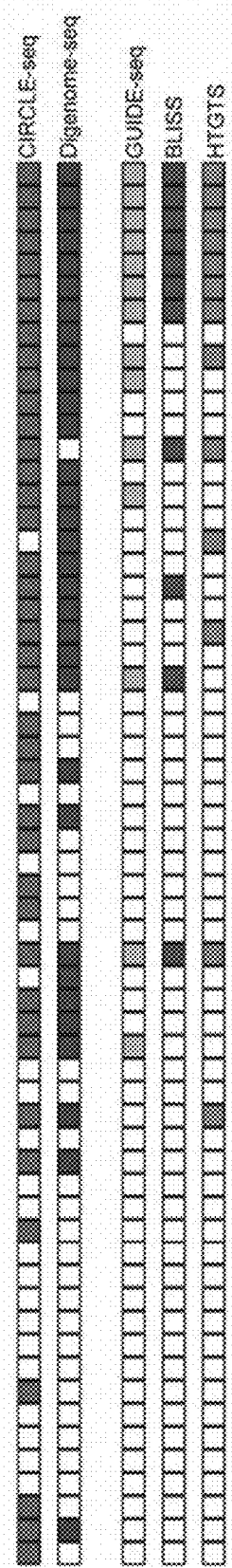

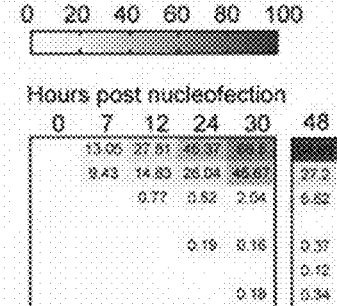

INDUCE-seq Torrent adapters

Primer 1 — Ion Xpress™ Barcode 1 (5'-3' orientation for barcode in bold underlined) inc T tail 5' CCATCTCATCCCTGCGTGTCTCCGAC (SEQ ID NO: 106)
3' /3SpC3/ GGTAGAGTAGGGACGCACAGAGGCTGAGTCGATGATTCCATTGCTA-P A-NNNNNNNNNNNNNNNNNNNN-P 5' (SEQ ID NO: 108)
                                                                                 ^ DSB position
(top strand ending) ...GACTCACCTAAGGTAACGAT*T P-NNNNNNNNNNNNNNNNNNNN-A 3' (SEQ ID NO: 107)

Primer 2
Same as ISP graft

Half-functional Ion P1 Adapter (inc T tail)

Missing sequence

P-ATCACCGACTGCCCATAGAGA/3SpC3/                    3' (SEQ ID NO: 109)
T*TAGTGGCTGACGGGTATCTCTXXXXXXXXXXXXXXXXXXXXCAA   5' (SEQ ID NO: 110)
                        XXXXXXXXXXXXXXXXXXXXGAA     (SEQ ID NO: 111)

Figure 15

METHOD FOR THE ISOLATION OF DOUBLE-STRAND BREAKS

CROSS REFERENCE

This application is a continuation application of Ser. No. 18/042,193, filed Feb. 17, 2023, which is a U.S. National Phase of International Application No. PCT/EP2021/073203, filed Aug. 20, 2021, which claims the benefit of priority to GB. Application No. 2013141.3, filed on Aug. 21, 2020, the entire contents of each of which are hereby incorporated by reference in their entirety.

REFERENCE TO AN ELECTRONIC SEQUENCE LISTING

The contents of the electronic sequence listing (BRSB_001_C02US_SeqList_ST26.xml; Size: 144,117 bytes; and Date of Creation: Dec. 4, 2023) are herein incorporated by reference in its entirety

FIELD OF THE INVENTION

The invention relates to a method for determining the number and nature of DNA double-strand breaks (DSBs) in a nucleic acid sample, ideally genomic DNA (gDNA); a kit of parts for performing the aforesaid method including at least a plurality of oligonucleotides for ligating to said nucleic acid sample; and oligonucleotides for use in said kit and said method.

BACKGROUND OF THE INVENTION

Breaks in nucleic acids, wherein the nucleic acid backbone strand(s) are severed, are particularly hazardous to cells and organisms because they can lead to genome rearrangements. Included amongst such breaks are double-strand breaks (DSBs), typically in DNA, which are the most dangerous of all DNA lesions, as they directly compromise the stability of the genome if left unrepaired. Other than causing cell death and failure to faithfully repair, DSBs can lead to carcinogenesis via the formation of structural genomic alterations, which include deletions, insertions, DNA translocations, and mitotic recombination events in somatic cells. In healthy cells, it is estimated that up to 50 endogenous DSBs are formed per cell during the cell cycle. These low-level physiological breaks either arise sporadically as a result of normal cellular processes such as DNA replication, transcription, and chromatin looping, or occur at higher levels due to recurrent break formation programmed by the cell to facilitate processes such as V (D) J recombination during meiosis. V (D) J recombination is a defining feature of the adaptive immune system. It is a unique mechanism of genetic recombination that occurs in developing lymphocytes during the early stages of B and T cell maturation. It involves somatic recombination, and results in a highly diverse repertoire of antibodies/immunoglobulins and T cell receptors (TCRs) found in B cells and T cells, respectively.

In addition to DSBs acquired through normal cellular processes, a variety of exogenous physical and chemical agents, such as ionising radiation, chemotherapeutic drugs and more recently, CRISPR genome editing technologies, are also potent inducers of strand breaks, particularly genomic DSBs.

Understanding the processes that generate breaks in nucleic acids, particularly the genome, and the mechanisms that repair them is of central importance to genomic medicine. From determining the causes and cures for cancer, through to the safe development of genome editing techniques, the precise and accurate measurement of the frequency, position and cause of DNA double strand breaks in the genome is paramount. However, measuring the genome-wide landscape of endogenous and exogenous/induced DSBs simultaneously in cells is challenging, primarily because of the extremely broad range of rare sporadic breakage events, versus frequently induced recurrent ones.

The emergence of next generation sequencing (NGS) has prompted the development of numerous methods to detect and measure the DNA sequences associated with nucleic acid strand breaks, specifically DSBs, on a genomic scale. These methods fall broadly into three categories:
  i) indirect break labelling using proteins as a proxy for breaks (e.g γH2AX ChIP-seq, DISCOVER-seq);
  ii) indirect labelling of repaired breaks (e.g. GUIDE-seq, HTGTS), and
  iii) direct labelling of unrepaired break-ends in cells (e.g. BLESS, DSBCapture, END-seq, BLISS).

Despite the many technical incremental improvements made in each iteration of these methods, all of them suffer from a common fundamental drawback; a dependence on the standard DNA library preparation required for NGS, following the labelling and enrichment of DSB's in a sample by PCR prior to sequencing. The PCR amplification stage of the process introduces significant bias in the DNA sequencing libraries resulting in an indirect and distorted representation of the original pattern of DSBs present in the sample. This is an acknowledged phenomenon that makes quantification of the original DSB composition in the sample impossible to determine. For many NGS applications, such as whole genome/exome sequencing, this may not represent a significant problem. But for the quantitative, genome-wide measurement of specific features, such as DSBs, PCR-amplification bias introduces high levels of noise into a system where the signals (DSBs) are already very low.

To overcome this disadvantage, we have designed a novel DNA library preparation protocol that avoids the need for break sequence amplification by PCR before DSBs are detected, and, moreover, enhances the DSB signal. By improving the signal to noise ratio for DSB detection, we obtain a direct measurement of genomic breaks in the sample, where one sequence read is equivalent to one break, ideally a DSB, present in the sample.

SUMMARY OF THE INVENTION

Herein, we describe our novel method, termed INDUCE-seq, for the direct measurement of nucleic acid breaks (typically DSBs) further, we demonstrate its ability to identify patterns of breaks that can characterise breaks formed by a variety of different physiological and also induced causes.

INDUCE-seq can thus detect, simultaneously, the presence of low-level sporadic double strand breaks caused by physiological transcription and DNA replication, and higher-level recurrent breaks induced by restriction enzymes or genome editing nucleases such as CRISPR-Cas9. INDUCE-seq can therefore be used to determine the origins of DNA break formation and its mechanism of repair, as well as for the safe development of genome-editing.

In an aspect of the invention, there is provided a method for identifying DNA double-strand breaks (DSBs) in a nucleic acid sample comprising
  i) exposing a sample of nucleic acid suspected of containing DSBs, under ligation conditions, to a first pair of oligonucleotides a first one of which comprises a 5' binding feature that enables ligation of said oligonucleotide to a first strand of said DSB, a hybridization site (RD1 SP) to which a first sequencing primer can bind and a binding sequence for separating said DSB from a pool of DSBs; and a second oligonucleotide that is complementary to said first oligonucleotide of the first pair and comprises a 3' binding feature that enables ligation of said oligonucleotide to a second strand of said DSBs; wherein either or both of said oligonucleotides comprise, a 3' and/or 5' protective feature;

ii) fragmenting the nucleic acid of said sample into fragments;

iii) exposing said fragments, under ligation conditions, to a second pair of oligonucleotides a first one of which comprises a 5' binding feature, that enables ligation of said oligonucleotide to a first strand of said fragmented nucleic acid and a hybridization site (RD2 SP) to which a second sequencing primer can bind; and a second longer oligonucleotide that is in part complementary to said first oligonucleotide of the second pair and comprises a 3' binding feature for binding to a second strand of said fragmented nucleic acid, a sequence complimentary to said hybridization site, and a further sequence that is, optionally, a binding sequence for enabling bridge amplification; and wherein either or both of said oligonucleotides comprise a 3' and/or 5' protective feature;

iv) denaturing the fragments to provide single strand nucleic acids;

v) separating the strands of part iv) into two groups: group A those fragments that have ligated at a first end the first hybridization site and binding sequence provided by the oligonucleotide of part i) and at another end the second hybridization site and further sequence provided by the oligonucleotide of part iii) and group B those fragments that do not have ligated at a first end the hybridization site and binding sequence provided by the oligonucleotide of part i) and at another end the second hybridization site and further sequence provided by the oligonucleotide of part iii); and vi) sequencing the strands of group A using primers that bind to the first and/or second hydridization sites where each sequence is equivalent to a DSB break and further wherein the number and nature of base pair deletions can be determined by comparing each sequence with a genome representative of said species from which the sample was taken.

The oligonucleotide of the second pair that comprises a 5' binding feature may not comprise a binding sequence for separating said fragmented nucleic acid.

The oligonucleotides of part i) and part iii) may be interchanged whereby, after fragmenting in step ii), the nucleic acid is first exposed to the oligonucleotides of part iii) and the nucleic acid is then exposed to the oligonucleotides of part i).

The nucleic acid sample may be gDNA.

The 5' and/or 3' binding feature may comprise one of the following: a phosphate group; a triphosphate 'T-tail', preferably a deoxythymidine triphosphate 'T-tail'; a triphosphate 'A-tail', preferably a deoxyadenosine triphosphate 'A-tail'; at least one random N nucleotide, and a plurality of N nucleotides. The 5' and/or 3' protective feature may comprise a feature that provides resistance to any one or more of the following: phosphorylation activity, phosphatase activity, terminal transferase activity, nucleic acid hybridization, endonuclease activity, exonuclease activity, ligase activity, polymerase activity, and protein binding. The protective features may comprise a phosphorothioate linkage, a dideoxynucleotide or a covalent block, a phosphoramidite, a C3 Spacer phosphoramidite (3SpC3).

The 5' binding feature of said first oligonucleotide of part i) may be a phosphate group and said 3' binding feature of said second oligonucleotide of part i) may be a triphosphate tail. The first and second oligonucleotides of part i) may also comprise an index feature that is a particular sequence of nucleotides that enables the origin of pooled samples to be determined.

The first oligonucleotide of part i), reading 5' to 3', may comprise a 5' binding feature and then, optionally, a protective feature, a hybridization site (RD1 SP) to which a sequencing primer can bind, an index sequence, a binding sequence for separating said DSB from a pool of DSBs, and a 3' binding and/or protective feature. The binding feature may be a phosphate group. The second oligonucleotide of part i), reading 3' to 5', may comprise a 3' binding feature and then, optionally, a protective feature, a hybridization sequence (RD1 SP) to which a sequencing primer can bind, an index sequence, a binding sequence for separating said DSB from a pool of DSBs and a 5' binding and/or protective feature. The 3' binding feature may comprise a 3' deoxythymidine triphosphate 'T-tail' and also a phosphorothioate linkage.

Either the first and/or second oligonucleotide of the first oligonucleotide pair of part i) may comprise two different terminal protective features. The 5' binding feature of said first oligonucleotide of the second oligonucleotide pair of part iii) may be a phosphate group and said 3' binding feature of said second oligonucleotide of part iii) may be a triphosphate tail.

The first and second oligonucleotides of part iii) may also comprise an index feature that is a particular sequence of nucleotides that enables the origin of pooled samples to be determined.

The second oligonucleotide of part iii), reading 5' to 3' may comprise a 5' binding feature and then, optionally, a protective feature, a further sequence for, optionally, enabling bridge amplification, an index sequence, a hybridization site (RD2 SP) to which a sequencing primer can bind, and a 3' binding and/or protective feature.

Either the first or second oligonucleotide of the second oligonucleotide pair of part iii) may comprise two different terminal protective features.

The oligonucleotides of part i) may comprise a first oligonucleotide having SEQ ID NO. 1 and a second oligonucleotide having SEQ ID NO. 2; or an oligonucleotide that shares at least 80% identity or homology with SEQ ID NO. 1 or 2. The second pair of oligonucleotides of part iii) may comprise a first oligonucleotide having SEQ ID NO. 3 and a second oligonucleotide having SEQ ID NO. 4; or an oligonucleotide that shares at least 80% identity or homology with SEQ ID NO. 3 or 4. The second oligonucleotide of said second pair of oligonucleotides of part iii) may comprise any one of the following sequences; SEQ ID NOs. 4-28; or an oligonucleotide that shares at least 80% identity or homology with one of SEQ ID NO. 4-28.

The sample may be mammalian or human. The ligation in part i) may occur in situ or in vitro using a cell or tissue sample. The sample may be exposed to a permeabilizing agent before step i) is undertaken. The sample may be exposed to at least one agent for performing arginine tail repair before step i) is undertaken.

Part i) may also include extracting gDNA from said sample prior to performing the subsequent steps.

The method may further comprise after part ii) and/or part iv), removing fragments whose size is less than about 100 bp, or less than about 150 bp, and/or retaining fragments whose size is greater than about 150 bp.

The separating of part v) may involve using said binding sequence provided by the oligonucleotide of part i) to bind a partner and so separate the Group A strands of part iv) from any other strands.

A complementary binding strand to said binding sequence provided by the oligonucleotide of part i) may be anchored to a substrate and said single strands of nucleic acids flow by, or over, the anchored complementary binding strand.

Part vi) may involve bridge amplification where the single strands separated under part v) are clonally amplified on a substrate that has anchored thereon oligonucleotides/binding sites for the binding sequence of the first oligonucleotide of part i) and the further sequence of the second oligonucleotide of part iii).

Prior to performing the claimed method, a sample containing or suspected of containing, a single strand break may be ligated or broken to ensure the single strand break is converted into a double strand break.

In another aspect of the invention there is provided a kit of parts for identifying DNA double-strand breaks (DSBs) in a gDNA sample comprising
  i) a first pair of oligonucleotides a first one of which comprises a 5' binding feature that enables ligation of said oligonucleotide to a first strand of said DSB, a hybridization site (RD1 SP) to which a first sequencing primer can bind and a binding sequence for separating said DSB from a pool of DSBs; and a second oligonucleotide that is complementary to said first oligonucleotide of this first pair and comprises a 3' binding feature for binding to a second strand of said DSBs; and wherein either or both of said oligonucleotides comprise a 3' and/or 5' protective feature; and
  ii) a second pair of oligonucleotides a first one of which comprises a 5' binding feature, that enables ligation of said oligonucleotide to a first strand of said DSB, and a hybridization site (RD2 SP) to which a second sequencing primer can bind; and a second longer oligonucleotide that is in part complementary to said first oligonucleotide of this second pair and comprises a 3' binding feature for binding to a second strand of said DSBs, a sequence complimentary to said hybridization site, and a further sequence which is, optionally, a binding sequence for enabling bridge amplification; and wherein either or both of said oligonucleotides comprise a 3' and/or 5' protective feature.

In another aspect of the invention there is provided a kit for sample preparation for identifying DSBs in a gDNA sample, comprising
  i) a first pair of oligonucleotides, a first one of which comprises a 5' binding feature that enables ligation of said oligonucleotide to a strand of a double-stranded nucleic acid, and comprises a sequence according to TCGGTGGTCGCCGTATCATT (SEQ ID NO: 31); and a second oligonucleotide that is complementary to said first oligonucleotide of the first pair; and wherein either or both of said oligonucleotides comprise, respectively, a 3' and/or 5' protective feature; and
  ii) a second pair of oligonucleotides, a first one of which does not comprise a sequence of more than 5, 10, 15, or 20 bases, or does not comprise all 24 bases, of the sequence ATCTCGTATGCCGTCTTCTGCTTG (SEQ ID NO: 30); and a second oligonucleotide that comprises a 3' binding feature that enables ligation of said oligonucleotide to a strand of a double-stranded nucleic acid and comprises a sequence according to CAAGCAGAAGACGGCATACGAGAT (SEQ ID NO: 32); and wherein either or both of said oligonucleotides comprise, respectively, a 3' and/or 5' protective feature.

In another aspect of the invention there is provided a kit for sample preparation for identifying DSBs in a gDNA sample, comprising
  i) a first pair of oligonucleotides, a first one of which comprises a 5' binding feature that enables ligation of said oligonucleotide to a strand of a double-stranded nucleic acid, and comprises a sequence according to ATCTCGTATGCCGTCTTCTGCTTG (SEQ ID NO: 30); and a second oligonucleotide that is complementary to said first oligonucleotide of the first pair; and wherein either or both of said oligonucleotides comprise, respectively, a 3' and/or 5' protective feature; and
  ii) a second pair of oligonucleotides, a first one of which does not comprise a sequence of more than 5, 10, or 15 bases, or does not comprise all 20 bases, of the sequence TCGGTGGTCGCCGTATCATT (SEQ ID NO: 31); and a second oligonucleotide that comprises a 3' binding feature that enables ligation of said oligonucleotide to a strand of a double-stranded nucleic acid and comprises a sequence according to AATGATACGGCGACCACCGA (SEQ ID NO: 34); and wherein either or both of said oligonucleotides comprise, respectively, a 3' and/or 5' protective feature.

The first oligonucleotide of the first pair and/or the second pair of oligonucleotides may comprise a hybridization site to which a first sequencing primer can bind. The first and second oligonucleotides of part i) and/or part ii) may comprise an index feature that is a particular sequence of nucleotides that enables the origin of pooled samples to be determined.

The kit may further comprise at least one primer that bind to the first and/or second hybridization sites for the purpose of sequencing. The kit may further comprise fragmenting agents and/or denaturing agents for fragmenting and/or denaturing the nucleic acid into fragments and/or single strands, respectively.

In another aspect of the invention there is provided a double strand adaptor for identifying DNA double-strand breaks (DSBs) in a nucleic acid sample, such as a gDNA sample, comprising: a first oligonucleotide strand comprising a 5' binding feature that enables ligation of said oligonucleotide to a first strand of said DSB, a hybridization site (RD1 SP) to which a sequencing primer can bind and a binding sequence for separating said DSB from a pool of DSBs; and a second oligonucleotide strand that is complementary to said first oligonucleotide and comprises a 3' binding feature for binding to a second strand of said DSBs; and wherein either or both of said oligonucleotides comprise a 3' and/or 5' protective feature.

In another aspect of the invention there is provided a double strand adaptor for identifying DNA double-strand breaks (DSBs) in a nucleic acid sample, such as a gDNA sample, comprising: a first oligonucleotide strand comprising a 5' binding feature, that enables ligation of said oligonucleotide to a first strand of said DSB, and a hybridization site (RD2 SP) to which a sequencing primer can bind; and a second longer oligonucleotide strand that is in part complementary to said first oligonucleotide and comprises a 3' binding feature for binding to a second strand of said DSBs, a sequence complimentary to said hybridization site, and a further sequence, which is, optionally, a binding sequence for enabling bridge amplification; and wherein either or both of said oligonucleotides comprise a 3' and/or 5' protective feature.

The adaptor may comprise first and second oligonucleotides that comprise an index feature that is a particular sequence of nucleotides that enables the origin of pooled samples to be determined.

In another aspect of the invention there is provided a double strand adaptor for identifying DNA double-strand breaks (DSBs) in a nucleic acid sample, comprising: a first oligonucleotide strand which does not comprise a sequence of more than 5, 10, 15, or 20 bases, or does not comprise all 24 bases, of the sequence ATCTCGTATGCCGT-CTTCTGCTTG (SEQ ID NO: 30); and a second oligonucleotide that comprises a 3' binding feature that enables ligation of said oligonucleotide to a strand of a double-stranded nucleic acid and comprises a sequence according to CAAGCAGAAGACGGCATACGAGAT (SEQ ID NO: 32); and wherein either or both of said oligonucleotides comprise, respectively, a 3' and/or 5' protective feature.

In another aspect of the invention there is provided a double strand adaptor for identifying DNA double-strand breaks (DSBs) in a nucleic acid sample, comprising: a first oligonucleotide strand which does not comprise a sequence of more than 5, 10, or 15 bases, or does not comprise all 20 bases, of the sequence TCGGTGGTCGCCGTATCATT (SEQ ID NO: 31); and a second oligonucleotide that comprises a 3' binding feature that enables ligation of said oligonucleotide to a strand of a double-stranded nucleic acid and comprises a sequence according to AATGA-TACGGCGACCACCGA (SEQ ID NO: 34); and wherein either or both of said oligonucleotides comprise, respectively, a 3' and/or 5' protective feature.

In another aspect of the invention there is provided a method of sample preparation for identifying DNA double-strand breaks (DSBs) in a nucleic acid sample, wherein the preparation comprises modifying DSB-associated nucleic acids to be suitable for binding to a substrate comprising immobilised primers, the method comprising:
  a) providing a sample comprising a plurality of nucleic acids;
  b) exposing the plurality of nucleic acids to a first adaptor under conditions conducive to ligation, wherein the first adaptor comprises an oligonucleotide capable of being ligated to a 3' terminus of a strand of a DSB and which comprises a sequence that is capable of binding to a primer immobilised to the substrate by hybridisation;
  c) fragmenting the plurality of nucleic acids; and
  d) exposing the plurality of nucleic acids to a second adaptor under conditions conducive to ligation, wherein the second adaptor comprises an oligonucleotide capable of being ligated to a 5' terminus of a strand at a break induced by fragmentation, but is not capable of being ligated to the first adaptor, and which does not comprise a sequence that is capable of binding to a primer immobilised to the substrate by hybridisation.

The oligonucleotide of step d) may comprise a sequence identical to a region of a second primer. The substrate may comprise a first and a second immobilised primer; the oligonucleotide of step b) may comprise a sequence that is capable of binding to the first immobilised primer by hybridisation; and the oligonucleotide of step d) may comprise a sequence identical to a region of the second immobilised primer.

In an embodiment, step b) is: exposing the plurality of nucleic acids to a first adaptor pair under conditions conducive to ligation, wherein the first adaptor pair is capable of being ligated to at least a 3' terminus of a strand of a DSB, and wherein the first adaptor pair comprises first and second oligonucleotides that are at least partially complementary, and the first oligonucleotide is ligatable to a 3' terminus and comprises a sequence that is capable of binding to a primer immobilised to the substrate by hybridisation; and step d) is:
  exposing the plurality of nucleic acids to a second adaptor pair under conditions conducive to ligation, wherein the second adaptor pair is capable of being ligated to at least a 5' terminus of a strand at a break induced by fragmentation but is not capable of being ligated to the first oligonucleotide of the first adaptor pair, wherein the second adaptor comprises first and second partially complementary oligonucleotides, and the first oligonucleotide is ligatable to a 5' terminus and comprises a sequence identical to a region of a second primer, and the second oligonucleotide does not comprise a sequence that is complementary to said sequence identical to a region of the second primer.

In an embodiment of the method, the second adaptor pair comprises:
  a first oligonucleotide comprising a sequence according to CAAGCAGAAGACGGCATACGAGAT (SEQ ID NO: 32), and a second oligonucleotide comprising a sequence that does not comprise a sequence of more than 5, 10, 15, or 20 bases, or does not comprise all 24 bases, of the sequence ATCTCGTATGCCGTC-TTCTGCTTG (SEQ ID NO: 30); or
  a first oligonucleotide comprising a sequence according to AATGATACGGCGACCACCGA (SEQ ID NO: 34), and a second oligonucleotide comprising a sequence that does not comprise a sequence of more than 5, 10, or 15 bases, or does not comprise all 20 bases, of the sequence TCGGTGGTCGCCGTATCATT (SEQ ID NO: 31).

The first and/or the second oligonucleotide of the first adaptor pair may comprise a 3' and/or 5' protective feature; and/or wherein the first and/or the second oligonucleotide of the second adaptor pair may comprise a 3' and/or 5' protective feature. In an embodiment, the second adaptor is not capable of being ligated to the first adaptor due to the presence of a 3' modification of the first adaptor.

In an embodiment the oligonucleotide of the second adaptor that is ligatable to a 5' terminus comprises a sequence identical to 5, 10, 15, 20, 21, 24, or more bases of an immobilised primer.

The method may further comprise denaturing the plurality of nucleic acids to form a plurality of single-stranded nucleic acids. The method may further comprise contacting the plurality of nucleic acids with the substrate comprising immobilised primers under conditions suitable for hybridisation of the immobilised primers to complementary nucleic acids. The method may further comprise obtaining sequence information for any nucleic acids hybridised to the substrate.

In an embodiment of the method, the sample comprising a plurality of nucleic acids is gDNA.

In some embodiments, the steps are performed in the order a), b), c), and then d). In other embodiments, the steps are performed in the order a), c), d), and then b); wherein the sample is exposed to conditions capable of causing or suspected of being capable of causing a DSB between steps d) and b).

In some embodiments, the sample is exposed to conditions capable of causing a DSB at a feature of interest in the nucleic acid sample.

In another aspect of the invention there is provided a method of sample preparation for identifying DNA double-strand breaks (DSBs) in a nucleic acid sample, wherein the preparation comprises modifying DSB-associated nucleic acids to be suitable for binding to a substrate comprising an immobilised first primer, the method comprising:
1) providing a sample comprising a plurality of nucleic acids;
2) exposing the plurality of nucleic acids to a first adaptor under conditions conducive to ligation, wherein the first adaptor comprises an oligonucleotide capable of being ligated to a 3' terminus of a strand of a DSB and which comprises a sequence that is capable of hybridising to a second primer;
3) fragmenting the plurality of nucleic acids;
4) exposing the plurality of nucleic acids to a second adaptor under conditions conducive to ligation, wherein the second adaptor comprises an oligonucleotide capable of being ligated to a 5' terminus of a strand at a break induced by fragmentation, but is not capable of being ligated to the first adaptor, and which comprises a sequence identical to a region of the immobilised first primer; and
5) contacting the plurality of nucleic acids with the second primer under conditions suitable for extension of the primer.

In an embodiment, step 2) is: exposing the plurality of nucleic acids to a first adaptor pair under conditions conducive to ligation, wherein the first adaptor pair is capable of being ligated to at least a 3' terminus of a strand of a DSB, and wherein the first adaptor pair comprises first and second oligonucleotides that are at least partially complementary, and the first oligonucleotide is ligatable to a 3' terminus and comprises a sequence that is capable of hybridising to a second primer; and step 4) is:
exposing the plurality of nucleic acids to a second adaptor pair under conditions conducive to ligation, wherein the second adaptor pair is capable of being ligated to at least a 5' terminus of a strand at a break induced by fragmentation but is not capable of being ligated to the first oligonucleotide of the first adaptor pair, wherein the second adaptor comprises first and second partially complementary oligonucleotides, and the first oligonucleotide is ligatable to a 5' terminus and comprises a sequence identical to a region of the immobilised first primer, and the second oligonucleotide does not comprise a sequence that is complementary to said sequence identical to a region of the immobilised first primer.

The second adaptor pair may comprise a first oligonucleotide comprising a sequence according to AACCCACTACGCCTCCGCTTTCC (SEQ ID NO: 40); and a second oligonucleotide that does not comprise a sequence of more than 5, 10, 15, 20 bases, or does not comprise all 22 bases, of the sequence GGAAAGCGGAGGCGTAGTGGTT (SEQ ID NO: 36).

The first and/or the second oligonucleotide of the first adaptor pair may comprise a 3' and/or 5' protective feature; and/or wherein the first and/or the second oligonucleotide of the second adaptor pair comprises a 3' and/or 5' protective feature. In an embodiment, the second adaptor is not capable of being ligated to the first adaptor due to the presence of a 3' modification of the first adaptor.

In an embodiment, the oligonucleotide of the second adaptor that is ligatable to a 5' terminus comprises a sequence identical to 5, 10, 15, 20, 21, 24, or more bases of an immobilised primer.

The method may further comprise denaturing the plurality of nucleic acids to form a plurality of single-stranded nucleic acids. The method may further comprise contacting the plurality of nucleic acids with the substrate comprising the immobilised first primer under conditions suitable for hybridisation of the immobilised first primer to complementary nucleic acids. The method may further comprise obtaining sequence information for any nucleic acids hybridised to the substrate. The sample comprising may be gDNA.

In an embodiment, the steps are performed in the order 1), 2), 3), 4), and then 5). In another embodiment, the steps are performed in the order 1), 3), 4), 2), and then 5); wherein the sample is exposed to conditions capable of causing or suspected of being capable of causing a DSB between steps 4) and 2).

In an embodiment, the sample is exposed to conditions capable of causing a DSB at a feature of interest in the nucleic acid sample.

In another aspect of the invention there is provided a method of sample preparation for identifying a feature of interest in a nucleic acid sample, wherein the preparation comprises modifying nucleic acids associated with a feature of interest to be suitable for binding to a substrate comprising immobilised primers, the method comprising:
a) providing a sample comprising a plurality of nucleic acids, exposing the plurality of nucleic acids to conditions capable of cleaving at least one strand of a nucleic acid at a feature of interest, and denaturing the plurality of nucleic acids into single-stranded nucleic acids;
b) exposing the plurality of nucleic acids to a first adaptor under conditions conducive to ligation, wherein the first adaptor comprises an oligonucleotide capable of being ligated to a 3' terminus of a strand of a cleavage site and which comprises a sequence that is capable of binding to a primer immobilised to the substrate by hybridisation;
c) fragmenting the plurality of nucleic acids; and
d) exposing the plurality of nucleic acids to a second adaptor under conditions conducive to ligation, wherein the second adaptor comprises an oligonucleotide capable of being ligated to a 5' terminus of a strand at a break induced by fragmentation, but is not capable of being ligated to the first adaptor, and which does not comprise a sequence that is capable of binding to a primer immobilised to the substrate by hybridisation.

The feature of interest may be any feature capable of being specifically cleaved. The feature of interest may be a cyclobutane pyrimidine dimer (CPD), 8-oxoguanine, or an abasic site.

The oligonucleotide of step d) may comprise a sequence identical to a region of a second primer. The substrate may comprise a first and a second immobilised primer; the oligonucleotide of step b) may comprise a sequence that is capable of binding to the first immobilised primer by hybridisation; and the oligonucleotide of step d) may comprise a sequence identical to a region of the second immobilised primer.

In an embodiment, step b) is: exposing the plurality of nucleic acids to a first adaptor pair under conditions conducive to ligation, wherein the first adaptor pair is capable of being ligated to at least a 3' terminus of a strand of a cleavage site, and wherein the first adaptor pair comprises first and second oligonucleotides that are at least partially complementary, and the first oligonucleotide is ligatable to a 3' terminus and comprises a sequence that is capable of binding to a primer immobilised to the substrate by hybridisation; and wherein step d) is:

exposing the plurality of nucleic acids to a second adaptor pair under conditions conducive to ligation, wherein the second adaptor pair is capable of being ligated to at least a 5' terminus of a strand at a break induced by fragmentation but is not capable of being ligated to the first oligonucleotide of the first adaptor pair, wherein the second adaptor comprises first and second partially complementary oligonucleotides, and the first oligonucleotide is ligatable to a 5' terminus and comprises a sequence identical to a region of a second primer, and the second oligonucleotide does not comprise a sequence that is complementary to said sequence identical to a region of the second primer.

In an embodiment, the second adaptor pair comprises:
a first oligonucleotide comprising a sequence according to CAAGCAGAAGACGGCATACGAGAT (SEQ ID NO: 32), and a second oligonucleotide comprising a sequence that does not comprise a sequence of more than 5, 10, 15, or 20 bases, or does not comprise all 24 bases, of the sequence ATCTCGTATGCCG-TCTTCTGCTTG (SEQ ID NO: 30); or
a first oligonucleotide comprising a sequence according to AATGATACGGCGACCACCGA (SEQ ID NO: 34), and a second oligonucleotide comprising a sequence that does not comprise a sequence of more than 5, 10, or 15 bases, or does not comprise all 20 bases, of the sequence TCGGTGGTCGCCGTATCATT (SEQ ID NO: 31).

The first and/or the second oligonucleotide of the first adaptor pair may comprise a 3' and/or 5' protective feature; and/or wherein the first and/or the second oligonucleotide of the second adaptor pair may comprise a 3' and/or 5' protective feature. In an embodiment, the second adaptor is not capable of being ligated to the first adaptor due to the presence of a 3' modification of the first adaptor.

The oligonucleotide of the second adaptor that is ligatable to a 5' terminus may comprise a sequence identical to 5, 10, 15, 20, 21, 24, or more bases of an immobilised primer.

In an embodiment, the method further comprises denaturing the plurality of nucleic acids to form a plurality of single-stranded nucleic acids. In an embodiment, the method further comprises contacting the plurality of nucleic acids with the substrate comprising immobilised primers under conditions suitable for hybridisation of the immobilised primers to complementary nucleic acids. In an embodiment, the method further comprises obtaining sequence information for any nucleic acids hybridised to the substrate.

In an embodiment, the sample comprising a plurality of nucleic acids is gDNA. In an embodiment, the steps are performed in the order a), b), c), and then d). In another embodiment, the steps are performed in the order c), d), a), and then b).

In an another aspect of the invention, there is provided a double strand adaptor for identifying DNA double-strand breaks (DSBs) in a nucleic acid sample, such as a gDNA sample, comprising: a first oligonucleotide strand that does not comprise a sequence of more than 5, 10, 15, 20 bases, or does not comprise all 22 bases, of the sequence GGAAAGCGGAGGCGTAGTGGTT (SEQ ID NO: 36); and a second oligonucleotide that comprises a 3' binding feature that enables ligation of said oligonucleotide to a strand of a double-stranded nucleic and acid comprises a sequence according to AACCCACTACGCCTCCG-CTTTCC (SEQ ID NO: 40); and wherein either or both of said oligonucleotides comprise, respectively, a 3' and/or 5' protective feature.

DESCRIPTION OF THE DRAWINGS

FIG. 3. INDUCE-seq demonstrates unparalleled sensitivity and dynamic range when compared to alternative DSB sequencing technologies. (FIG. 3b) Mapping of INDUCE-seq reads at a HindIII target site demonstrates precision of single-nucleotide break mapping. This figure includes TACTCAAGCTTACCCCTA (SEQ ID NO: 35) and GGGGGGTAAGCTTGAGTA (SEQ ID NO: 43). (FIG. 3c) Quantification of breaks measured per cell for the HindIII treated and control samples. INDUCE-seq quantitatively detects breaks-per-cell across 3 orders of magnitude between samples. (d and e) Comparison between INDUCE-seq and DSBCapture in detecting in vitro cleaved restriction sites by the enzymes HindIII and EcoRV. (FIG. 3d) A greater proportion of reads sequenced and aligned to the genome were mapped to restriction sites using INDUCE-seq. (FIG. 3e) Using 800-fold fewer cells, INDUCE-seq identifies a similar proportion of HindIII restriction sites (92.7%) to that identified by DSBCapture for EcoRV (93.7%). (FIG. 3f) The dynamic range of induced DSB detection using INDUCE-seq. In addition to breaks identified at HindIII on-target sequences (AAGCTT), multiple 1 bp and 2 bp mismatching off-target sites were also identified. INDUCE-seq measured induced break events spanning 8 orders of magnitude, from ~150 million breaks identified at HindIII on-target sites, to 5 breaks identified at the rarest off-target.

FIG. 4. INDUCE-seq sensitively discovers and quantifies CRISPR/Cas9 induced on- and off-target DSBs.

FIG. 7. Genome browser view of DSB hotspots in HEK293 cells.

FIG. 15. Exemplary adaptors for use with bead sequencing technology.

Figure 1:
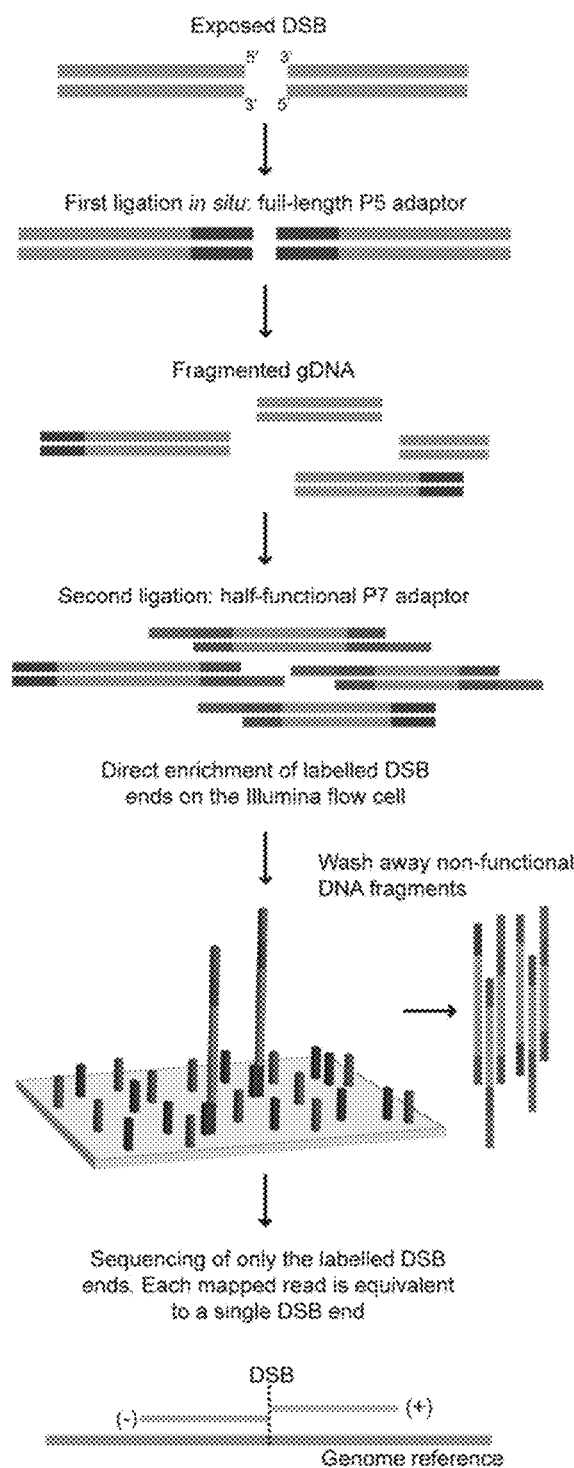
FIG. 1. Overview of INDUCE-seq. In situ break labelling in fixed and permeabilised cells is performed by ligating a full-length chemically modified P5 sequencing adaptor to end-prepared DSBs. Genomic DNA is then extracted, fragmented, end-prepared and ligated using a chemically modified half-functional P7 adaptor. Resulting DNA libraries contain a mixture of functional DSB-labelled fragments (P5:P7) and non-functional genomic DNA fragments (P7:P7). Subsequent sequencing of INDUCE-seq libraries enriches for DNA-labelled fragments and eliminates all other non-functional DNA. As the INDUCE-seq library preparation is PCR-free, each sequencing read obtained is equivalent to a single labelled DSB end.

Table 1. Example adaptor sequences according to a preferred embodiment of the invention.

DETAILED DESCRIPTION

In an aspect of the invention, there is provided a method for identifying DNA double-strand breaks (DSBs) in a nucleic acid sample comprising
i) exposing a sample of nucleic acid suspected of containing DSBs, under ligation conditions, to a first pair of oligonucleotides a first one of which comprises a 5' binding feature that enables ligation of said oligonucleotide to a first strand of said DSB, a hybridization site (RD1 SP) to which a first sequencing primer can bind and a binding sequence for separating said DSB from a pool of DSBs; and a second oligonucleotide that is complementary to said first oligonucleotide of the first pair and comprises a 3' binding feature that enables ligation of said oligonucleotide to a second strand of said DSBs; wherein either or both of said oligonucleotides comprise a 3' and/or 5' protective feature;

ii) fragmenting the nucleic acid sample, ideally gDNA, into fragments;

iii) exposing said fragments, under ligation conditions, to a second pair of oligonucleotides a first one of which comprises a 5' binding feature, that enables ligation of said oligonucleotide to a first strand of said fragment, ideally at a site remote from the binding of said oligonucleotide of said first pair, and a hybridization site (RD2 SP) to which a second sequencing primer can bind; and a second longer oligonucleotide that is in part complementary to said first oligonucleotide of the second pair and comprises a 3' binding feature for binding to a second strand of said fragments or said DSBs, a sequence complimentary to said hybridization site, and a further sequence, optionally, a binding sequence for enabling bridge amplification; and wherein either or both of said oligonucleotides comprise a 3' and/or 5' protective feature;

iv) denaturing the fragments to provide single nucleic acids;

v) separating the strands of part iv) into two groups: group A those fragments that have ligated at a first end the first hybridization site and binding sequence provided by the oligonucleotide of part i) and at another end the second hybridization site and further sequence provided by the oligonucleotide of part iii) and group B those fragments that do not have ligated at a first end the hybridization site and binding sequence provided by the oligonucleotide of part i) and at another end the second hybridization site and further sequence provided by the oligonucleotide of part iii); and vi) sequencing the strands of group A using primers that bind to the first and/or second hybridization sites where each sequence is equivalent to a break, typically one DSB. Optionally further wherein the number and nature of base pair deletions can be determined by comparing each sequence with a genome representative of said species from which the sample was taken.

The steps of the method of the invention need not be performed at one time or in one location. For instance, in an aspect, the method of the invention allows the preparation of a nucleic acid sample which has been labelled in a manner that would allow the selection and isolation of DSBs. As such, in an aspect of the invention, there is provided a method of sample preparation for identifying DNA double-strand breaks (DSBs) in a nucleic acid sample comprising i) exposing a sample of nucleic acid suspected of containing DSBs, under ligation conditions, to a first pair of oligonucleotides a first one of which comprises a 5' binding feature that enables ligation of said oligonucleotide to a first strand of said DSB, a hybridization site (RD1 SP) to which a first sequencing primer can bind and a binding sequence for separating said DSB from a pool of DSBs; and a second oligonucleotide that is complementary to said first oligonucleotide of the first pair and comprises a 3' binding feature that enables ligation of said oligonucleotide to a second strand of said DSBs; wherein either or both of said oligonucleotides comprise a 3' and/or 5' protective feature;

ii) fragmenting the nucleic acid sample, ideally gDNA, into fragments; and iii) exposing said fragments, under ligation conditions, to a second pair of oligonucleotides a first one of which comprises a 5' binding feature, that enables ligation of said oligonucleotide to a first strand of said fragment, optionally at a site remote from the binding of said oligonucleotide of said first pair, and a hybridization site (RD2 SP) to which a second sequencing primer can bind; and a second longer oligonucleotide that is in part complementary to said first oligonucleotide of the second pair and comprises a 3' binding feature for binding to a second strand of said fragment, a sequence complimentary to said hybridization site, and a further sequence, optionally, a binding sequence for enabling bridge amplification; and wherein either or both of said oligonucleotides comprise a 3' and/or 5' protective feature.

Alternatively, the methods of the invention may be carried out until the strands are separated into group A and group B, and the sequencing may be carried out separately. Thus, the method allows the preparation of a nucleic acid sample wherein any DSBs have been selected and isolated. As such, in an embodiment, there is provided a method of sample preparation for identifying DNA double-strand breaks (DSBs) in a nucleic acid sample comprising i) exposing a sample of nucleic acid suspected of containing DSBs, under ligation conditions, to a first pair of oligonucleotides a first one of which comprises a 5' binding feature that enables ligation of said oligonucleotide to a first strand of said DSB, a hybridization site (RD1 SP) to which a first sequencing primer can bind and a binding sequence for separating said DSB from a pool of DSBs; and a second oligonucleotide that is complementary to said first oligonucleotide of the first pair and comprises a 3' binding feature that enables ligation of said oligonucleotide to a second strand of said DSBs; wherein either or both of said oligonucleotides comprise a 3' and/or 5' protective feature;

ii) fragmenting the nucleic acid sample, ideally gDNA, into fragments;

iii) exposing said fragments, under ligation conditions, to a second pair of oligonucleotides a first one of which comprises a 5' binding feature, that enables ligation of said oligonucleotide to a first strand of said fragment, optionally at a site remote from the binding of said oligonucleotide of said first pair, and a hybridization site (RD2 SP) to which a second sequencing primer can bind; and a second longer oligonucleotide that is in part complementary to said first oligonucleotide of the second pair and comprises a 3' binding feature for binding to a second strand of said fragment, a sequence complimentary to said hybridization site, and a further sequence, optionally, a binding sequence for enabling bridge amplification; and wherein either or both of said oligonucleotides comprise a 3' and/or 5' protective feature;

iv) denaturing the fragments to provide single nucleic acids; and v) separating the strands of part iv) into two groups: group A those fragments that have ligated at a first end the first hybridization site and binding sequence provided by the oligonucleotide of part i) and at another end the second hybridization site and further sequence provided by the oligonucleotide of part iii) and group B those fragments that do not have ligated at a first end the hybridization site and binding sequence provided by the oligonucleotide of part i) and at another end the second hybridization site and further sequence provided by the oligonucleotide of part iii).

In an aspect of the invention, there is provided a method for identifying DNA double-strand breaks (DSBs) in a nucleic acid sample comprising i) exposing a sample of nucleic acid suspected of containing DSBs, under ligation conditions, to a first pair of oligonucleotides a first one of which comprises a 5' binding feature that enables ligation of said oligonucleotide to a first strand of said DSB, and a binding sequence for separating said DSB from a pool of DSBs; and a second oligonucleotide that is complementary to said first oligonucleotide of the first pair; wherein either or both of said oligonucleotides comprise a 3' and/or 5' protective feature;

ii) fragmenting the nucleic acid sample, for instance gDNA, into fragments;

iii) exposing said fragments, under ligation conditions, to a second pair of oligonucleotides a first one of which is in part complementary to a second oligonucleotide of the second pair; and a second oligonucleotide that comprises a 3' binding feature for binding to a second strand of said fragments, and optionally a binding sequence for enabling bridge amplification; and wherein either or both of said oligonucleotides comprise a 3' and/or 5' protective feature;

iv) denaturing the fragments to provide single nucleic acids;

v) separating the strands of part iv) into two groups: group A those fragments that have ligated at a first end the binding sequence provided by the oligonucleotide of part i) and optionally at another end the binding sequence for enabling bridge amplification provided by the oligonucleotide of part iii) and group B those fragments that do not have ligated at a first end the binding sequence provided by the oligonucleotide of part i) and optionally at another end the binding sequence for enabling bridge amplification provided by the oligonucleotide of part iii); and vi) sequencing the strands of group A, where each sequence is equivalent to a break, typically one DSB, and optionally further wherein the number and nature of base pair deletions can be determined by comparing each sequence with a genome representative of said species from which the sample was taken. As discussed above, the method may comprise steps i), ii), and iii); or i), ii), iii), iv), and v); or all steps.

In particular embodiments, the oligonucleotide of the second pair that comprises a 5' binding feature does not comprise a binding sequence for separating said fragmented nucleic acid.

In embodiments of the invention, the oligonucleotides of part i) and part iii) may be interchanged whereby the nucleic acid is first exposed to the oligonucleotides of part iii) and are then exposed to the oligonucleotides of part i).

In an embodiment of the invention the oligonucleotides of part i) and part iii) may be interchanged whereby the nucleic acid is first exposed to the oligonucleotides of part iii) and after fragmenting, the nucleic acid fragments are then exposed to the oligonucleotides of part i).

Figure 13:
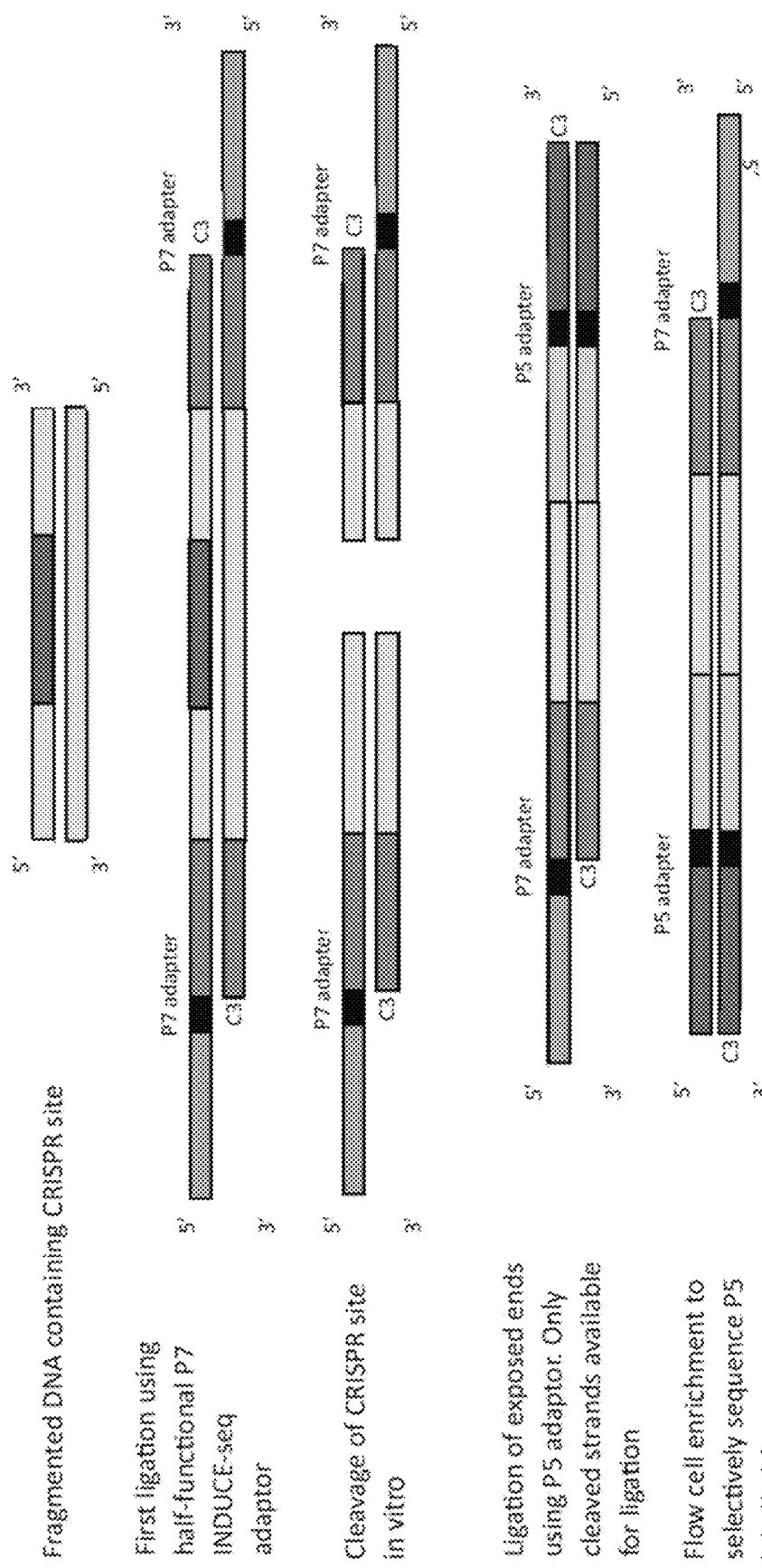
FIG. 13. Exemplary embodiment wherein the half-functional adaptor is ligated before the fully functional adaptor. This figure illustrates an embodiment for the detection of DSBs that are artificially induced. For instance, for the detection of off-target DSBs caused by nucleases.
Figure 17:
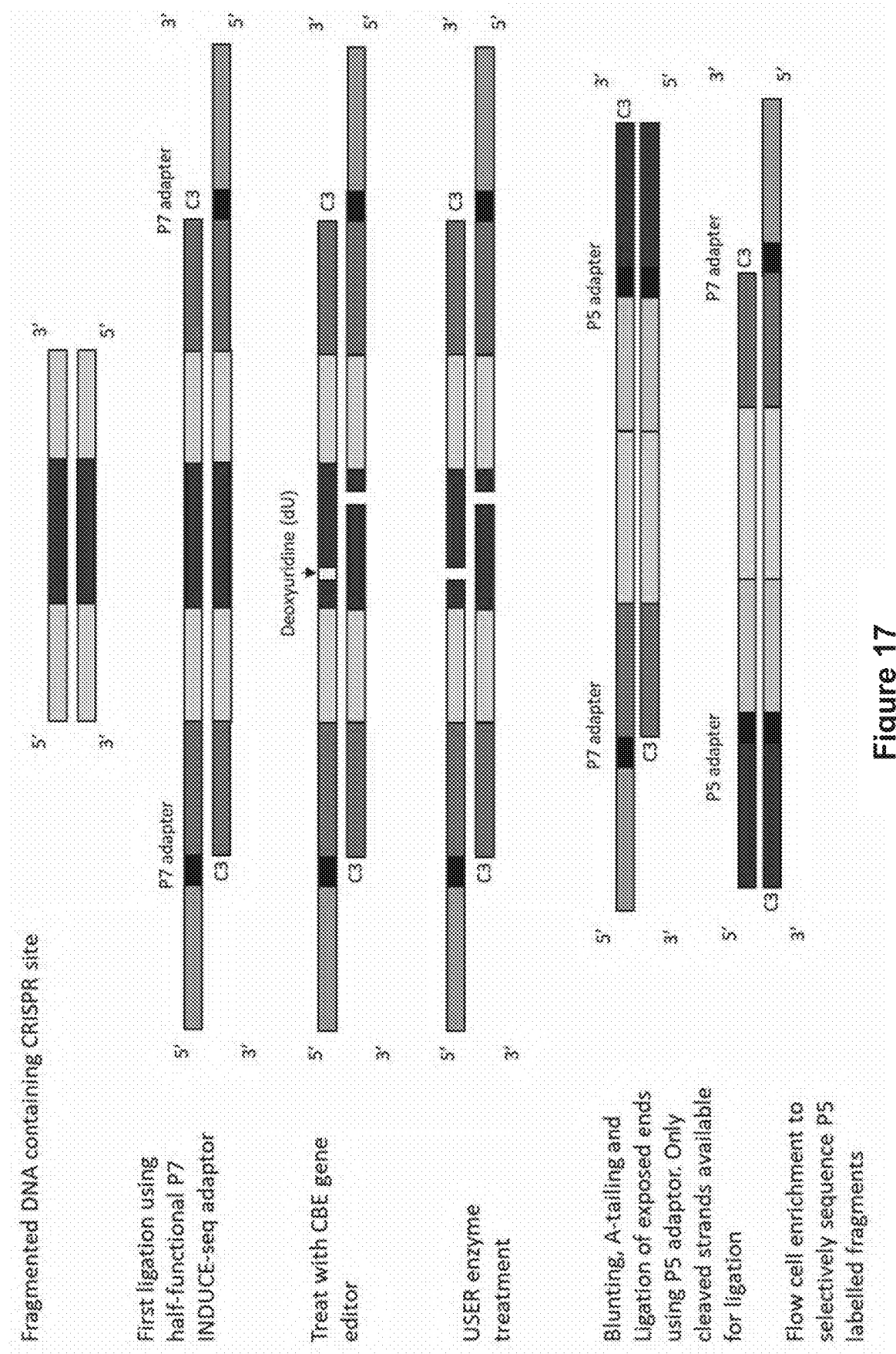
FIG. 17. Exemplary embodiment showing in vitro detection of CRISPR base editing-cytosine base editor (CBE).
Figure 18:
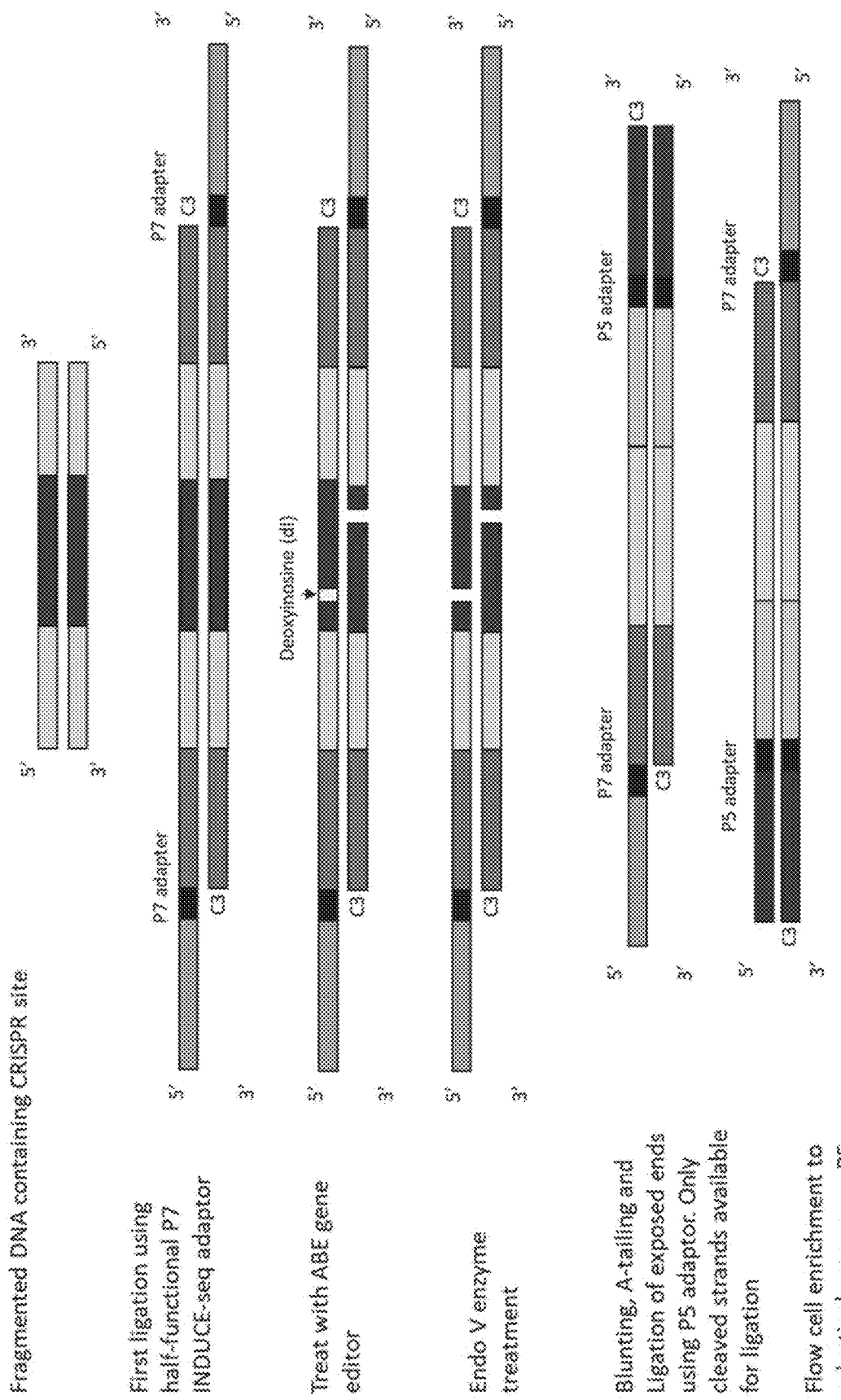
FIG. 18. Exemplary embodiment showing in vitro detection of CRISPR base editing-adenine base editor (ABE).

Embodiments involving the interchange of part i) and part iii) are particularly relevant to methods for the detection of DSBs that have been induced. In such embodiments, the sample may be fragmented and step iii) may be then performed. Subsequently, the sample may be treated to potentially induce a DSB and, following the induction, step i) may be performed. Embodiments wherein a DSB is introduced are further discussed herein, and include embodiments for the detection of off-target effects of nucleases, and the like. FIGS. 13, 17, and 18 illustrate particular embodiments.

In the method of the invention either of said pair of oligonucleotides may be, or may be known as, adaptors.

Reference herein to adaptors (or adapters) is reference to a linker in genetic engineering and it is an oligonucleotide that can be ligated to the ends of other DNA molecules. Adaptors may be double-stranded. Double stranded adaptors can be synthesized to have blunt ends to both terminals or to be sticky ended at one end and blunt end at the other. The adaptor may be short and may be chemically synthesized.

Figure 14:
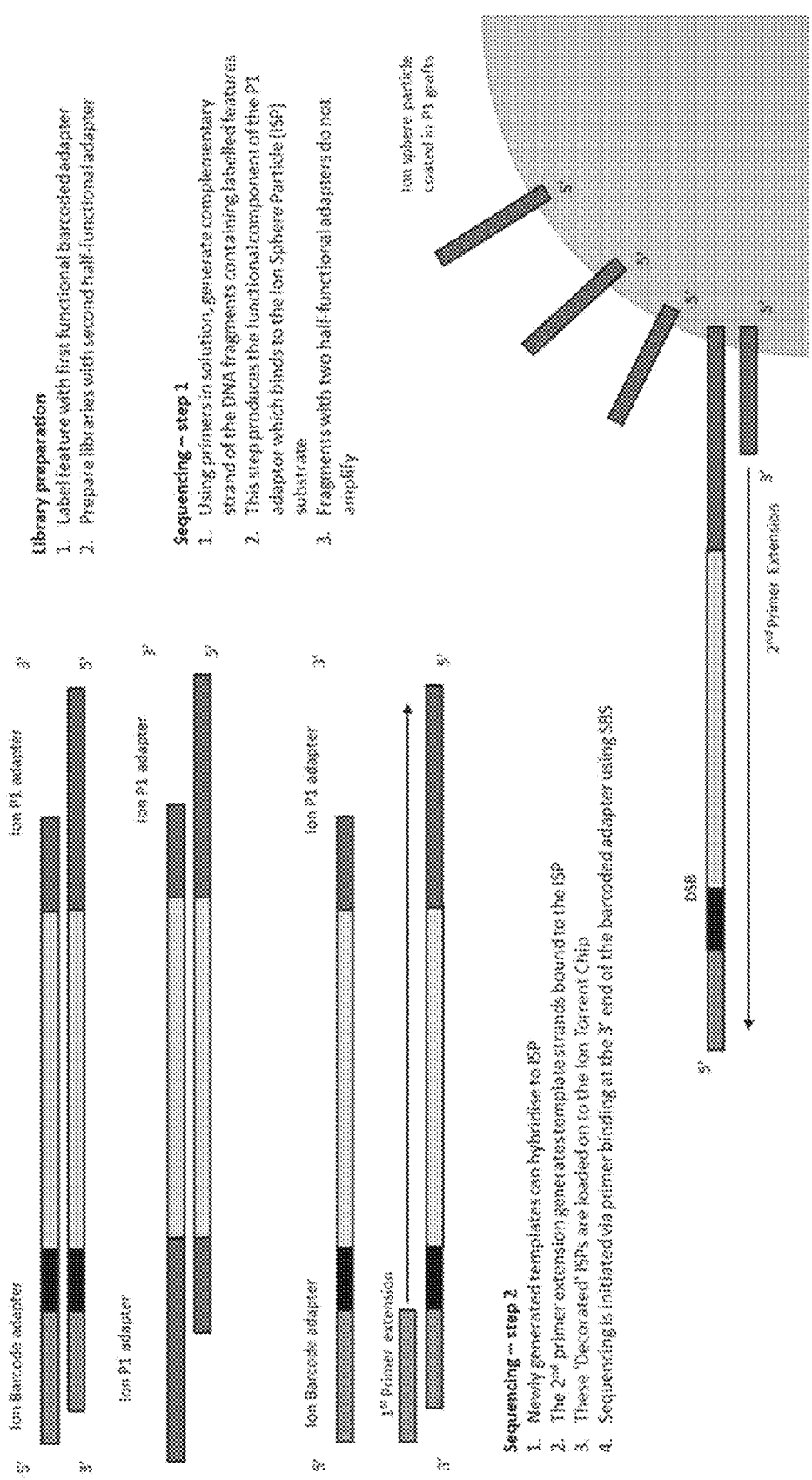
FIG. 14. Exemplary workflow for applying the methods of the invention to bead sequencing technology.

The first pair of oligonucleotides may be configured to allow binding to a substrate via hybridisation to an oligonucleotide immobilised to said substrate, wherein the immobilised oligonucleotide is oriented such that the 5' end is proximal and the 3' end is distal to the point of immobilisation. For instance, the oligonucleotide of the first pair that is ligated to the 3' terminus of a strand of a DSB (i.e. the oligonucleotide that comprised a 5' binding feature) may be at least partially complementary to an immobilised oligonucleotide. The extent of the complementarity may allow binding to the immobilised oligonucleotide via hybridisation. The second pair of oligonucleotides may be configured to not allow binding to a substrate via hybridisation to an oligonucleotide immobilised to said substrate, wherein the immobilised oligonucleotide is oriented such that the 5' end is proximal and the 3' end is distal to the point of immobilisation. For instance, the oligonucleotide of the second pair that is ligated to the 3' terminus of a strand of a fragmented site (i.e. the oligonucleotide that comprised a 5' binding feature) may be insufficiently complementary to any immobilised oligonucleotide to be able to bind via hybridisation. In some embodiments, for instance to allow subsequent bridge amplification, the oligonucleotide of the second pair that is bound to the 5' terminus of a strand of a fragmented site (i.e. the oligonucleotide that comprises a 3' binding feature) may be at least partially identical sequence to an immobilised oligonucleotide. In another embodiments, for instance to allow bead-emulsion amplification, the other arrangements may be used (for example, see FIG. 14).

In an embodiment, there is provided a method of sample preparation for identifying DNA double-strand breaks (DSBs) in a nucleic acid sample, wherein the preparation comprises modifying DSB-associated nucleic acids to be suitable for binding to a substrate comprising immobilised oligonucleotides, the method comprising i) exposing a sample of nucleic acid suspected of containing DSBs, under ligation conditions, to a first pair of oligonucleotides a first one of which comprises a 5' binding feature that enables ligation of said oligonucleotide to a first strand of said DSB, a hybridization site (RD1 SP) to which a first sequencing primer can bind and a binding sequence for separating said DSB from a pool of DSBs, wherein the binding sequence is at least partially complementary to an immobilised oligonucleotide; and a second oligonucleotide that is complementary to said first oligonucleotide of the first pair and comprises a 3' binding feature that enables ligation of said oligonucleotide to a second strand of said DSBs; wherein either or both of said oligonucleotides comprise a 3' and/or 5' protective feature;

ii) fragmenting the nucleic acid sample, ideally gDNA, into fragments; and iii) exposing said fragments, under ligation conditions, to a second pair of oligonucleotides a first one of which comprises a 5' binding feature, that enables ligation of said oligonucleotide to a first strand of said fragment, ideally at a site remote from the binding of said oligonucleotide of said first pair, a hybridization site (RD2 SP) to which a second sequencing primer can bind, and wherein the first oligonucleotide does not comprise a sequence capable of hybridising to an immobilised oligonucleotide; and a second longer oligonucleotide that is in part complementary to said first oligonucleotide of the second pair and comprises a 3' binding feature for binding to a second strand of said fragment, a sequence complimentary to said hybridization site, and a further sequence, optionally, a binding sequence for enabling bridge amplification; and wherein either or both of said oligonucleotides comprise a 3' and/or 5' protective feature.

A DSB-associated nucleic acid is a nucleic acid positioned on one side of a DSB. Hence the sequencing of a DSB-associated nucleic acid enables the location of a DSB, for instance in a genome, to be identified.

In an embodiment, the methods of the invention are designed for use with the Illumina P5 and P7 adaptors. Thus, in a particular embodiment, the second oligonucleotide pair does not comprise a sequence of more than 5, 10, 15, or 20 bases, or does not comprise all 24 bases, of the sequence ATCTCGTATGCCGTCTTCTGCTTG (SEQ ID NO: 30). In another embodiment, the second oligonucleotide pair does not comprise a sequence of more than 5, 10, or 15 bases, or does not comprise e all 20 bases, of the sequence TCGGTGGTCGCCGTATCATT (SEQ ID NO: 31).

Thus, in a particular embodiment, step iii) is:
exposing said fragments, under ligation conditions, to a second pair of oligonucleotides a first one of which comprises a 5' binding feature, that enables ligation of said oligonucleotide to a first strand of said fragment, ideally at a site remote from the binding of said oligonucleotide of said first pair, and a hybridization site (RD2 SP) to which a second sequencing primer can bind; and a second longer oligonucleotide that is in part complementary to said first oligonucleotide of the second pair and comprises a 3' binding feature for binding to a second strand of said DSBs, a sequence complimentary to said hybridization site, and a further sequence, optionally, a binding sequence for enabling bridge amplification; and wherein either or both of said oligonucleotides comprise a 3' and/or 5' protective feature; and wherein the second pair of oligonucleotides do not comprise a sequence of more than 5, 10, 15, 20, or 24 bases of SEQ ID NO: 30 and/or do not comprise a sequence of more than 5, 10, 15, or 20 bases of SEQ ID NO: 31.

In preferred method of the invention said 5' or 3' binding feature of said pair of oligonucleotides comprises one of the following: a phosphate group; a triphosphate 'T-tail', preferably a deoxythymidine triphosphate 'T-tail'; a triphosphate 'A-tail', preferably a deoxyadenosine triphosphate 'A-tail'; at least one random N nucleotide, preferably a plurality of N nucleotides, or any other known binding group to allow linkage of said adaptor to said DSB.

The nucleic acid sample may be any DNA sample capable of comprising DSBs. In a preferred embodiment of the invention said nucleic acid sample is gDNA.

More ideally still, said 5' binding feature of said first oligonucleotide of part i) is a phosphate group and said 3' binding feature of said second oligonucleotide of part i) is a triphosphate tail.

In a preferred embodiment of the invention, said 5' and/or 3' protective feature of said first pair of oligonucleotides comprises a feature that provides resistance to any one or more of the following: phosphorylation activity, phosphatase activity, terminal transferase activity, nucleic acid hybridization, endonuclease activity, exonuclease activity, ligase activity, polymerase activity, and protein binding. This can be achieved by any means known to those skilled in the art such as, but not limited to, phosphorothioate linkages, phosphoroamidite spacers, phosphate groups, 2'-O-Methyl groups, inverted deoxy and dideoxy-T modifications, locked nucleic acid bases, dideoxynucleotides, or the like. Examples of the activity these features provide are shown in table 2.

Preferably said first oligonucleotide of part i) comprises a 3' protective feature that provides resistance to exonuclease activity such as a phosphorothioate linkage. Additionally or alternatively said 3' protective feature also provides resistance to ligase activity and/or polymerase activity, ideally, 5'>3' polymerase activity and is for example a dideoxynucleotide or a physical block, ideally in the form of a phosphoramidite, in particular a C3 Spacer phosphoramidite (3SpC3), or any other protective feature known to those skilled in the art such as those in Table 2 that provides resistance to exonuclease activity and/or ligase activity and/or polymerase activity.

More preferably still said first and second oligonucleotides of part i) also comprise an index feature which is a particular sequence of nucleotides (e.g. GATCT) that enables the origin of pooled sequencing libraries to be determined, in other words, it enables demultiplexing of pooled sequencing libraries. Ideally, the index feature is located between said hybridization site and said binding sequence.

Most preferably, said first oligonucleotide of part i), reading 5' to 3' comprises a 5' binding feature and then, optionally, a protective feature, ideally the binding feature is a phosphate group, a hybridization site (RD1 SP) to which a first sequencing primer can bind, an index sequence, a binding sequence for separating said DSB from a pool of DSBs, and a 3' binding and/or protective feature. Preferably, said protective feature provides resistance to any one or more of the following: exonuclease activity, ligase activity and/or polymerase activity.

Most preferably, said second oligonucleotide of part i), reading 3' to 5' comprises a 3' binding and then, optionally, a protective feature, a hybridization sequence (RD1 SP) to which a first sequencing primer can bind, an index sequence, a binding sequence for separating said DSB from a pool of DSBs and a 5' binding and/or protective feature. Preferably, said protective features provide resistance to any one or more of the following: exonuclease activity, ligase activity and/or polymerase activity. Ideally the binding feature is 3'.

In a preferred embodiment of the invention said first oligonucleotide of part i) is one of a first oligonucleotide pair and the second oligonucleotide of this first oligonucleotide pair is complementary to said first oligonucleotide and comprises a 5' and a 3' protective feature, preferably, providing resistance to any one or more of the following: exonuclease activity, ligase activity and/or polymerase activity. Thus, in certain embodiments a 5' or 3' phosphate group is missing from the oligonucleotide used to work the invention.

In a preferred embodiment of the invention said first oligonucleotide of part i) contains both the hybridization site (/sequence) that is used to sequence the ligated DSB and the binding sequence that is used to separate said DSB from a pool of DSBs. However, those skilled in the art will appreciate that it is possible for the second oligonucleotide of part i) to contain both the hybridization site (/sequence) that is used to sequence the ligated DSB and the binding sequence that is used to separate said DSB from a pool of DSBs. This is because both the sequencing and separating will be determined by the nature of the primer used to sequence and the nature of the oligonucleotide used to separate. Most typically the orientation of all the oligonucleotides i.e. the orientation of the hybridization sites (RD1 SP & RD2 SP) to which at least a first, and/or second, sequencing primers can bind, and the binding sequence for separating said DSB from a pool of DSBs, and the further sequence, optionally, for enabling bridge amplification is such that when the separating of part v) is undertaken only Group A strands can be extracted using the binding sequence for separating said DSB from a pool of DSBs. Furthermore, this orientation is also such that when the sequencing of part vi) is undertaken only Group A strands can be bridged (when the bridge amplification sequence is present).

More ideally still, either the first or second oligonucleotide of the first oligonucleotide pair of part i) comprises two different terminal protective features.

Yet more preferably still the second oligonucleotide of this first oligonucleotide pair of part i) comprises a 3' deoxythymidine triphosphate 'T-tail', to provide a substrate for ligation to 'A-tailed' DNA fragments, and ideally also a phosphorothioate linkage whereby resistance to exonuclease activity is conferred.

In yet a further preferred method of the invention said 5' binding feature of said first oligonucleotide of the second oligonucleotide pair of part iii) is a phosphate group and said 3' binding feature of said second oligonucleotide of the second oligonucleotide pair of part iii) is a triphosphate tail.

In a preferred embodiment of the invention, said 5' and/or 3' protective feature of said second pair of oligonucleotides comprises a feature that provides resistance to any one or more of the following: phosphorylation activity, phosphatase activity, terminal transferase activity, nucleic acid hybridization, endonuclease activity, exonuclease activity, ligase activity, polymerase activity, and protein binding. This can be achieved by any means known to those skilled in the art such as, but not limited to, phosphorothioate linkages, phosphoroamidite spacers, phosphate groups, 2'-O-Methyl groups, inverted deoxy and dideoxy-T modifications, locked nucleic acid bases, dideoxynucleotides, or the like. Examples of the activity these features provide are shown in table 2.

Preferably said first oligonucleotide of part iii) also comprises a 3' protective feature that provides resistance to exonuclease activity such as a phosphoramidite spacer. Additionally or alternatively said 3' protective feature also provides resistance to ligase activity and/or polymerase activity, ideally, 5'>3' polymerase activity and is for example a dideoxynucleotide or a physical block, ideally in the form of a phosphoramidite, in particular a C3 Spacer phosphoramidite (3SpC3), or any other protective feature known to those skilled in the art such as those in Table 2 that provides resistance to exonuclease activity and/or ligase activity and/or polymerase activity.

More preferably still said first and second oligonucleotides of part iii) also comprise an index feature which is a particular sequence of nucleotides (e.g. GATCT) that enables the origin of pooled sequencing libraries to be determined, in other words, it enables demultiplexing of pooled sequencing libraries. Ideally, the index feature is located between said hybridization site and, where present, said further sequence.

More ideally still, either the first or second oligonucleotide of this second oligonucleotide pair of part iii) comprises two different terminal protective features.

Most preferably, said second oligonucleotide of part iii), reading 5' to 3' comprises a 5' binding and/or protective feature, a further sequence for, optionally, enabling bridge amplification, an index sequence, a hybridization site (RD2 SP) to which a sequencing primer can bind, and a 3' binding and/or protective feature. Preferably, either or both protective features provide resistance to any one or more of the following: exonuclease activity, ligase activity and/or polymerase activity.

In a preferred embodiment of the invention said second oligonucleotide of part iii) is is complementary to said first oligonucleotide of this oligonucleotide pair and comprises a 5' and a 3' protective feature, preferably, providing resistance to any one or more of the following: exonuclease activity, ligase activity and/or polymerase activity. Thus, in certain embodiments the oligonucleotide used to work the invention has a 5' or 3' phosphate group is missing.

Yet more preferably still this second oligonucleotide of part iii) comprises a 3' deoxythymidine triphosphate 'T-tail', to provide a substrate for ligation to 'A-tailed' DNA fragments, ideally with a phosphorothioate linkage whereby resistance to exonuclease activity is conferred.

In a preferred embodiment of the invention said ligation in part i) occurs in situ or in vitro using a cell or tissue suspension and so occurs in the intact cell. Yet more preferably this step is facilitated by permeabilizing the cell or tissue, chemically, electronically, mechanically or physiologically whereby the said oligonucleotide to be ligated can gain access to a DSB site and via its terminal binding feature, e.g. phosphate, it is ligated to the DSB site. Preferably, cells are permeabilized by incubation in lysis buffer. Yet more preferably still said DSB site is arginine tail repaired prior to ligation with said oligonucleotide.

As will be appreciated, ligating said first pair of oligonucleotides/adaptor to the DSB prior to further processing ensures the DSB identified is a true event and not a consequence of the subsequent processing steps and thus representing an artefact of the processing.

In a yet a further preferred embodiment of the invention part i) also includes extracting gDNA from said cells using any conventional means such as an extraction buffer or the like, prior to performing the subsequent steps.

In a preferred embodiment of the invention step ii) comprises fragmenting the gDNA into smaller fragments by any means known in the art, such as sonication or tagmentation.

In yet a further preferred embodiment of the invention said method further comprises an optional step, after part ii) and/or part iv), of removing fragments whose size is less than about 100 bp, more preferably less than about 150 bp, and retaining fragments whose size is greater than about 150 bp. As will be appreciated by those skilled in the art, this step advantageously removes any oligonucleotide strands/dimers that may have formed that would otherwise subsequently contribute to sequence artefacts. This ideally can be undertaken using conventional means such as using a Bioruptor Sonicator, and size selecting using SPRI beads (GC Biotech, CNGS-0005) to remove fragments <150 bp. Or select for fragments in a preferred range such as, without limitation 150-1000 bp, ideally 200-800 bp, more ideally 250-750 bp and yet most preferred 300-500 bp.

In yet a further preferred embodiment of the invention said separating of part v) involves using said binding sequence provided by the oligonucleotide of part i) to bind a partner and so separate the Group A strands of part iv) from any other strands. Typically, a complementary binding strand to said binding sequence provided by the oligonucleotide of part i) is anchored to a substrate and said single strands of nucleic acids flow by, or over, the anchored complementary binding strand.

In yet a further preferred method of the invention part vi) involves bridge amplification where the single strands separated under part v) are clonally amplified on a substrate that has anchored thereon oligonucleotides/binding sites for the binding sequence of the first oligonucleotide of part i) and the further sequence of the second oligonucleotide of part iii). In this way a single strand of the Group A fragments can be bound at both ends on the said substrate to facilitate bridge amplification. Yet more preferably still, said sequencing may be undertaken by synthesis sequencing employing the use of labelled nucleotides each one emitting a characteristic signal that is read as the sequence extends to provide a readout of the sequence information. Typically, a number of strands are sequenced in a parallel process. If preferred the index sequence may be sequenced separately from the DSB, thus providing an indication of the source of the nucleic acid before the DSB is sequenced. Alternatively, the two indices may be sequenced and so read together.

In a particular embodiment, the first pair of oligonucleotides of part i) comprises a first oligonucleotide comprising a sequence according to TCGGTGGTCGCCGTATCATT (SEQ ID NO: 31), and a second oligonucleotide comprising a sequence according to AATGATACGGCGACCACCGA (SEQ ID NO: 34).

In another embodiment, which may be combined with the subject matter of the preceding paragraph, the second pair of oligonucleotides comprises a first oligonucleotide of a sequence that does not comprise a sequence of more than 5, 10, 15, or 20 bases, or does not comprise all 24 bases, of the sequence ATCTCGTATGCCGTCTTCTGCTTG (SEQ ID NO: 30), and a second oligonucleotide comprising a sequence according to CAAGCAGAAGACGGCATACGAGAT (SEQ ID NO: 32).

In a particular embodiment, the first pair of oligonucleotides of part i) comprises a first oligonucleotide comprising a sequence according to ATCTCGTATGCCGTCTTCTGCTTG (SEQ ID NO: 30), and a second oligonucleotide comprising a sequence according to CAAGCAGAAGACGGCATACGAGAT (SEQ ID NO: 32).

In another embodiment, which may be combined with the subject matter of the preceding paragraph, the second pair of oligonucleotides may comprise a first oligonucleotide that does not comprise a sequence of more than 5, 10, or 15 bases, or does not comprise all 20 bases, of the sequence TCGGTGGTCGCCGTATCATT (SEQ ID NO: 31), and a second oligonucleotide comprising a sequence according to AATGATACGGCGACCACCGA (SEQ ID NO: 34).

SEQ ID NOs: 30, 31, 32, and 34 may comprise from 1 to 12, 1 to 10, 1 to 8, 1 to 5, 1 to 3, 2, or 1 modifications such as substitutions, deletions, or insertions. In an embodiment, the modifications are substitutions.

In a further preferred embodiment of the invention said first pair of oligonucleotides of part i) comprises a first oligonucleotide having SEQ ID NO. 1 and a second oligonucleotide having SEQ ID NO. 2 or an oligonucleotide that shares at least 80% identity or homology therewith and more preferably, in increasing order of preference, 81, 82, 83, 84, 85, 86, 87, 88, 89, 90, 91, 92, 93, 94, 95, 96, 97, 98, 99 or 100% identity or homology therewith. The oligonucleotides according to SEQ ID NO: 1 and SEQ ID NO: 2 may comprise from 1 to 12, 1 to 10, 1 to 8, 1 to 5, 1 to 3, 2, or 1 modifications such as substitutions, deletions, or insertions. In an embodiment, the modifications are substitutions. Homology, as used herein, may be referred to as similarity.

In a further preferred embodiment of the invention said first pair of oligonucleotides of part i) comprises a first oligonucleotide of the sequence GATCGGAAGAGC-GTCGTGTAGGGAAAGAGTGT[INDEX]TCGGTGGT-CGCCGTATC ATTC, or comprising 1 to 7, 1 to 6, 1 to 5, 1 to 4, 1 to 3, 2, or 1 modifications such as substitutions, deletions, or insertions. The first pair of oligonucleotides of part i) may further comprise a second oligonucleotide of the sequence AATGATACGGCGACCACCGA[INDEX] ACACTCTTTCCCTACACGACGCTCTTCCG ATCT, or comprising 1 to 7, 1 to 6, 1 to 5, 1 to 4, 1 to 3, 2, or 1 modifications such as substitutions, deletions, or insertions.

In a further preferred embodiment of the invention said first pair of oligonucleotides of part i) comprises a first oligonucleotide of the sequence GATCG-GAAGAGCGTCGTGTAGGGAAAGAGTGT (SEQ ID NO: 37), an index, and TCGGTGGTCGCCGTATCATTC (SEQ ID NO: 38). The first pair of oligonucleotides of part i) may further comprise a second oligonucleotide of the sequence AATGATACGGCGACCACCGA (SEQ ID NO: 34), an index, ACACTCTTTCCCTACACGACGCT-CTTCCGATCT (SEQ ID NO: 39). The index may be any base (n) and may, for instance, be from to 5 to 15 or 6 to 10 base pairs long. SEQ ID NOs: 34, 37, 38, and 39 may comprise from 1 to 7, 1 to 6, 1 to 5, 1 to 4, 1 to 3, 2, or 1 modifications such as substitutions, deletions, or insertions. In an embodiment, the modifications are substitutions.

In a further embodiment of the invention said first pair of oligonucleotides of part i) comprises a first oligonucleotide comprising SEQ ID NO. 3, an index, and the sequence ATCTCGTATGCCGTCTTCTGCTTG (SEQ ID NO: 30). The first pair of oligonucleotides of part i) may further comprise a second oligonucleotide comprising, in 5' to 3' order, the sequence of CAAGCAGAAGACGGCAT-ACGAGAT (SEQ ID NO: 32), an index, and the sequence GTGACTGGAGTTCAGACGTGTGCTCTTCCGATCT (SEQ ID NO: 33). The index may be any base (n) and may, for instance, be from to 5 to 15 or 6 to 10 base pairs long. SEQ ID NOs: 3, 30, 32, and 33 may comprise from 1 to 7, 1 to 6, 1 to 5, 1 to 4, 1 to 3, 2, or 1 modifications such as substitutions, deletions, or insertions. In an embodiment, the modifications are substitutions.

In a further preferred embodiment of the invention said second pair of oligonucleotides of part iii) comprises a first oligonucleotide having SEQ ID NO. 3 and a second oligonucleotide of the sequence CAAGCAGAAGACGGCAT-ACGAGAT[INDEX]GTGACTGGAGTTCA-GACGTGTGCT CTTCCGATCT or an oligonucleotide that shares at least 80% identity or homology therewith and more preferably, in increasing order of preference, 81, 82, 83, 84, 85, 86, 87, 88, 89, 90, 91, 92, 93, 94, 95, 96, 97, 98, 99 or 100% identity or homology therewith. The oligonucleotide according to SEQ ID NO: 3 may comprise from 1 to 7, 1 to 6, 1 to 5, 1 to 4, 1 to 3, 2, or 1 modifications such as substitutions, deletions, or insertions. The oligonucleotide according to CAAGCAGAAGACGGCATACGAGAT[IN-DEX]GTGACTGGAGTTCAGACGTGTGCT CTTCC-GATCT may comprise from 1 to 12, 1 to 10, 1 to 8, 1 to 5, 1 to 3, 2, or 1 modifications such as substitutions, deletions, or insertions. In an embodiment, the modifications are substitutions.

In a further preferred embodiment of the invention said second pair of oligonucleotides of part iii) comprises a first oligonucleotide having SEQ ID NO. 3 and a second oligonucleotide having, in 5' to 3' order, the sequence of CAAGCAGAAGACGGCATACGAGAT (SEQ ID NO: 32), an index, and the sequence GTGACTGGAGTTCA- GACGTGTGCTCTTCCGATCT (SEQ ID NO: 33). The index may be any base (n) and may, for instance, be from to 5 to 15 or 6 to 10 base pairs long. The oligonucleotides may have comprise sequences having 80, 81, 82, 83, 84, 85, 86, 87, 88, 89, 90, 91, 92, 93, 94, 95, 96, 97, 98, 99 or 100% identity or homology with any of SEQ ID NOs: 3, 32, or 33. SEQ ID NOs: 3, 32, or 33 may comprise from 1 to 7, 1 to 6, 1 to 5, 1 to 4, 1 to 3, 2, or 1 modifications such as substitutions, deletions, or insertions. In an embodiment, the modifications are substitutions.

In yet a further preferred embodiment of the invention said second oligonucleotide of said second pair of oligonucleotides of part iii) comprises any one of the following sequences SEQ ID NOs: 4-28, 30-34, 37-39, or 41-42 or an oligonucleotide that shares at least 80% identity or homology therewith and more preferably, in increasing order of preference, 81, 82, 83, 84, 85, 86, 87, 88, 89, 90, 91, 92, 93, 94, 95, 96, 97, 98, 99 or 100% identity or homology therewith. SEQ ID NOs: 4-28, 30-34, 37-39, or 41-42 may comprise from 1 to 12, 1 to 10, 1 to 8, 1 to 5, 1 to 3, 2, or 1 modifications such as substitutions, deletions, or insertions. In an embodiment, the modifications are substitutions.

In a preferred embodiment said sample is a mammalian, ideally human, sample.

According to a further aspect of the invention there is provided a kit of parts, ideally suitable for identifying DNA double-strand breaks (DSBs) in a gDNA sample, comprising
  i) a first pair of oligonucleotides a first one of which comprises a 5' binding feature that enables ligation of said oligonucleotide to a first strand of said DSB, a hybridization site (RD1 SP) to which a first sequencing primer can bind and a binding sequence for separating said DSB from a pool of DSBs; and a second oligonucleotide that is complementary to said first oligonucleotide of this first pair and comprises a 3' binding feature for binding to a second strand of said DSBs; and wherein either or both of said oligonucleotides comprise, respectively, a 3' and/or 5' protective feature; and
  ii) a second pair of oligonucleotides a first one of which comprises a 5' binding feature, that enables ligation of said oligonucleotide to a first strand of said DSB, and a hybridization site (RD2 SP) to which a second sequencing primer can bind; and a second longer oligonucleotide that is in part complementary to said first oligonucleotide of this second pair and comprises a 3' binding feature for binding to a second strand of said DSBs, a sequence complimentary to said hybridization site, and a further sequence which is, optionally, a binding sequence for enabling bridge amplification; and wherein either or both of said oligonucleotides comprise, respectively, a 3' and/or 5' protective feature.

In a preferred kit of the invention, said kit further comprises at least one primer that binds to the first and/or second hybridization sites for the purpose of sequencing.

More preferably still, said kit further comprises fragmenting agents and/or denaturing agents for fragmenting and/or denaturing the nucleic acid into fragments and/or single strands, respectively.

In another, aspect of the invention there is provided a kit of parts, suitable for identifying DNA double-strand breaks (DSBs) in a gDNA sample, comprising
  i) a first pair of oligonucleotides a first one of which comprises a 5' binding feature that enables ligation of said oligonucleotide to a first strand of said DSB and a binding sequence for separating said DSB from a pool of DSBs; and a second oligonucleotide that is complementary to said first oligonucleotide of this first pair; and wherein either or both of said oligonucleotides comprise, respectively, a 3' and/or 5' protective feature; and
  ii) a second pair of oligonucleotides a first one of which is in part complementary to a second oligonucleotide of the second pair; and a second oligonucleotide that comprises a 3' binding feature for binding to a second strand of said DSBs, and a binding sequence for enabling bridge amplification; and wherein either or both of said oligonucleotides comprise, respectively, a 3' and/or 5' protective feature.

In an aspect of the invention there is provided a kit suitable for sample preparation for identifying DSBs in a gDNA sample, comprising
  i) a first pair of oligonucleotides, a first one of which comprises a 5' binding feature that enables ligation of said oligonucleotide to a strand of a double-stranded nucleic acid, and comprises a sequence according to TCGGTGGTCGCCGTATCATT (SEQ ID NO: 31); and a second oligonucleotide that is complementary to said first oligonucleotide of the first pair; and wherein either or both of said oligonucleotides comprise, respectively, a 3' and/or 5' protective feature; and
  ii) a second pair of oligonucleotides, a first one of which does not comprise a sequence of more than 5, 10, 15, or 20 bases, or does not comprise all 24 bases, of the sequence ATCTCGTATGCCGTCTTCTGCTTG (SEQ ID NO: 30); and a second oligonucleotide that comprises a 3' binding feature that enables ligation of said oligonucleotide to a strand of a double-stranded nucleic acid and comprises a sequence according to CAAGCAGAAGACGGCATACGAGAT (SEQ ID NO: 32); and wherein either or both of said oligonucleotides comprise, respectively, a 3' and/or 5' protective feature.

In another aspect of the invention there is provided a kit suitable for sample preparation for identifying DSBs in a gDNA sample, comprising
  i) a first pair of oligonucleotides, a first one of which comprises a 5' binding feature that enables ligation of said oligonucleotide to a strand of a double-stranded nucleic acid, and comprises a sequence according to ATCTCGTATGCCGTCTTCTGCTTG (SEQ ID NO: 30); and a second oligonucleotide that is complementary to said first oligonucleotide of the first pair and optionally comprises a 3' binding feature; and wherein either or both of said oligonucleotides comprise, respectively, a 3' and/or 5' protective feature; and
  ii) a second pair of oligonucleotides, a first one of which does not comprise a sequence of more than 5, 10, or 15 bases, or does not comprise all 20 bases, of the sequence TCGGTGGTCGCCGTATCATT (SEQ ID NO: 31), and optionally comprises a 5' binding feature; and a second oligonucleotide that comprises a 3' binding feature that enables ligation of said oligonucleotide to a strand of a double-stranded nucleic acid and comprises a sequence according to AATGATACGGCGACCACCGA (SEQ ID NO: 34); and wherein either or both of said oligonucleotides comprise, respectively, a 3' and/or 5' protective feature.

SEQ ID NOs: 30, 31, 32, and 34 may comprise from 1 to 12, 1 to 10, 1 to 8, 1 to 5, 1 to 3, 2, or 1 modifications such as substitutions, deletions, or insertions. In an embodiment, the modifications are substitutions.

The second oligonucleotide of part i) may comprise a 3' binding feature and the first oligonucleotide of part ii) may comprise a 5' binding feature. The first oligonucleotides of the first and second pairs of oligonucleotides may include hybridization sites (RD1 SP) to which sequencing primers can bind.

According to a further aspect of the invention there is provided a double strand adaptor, ideally for identifying DNA double-strand breaks (DSBs) in a nucleic acid sample, such as a gDNA sample, comprising:

a first oligonucleotide strand comprising a 5' binding feature that enables ligation of said oligonucleotide to a first strand of said DSB, a hybridization site (RD1 SP) to which a sequencing primer can bind and a binding sequence for separating said DSB from a pool of DSBs; and a second oligonucleotide strand that is complementary to said first oligonucleotide and comprises a 3' binding feature for binding to a second strand of said DSBs; and wherein either or both of said oligonucleotides comprise, respectively, a 3' and/or 5' protective feature.

According to a further aspect of the invention there is provided a double strand adaptor, ideally for identifying DNA double-strand breaks (DSBs) in a nucleic acid sample, such as a gDNA sample, comprising:

a first oligonucleotide strand comprising a 5' binding feature, that enables ligation of said oligonucleotide to a first strand of said DSB, and a hybridization site (RD2 SP) to which a sequencing primer can bind; and a second longer oligonucleotide strand that is in part complementary to said first oligonucleotide and comprises a 3' binding feature for binding to a second strand of said DSBs, a sequence complimentary to said hybridization site, and a further sequence, which is, optionally, a binding sequence for enabling bridge amplification; and wherein either or both of said oligonucleotides comprise, respectively, a 3' and/or 5' protective feature.

According to a further aspect of the invention there is provided a double strand adaptor, suitable for identifying DNA double-strand breaks (DSBs) in a nucleic acid sample, such as a gDNA sample, comprising:

a first oligonucleotide strand which does not comprise a sequence of more than 5, 10, 15, or 20 bases, or does not comprise all 24 bases, of the sequence ATCTCGTATGCCGTCTTCTGCTTG (SEQ ID NO: 30); and a second oligonucleotide that comprises a 3' binding feature that enables ligation of said oligonucleotide to a strand of a double-stranded nucleic acid and comprises a sequence according to CAAGCAGAAGACGGCATACGAGAT (SEQ ID NO: 32); and wherein either or both of said oligonucleotides comprise, respectively, a 3' and/or 5' protective feature. The first oligonucleotide may comprise a 5' binding feature.

According to a further aspect of the invention there is provided a double strand adaptor, suitable for identifying DNA double-strand breaks (DSBs) in a nucleic acid sample, such as a gDNA sample, comprising:

a first oligonucleotide strand which does not comprise a sequence of more than 5, 10, or 15 bases, or does not comprise all 20 bases, of the sequence TCGGTGGTCGCCGTATCATT (SEQ ID NO: 31); and a second oligonucleotide that comprises a 3' binding feature that enables ligation of said oligonucleotide to a strand of a double-stranded nucleic acid and comprises a sequence according to AATGATACGGCGACCACCGA (SEQ ID NO: 34); and wherein either or both of said oligonucleotides comprise, respectively, a 3' and/or 5' protective feature. The first oligonucleotide may comprise a 5' binding feature.

In an aspect of the invention, there is provided a method of sample preparation for identifying DSBs in a nucleic acid sample, wherein the preparation comprises modifying DSB-associated nucleic acids to be suitable for binding to a substrate comprising immobilised primers, the method comprising:

a) providing a sample comprising a plurality of nucleic acids;

b) exposing the plurality of nucleic acids to a first adaptor under conditions conducive to ligation, wherein the first adaptor comprises an oligonucleotide capable of being ligated to a 3' terminus of a strand of a DSB and which comprises a sequence that is capable of binding to a primer immobilised to the substrate by hybridisation;

c) fragmenting the plurality of nucleic acids; and d) exposing the plurality of nucleic acids to a second adaptor under conditions conducive to ligation, wherein the second adaptor comprises an oligonucleotide capable of being ligated to a 5' terminus of a strand at a break induced by fragmentation, but is not capable of being ligated to the first adaptor, and which does not comprise a sequence that is capable of binding to a primer immobilised to the substrate by hybridisation. The oligonucleotide of the second adaptor capable of being ligated to a 5' terminus of a strand at a break induced by fragmentation may comprise a sequence identical to a region of a second primer.

In some embodiments, the nucleic acids within the sample comprising a plurality of nucleic acids are double stranded during steps b) to d). In other embodiments, the nucleic acids may be single stranded during steps b) to d). In yet further embodiments, the nucleic acids may be double stranded for some steps, and single stranded for others (e.g. see FIG. 16). In embodiments involving the ligation of a double-stranded adaptor to a single-stranded nucleic acid, the adaptor may comprise a "splint oligo". The splint oligo may comprise random nucleotides, such as 6-8 random nucleotides, and be positioned at the 3' end of the oligonucleotide of the adaptor that does not ligate to the nucleic acid sample. Splint oligos may aid in the ligation process.

In an embodiment, there is provided a method of sample preparation for identifying DSBs in a nucleic acid sample, wherein the preparation comprises modifying DSB-associated nucleic acids to be suitable for binding to a substrate comprising a first immobilised primer and to be suitable for amplification comprising the use of said first immobilised primer and a second primer, the method comprising:

a) providing a sample comprising a plurality of nucleic acids;

b) exposing the plurality of nucleic acids to a first adaptor under conditions conducive to ligation, wherein the first adaptor comprises an oligonucleotide capable of being ligated to a 3' terminus of a strand of a DSB and which comprises a sequence that is capable of binding to a primer immobilised to the substrate by hybridisation;

c) fragmenting the plurality of nucleic acids; and d) exposing the plurality of nucleic acids to a second adaptor under conditions conducive to ligation, wherein the second adaptor comprises an oligonucleotide capable of being ligated to a 5' terminus of a strand at a break induced by fragmentation, but is not capable of being ligated to the first adaptor, and which comprises a sequence identical to a region of the second primer.

A nucleic acid sample suitable for amplification comprising the use of a first immobilised primer and a second primer, is a sample capable of being amplified by a primer of the same sequence as the first immobilised primer and a primer of the same sequence as the second primer. Suitability for amplification may be determined in solution.

In some embodiments, the second primer is not immobilised to the substrate. For instance, the substrate may be a bead and amplification may take place via bead-emulsion amplification.

In other embodiments, the second primer is immobilised to the substrate. For example, the substrate may be a flow cell and amplification may take place via bridge amplification.

In some embodiments, the adaptors are single-stranded oligonucleotides.

In other embodiments, the adaptors comprise a first and a second oligonucleotide that are at least partially complementary. In such embodiments, the first adaptor pair is capable of being ligated to at least a 3' terminus of a strand of a DSB, and the first adaptor pair comprises first and second oligonucleotides that are at least partially complementary, wherein the first oligonucleotide is ligatable to a 3' terminus and comprises a sequence that is capable of binding, by hybridisation, to a primer immobilised to the substrate. In addition, in such embodiments the second adaptor pair is capable of being ligated to at least a 5' terminus of a strand at a break induced by fragmentation but is not capable of being ligated to the first oligonucleotide of the first adaptor pair, wherein the second adaptor comprises first and second partially complementary oligonucleotides, wherein the first oligonucleotide is ligatable to a 5' terminus and comprises a sequence identical to a region of the second primer, and the second oligonucleotide does not comprise a sequence that is complementary to said sequence identical to a region of the second primer.

Thus, in an embodiment, there is provided a method of sample preparation for identifying DNA DSBs in a nucleic acid sample, wherein the preparation comprises modifying DSB-associated nucleic acids to be suitable for binding to a substrate comprising a first immobilised primer and to be suitable for amplification comprising the use of said first immobilised primer and a second primer, the method comprising, the method comprising:
a) providing a sample comprising a plurality of nucleic acids;
b) exposing the plurality of nucleic acids to a first adaptor pair under conditions conducive to ligation, wherein the first adaptor pair is capable of being ligated to at least a 3' terminus of a strand of a DSB, and wherein the first adaptor pair comprises first and second oligonucleotides that are at least partially complementary, and the first oligonucleotide is ligatable to a 3' terminus and comprises a sequence that is capable of binding to a primer immobilised to the substrate by hybridisation;
c) fragmenting the plurality of nucleic acids; and
d) exposing the plurality of nucleic acids to a second adaptor pair under conditions conducive to ligation, wherein the second adaptor pair is capable of being ligated to at least a 5' terminus of a strand at a break induced by fragmentation but is not capable of being ligated to the first oligonucleotide of the first adaptor pair, wherein the second adaptor comprises first and second partially complementary oligonucleotides, wherein the first oligonucleotide is ligatable to a 5' terminus and comprises a sequence identical to a region of the second primer, and the second oligonucleotide does not comprise a sequence that is complementary to said sequence identical to a region of the second primer.

In some embodiments, the substrate comprises a first immobilised primer and a second immobilised primer. The immobilised primers may, in some embodiments, be suitable for acting as primers during bridge amplification.

Thus, in an embodiment, there is provided a method of sample preparation for identifying DNA DSBs in a nucleic acid sample, wherein the preparation comprises modifying DSB-associated nucleic acids to be suitable for binding to a substrate comprising a first and a second immobilised primer, the method comprising:
a) providing a sample comprising a plurality of nucleic acids;
b) exposing the plurality of nucleic acids to a first adaptor under conditions conducive to ligation, wherein the first adaptor comprises an oligonucleotide capable of being ligated to a 3' terminus of a strand of a DSB and which comprises a sequence that is capable of binding to the first immobilised primer by hybridisation;
c) fragmenting the plurality of nucleic acids; and
d) exposing the plurality of nucleic acids to a second adaptor under conditions conducive to ligation, wherein the second adaptor comprises an oligonucleotide capable of being ligated to a 5' terminus of a strand at a break induced by fragmentation, but is not capable of being ligated to the first adaptor, and which comprises a sequence identical to a region of the second immobilised primer.

In other embodiments, the adaptors are adaptor pairs comprising a first and a second oligonucleotide that are at least partially complementary. Thus, there is provided a method of sample preparation for identifying DNA DSBs in a nucleic acid sample, wherein the preparation comprises modifying DSB-associated nucleic acids to be suitable for binding to a substrate comprising a first and a second immobilised primer, the method comprising:
a) providing a sample comprising a plurality of nucleic acids;
b) exposing the plurality of nucleic acids to a first adaptor pair under conditions conducive to ligation, wherein the first adaptor pair is capable of being ligated to at least a 3' terminus of a strand of a DSB, and wherein the first adaptor pair comprises first and second oligonucleotides that are at least partially complementary, and wherein the first oligonucleotide is ligatable to a 3' terminus and comprises a sequence that is capable of binding to the first immobilised primer by hybridisation;
c) fragmenting the plurality of nucleic acids; and
d) exposing the plurality of nucleic acids to a second adaptor pair under conditions conducive to ligation, wherein the second adaptor pair is capable of being ligated to at least a 5' terminus of a strand at a break induced by fragmentation but is not capable of being ligated to the first oligonucleotide of the first adaptor pair, wherein the second adaptor comprises first and second partially complementary oligonucleotides and the oligonucleotide that is ligatable to a 5' terminus comprises a sequence identical to a region of the second immobilised primer and wherein the other oligonucleotide does not comprise a sequence that is complementary to said sequence identical to a region of the second immobilised primer.

As discussed herein, in some embodiments the nucleic acids within the sample may be maintained as double-stranded molecules during steps a) to d). As such, in particular embodiments, the methods may further comprise:

denaturing the plurality of double-stranded nucleic acids to form a plurality of single-stranded nucleic acids. This may be "step e)" in some embodiments.

In a particular embodiment, the methods may further comprise:

contacting the plurality of single-stranded nucleic acids with the substrate comprising immobilised primers under conditions suitable for hybridisation of the immobilised primers to complementary nucleic acids. This may be "step f)" in some embodiments.

The features disclosed in connection with step i) of the methods disclosed herein are also appliable to step b). The features disclosed in connection with step ii) of the methods disclosed herein are also appliable to step c). The features disclosed in connection with step iii) of the methods disclosed herein are also appliable to step d). The features disclosed in connection with step iv) of the methods disclosed herein are also appliable to step e). The features disclosed in connection with step v) of the methods disclosed herein are also appliable to step f).

The substrate may be a solid surface such as a surface of a flow cell, a bead, a slide, or a membrane. In particular, the substrate may be a flow cell. The substrate may be a patterned or a non-patterned flow cell. The substrate may comprise glass, quartz, silica, metal, ceramic, or plastic. The substrate surface may comprise a polyacrylamide matrix or coating.

As used herein, the term "flow cell" is intended to have the ordinary meaning in the art, in particular in the field of sequencing by synthesis. Exemplary flow cells include, but are not limited to, those used in a nucleic acid sequencing apparatus such as flow cells for the Genome Analyzer®, MiSeq®, NextSeq®, HiSeq®, or NovaSeq® platforms commercialised by Illumina, Inc. (San Diego, Calif.); or for the SOLiD™ or Ion Torrent™ sequencing platform commercialized by Life Technologies (Carlsbad, Calif.). Exemplary flow cells and methods for their manufacture and use are also described, for example, in WO2014/142841A1; U.S. Pat. App. Pub, No. 2010/0111768 A1 and U.S. Pat. No. 8,951,781.

The substrate may comprise immobilised primers, for instance two types of primer which together can act as forward and reverse primers for bridge amplification. Immobilisation to a substrate means that the primer is bound to the substrate even under conditions that would denature double-stranded nucleic acids. For instance, the primer may be covalently bound to the substrate. The primers are oriented such that the 5' end is proximal and the 3' end is distal to the point of immobilisation. Such arrangements are standard in the art.

The steps may be performed in the order: step c), step d), and then step b). This order is particularly relevant to embodiments where a DSB is potentially induced in the sample, as opposed to embodiments for the detection of a pre-existing DSB. With reference to statements of the invention featuring steps defined by roman numerals, the steps may be performed in the order: step ii), step iii), and then step i). In such embodiments, the DSB may be induced after the ligation of the second adaptor and before ligation of the first adaptor. For example, see FIG. 13. The induction of the DSB may comprise exposing the sample to conditions capable of causing or suspected of being capable of causing a DSB.

In embodiments wherein step d) is performed before step b), the adaptors of step d) may comprise 3' and/or 5' protective features to prevent ligation of the adaptors of step b) to those of step d). The protective features may render the first adaptor to be not capable of being ligated to the second adaptor. In such embodiments, the second adaptor remains incapable of being ligated to the first adaptor because the ligation takes place before the first adaptor is present.

In some embodiments, the steps are performed in the order step b), step c), and step d), wherein the step b) is performed in a cell or in situ. In other embodiments, the steps are performed in the order step c), step d), and then step b), wherein step c) is performed in vitro after isolation of the nucleic acid sample.

Thus, in an embodiment, there is provided a method of sample preparation for identifying DSBs in a nucleic acid sample, wherein the preparation comprises modifying DSB-associated nucleic acids to be suitable for binding to a substrate comprising immobilised primers, the method comprising, in order:

a) providing a sample comprising a plurality of nucleic acids;
c) fragmenting the plurality of nucleic acids;
d) exposing the plurality of nucleic acids to a second adaptor under conditions conducive to ligation, wherein the second adaptor comprises an oligonucleotide capable of being ligated to a 5' terminus of a strand at a break induced by fragmentation, and which does not comprise a sequence that is capable of binding to a primer immobilised to the substrate by hybridisation; optionally comprising a sequence identical to a region of a second primer; and
b) exposing the plurality of nucleic acids to a first adaptor under conditions conducive to ligation, wherein the first adaptor comprises an oligonucleotide capable of being ligated to a 3' terminus of a strand of a DSB, but is not capable of being ligated to the second adaptor, and which comprises a sequence that is capable of binding to a primer immobilised to the substrate by hybridisation.

In step a), the sample comprising a plurality of double-stranded nucleic acids may be any DNA sample capable of comprising DSBs, such as gDNA.

For any of the methods disclosed herein, the sample may contain DSBs or may have been treated in a manner that might or does introduce DSBs.

For instance, the methods disclosed herein may be used to detect DNA damage or changes that are confined to a single strand. Thus, the methods disclosed herein may be for the detection and/or quantification of a feature of interest within a nucleic acid sample. As an example, a lesion in one strand of double-stranded DNA may be enzymatically converted into a DSB, which can then be detected by the methods disclosed herein.

In some examples, the lesion may be a single-strand break. In other examples, the lesion is a base change in a nucleic acid sample. For instance, the methods disclosed herein may be for the detection of CRISPR/Cas induced base editing, such as a cytosine base editor or an adenosine base editor. Such edits may be converted into DSBs and detected as disclosed herein. FIG. 17 and FIG. 18 illustrate exemplary embodiments.

Thus, in an embodiment, the method comprises providing a sample comprising a plurality of nucleic acids comprising or suspected of comprising a feature of interest or a lesion; and exposing the sample to conditions capable of converting the feature of interest or lesion into a DSB.

For such embodiments, the method may be in the order: conversion of the lesion into a DSB, b), c), and d); or may be in the order: c), d), conversion of the lesion into a DSB, and b).

In other embodiments, the sample may have been treated with a nuclease, such as a transcription activator-like effector nuclease (TALEN), a CRISPR/Cas endonuclease, a zinc finger nuclease, a meganuclease, or any restriction endonuclease, and the methods may be for the detection of off-target effects. The sample may be been treated with an agent, such as a potential therapeutic agent, to determine if said agent is capable of causing DSBs or off-target DSBs.

The methods disclosed herein may be used to identify sites of protein binding to a nucleic acid. For instance, a sample may be contacted with a protein-binding agent, such as an antibody, specific for a protein-of-interest, wherein the protein-of-interest is potentially bound to DNA. The DNA may be a sample that has been contacted with the protein-of-interest. The protein-binding agent may be directly or indirectly associated with a nuclease, hence forming a DSB at any site at which the protein of interest is bound. Any DSBs may then be detected by the methods disclosed herein. The methodology may be Cleavage Under Targets and Release Using Nuclease (CUT&RUN) methods. As such, the method may comprise: step a); contacting the sample with a protein-of-interest; contacting the sample with an nuclease capable of directly or indirectly associating with the protein-of-interest to form a DSB in nucleic acids to which the protein is bound; step b), step c), and then step d). This order is particularly useful for embodiments wherein the method up to step b) is performed in a cell. Alternatively, the method may comprise: step a); step c); step d); contacting the sample with a protein-of-interest; contacting the sample with an nuclease capable of directly or indirectly associating with the protein-of-interest to form a DSB in nucleic acids to which the protein is bound; and then step b). This order is particularly useful for in vitro embodiments.

In other embodiments, the DSB may be deliberately induced in a known or target site. For instance, a targeted nuclease, such as a CRIPSR/Cas or a TALEN, may be used to induce a DSB in a sequence of interest such that the methods of the invention can be used to isolate said sequence of interest for further analysis. The sequence of interest may be specific genes, the whole exome, or a specific locus in the genome. As such, in an embodiment the methods comprise contacting the sample with a nuclease capable of the targeted induction of a DSB in a sequence of interest.

The methods of the invention may be for the detection of viral or bacterial insertion events or DNA damage caused by viral or bacterial insertion events. These events are measurable by virtue of the unique genetic sequences associated with bacteria and viruses that would be inserted into the genome. The methods of the invention can therefore reveal these sites of foreign DNA insertion, which can occur via a DSB intermediate structure.

In other embodiment, the methods disclosed herein may be used to assess risks associated with a therapeutic agent, such as a gene therapy. For instance, the methods disclosed herein may be applied to a sample taken from a patient, wherein the sample has been treated with the therapeutic agent, in order to determine the risk, nature, or frequency of off-target effects for said patient. Thus, the methods disclosed herein may be useful for personalised medicine by providing a patient-specific pattern of DSBs, and their frequency, as induced by an agent of interest. As such, in an embodiment the methods may comprise obtaining a sample from a subject and exposing said sample to an agent, such as a therapeutic agent. The method may comprise determining the nature and/or frequency of any lesions or DSBs in the sample after the exposure. The order of the steps of the invention may be any as described herein.

The methods disclosed herein may be used for detecting contamination of a sample by any agent capable of causing DSBs.

The methods disclosed herein may be used to measure the stability of artificially assembled or synthetic genomes.

The methods disclosed herein may be used for Next-Generation Risk Assessment (NGRA) in genetic toxicology. NGRA is defined as an exposure-led, hypothesis-driven risk assessment approach that integrates new approach methodologies (NAMs) to assure safety without the use of animal testing. DSBs are a direct measurement of genotoxic exposure and can quantified by the methods of then invention. Hence, the methods of the invention may be used for risk assessments requiring the quantification of genotoxic exposure.

In summary, the sample of nucleic acid suspected of containing DSBs may contain said DSBs due to naturally occurring DNA damage, due to treatment with a potentially DSB causing agent, due to deliberate induction of a DSB at a site of interest, or for any other reason.

In step b) the conditions enable the ligation of the first adaptor to a DSB. The first adaptor comprises an oligonucleotide capable of ligating to the 3' terminus of a stand of a DSB and may also comprise another oligonucleotide capable of ligating to the 5' terminus of a strand of a DSB. As such, the first adaptor is covalently linked to the DSB. The ligation may be direct or indirect. For instance, the ligation may be to additional nucleotides introduced at the DSB. Alternatively, an oligonucleotide or pair of oligonucleotides may be ligated to the DSB and the first adaptor may be ligated to the said oligonucleotide or oligonucleotides. The methods of ligation may be any as disclosed herein. The two oligonucleotides of the first adaptor pair may be completely complementary.

The first and/or second oligonucleotides of the first adaptor pair may comprise a 3' and/or a 5' protective feature. These protective features may be any as disclosed herein, particularly any disclosed in connection with the first pair of oligonucleotides discussed in relation to step i) of the methods disclosed herein.

The first and/or second oligonucleotides of the first adaptor pair may comprise any features disclosed in connection with the first pair of oligonucleotides discussed in relation to step i) of the methods disclosed herein. In particular, the first adaptor pair may include or not include the sequences disclosed in connection with the first pair of oligonucleotides discussed in relation to step i).

The first adaptor includes an oligonucleotide that is ligatable to a 3' terminus and comprises a sequence that is capable of binding to an immobilised primer by hybridisation. This means that, when a ligated first adaptor pair is denatured into single strands, one strand is complementary to a primer immobilised to the substrate. The adaptor includes a sufficient length of complementary sequence to enable binding that is not released during washing or polymerisation steps. The length of the complementary region may be 5, 10, 15, 20, 21, 24, or more bases. Alternatively, the complementary region may include 5, 10, 15, 20, 21, 24, or more complementary bases.

Step c) may comprise any method of fragmentation as discussed herein.

In step d) the conditions enable the ligation of the nucleic acids to a second adaptor. The second adaptor comprises an oligonucleotide capable of ligating to a 5' terminus at a fragmentation site and may comprise an oligonucleotide capable of ligating to a 3' terminus at a fragmentation site. The methods of ligation may be any as disclosed herein.

Figure 12A:
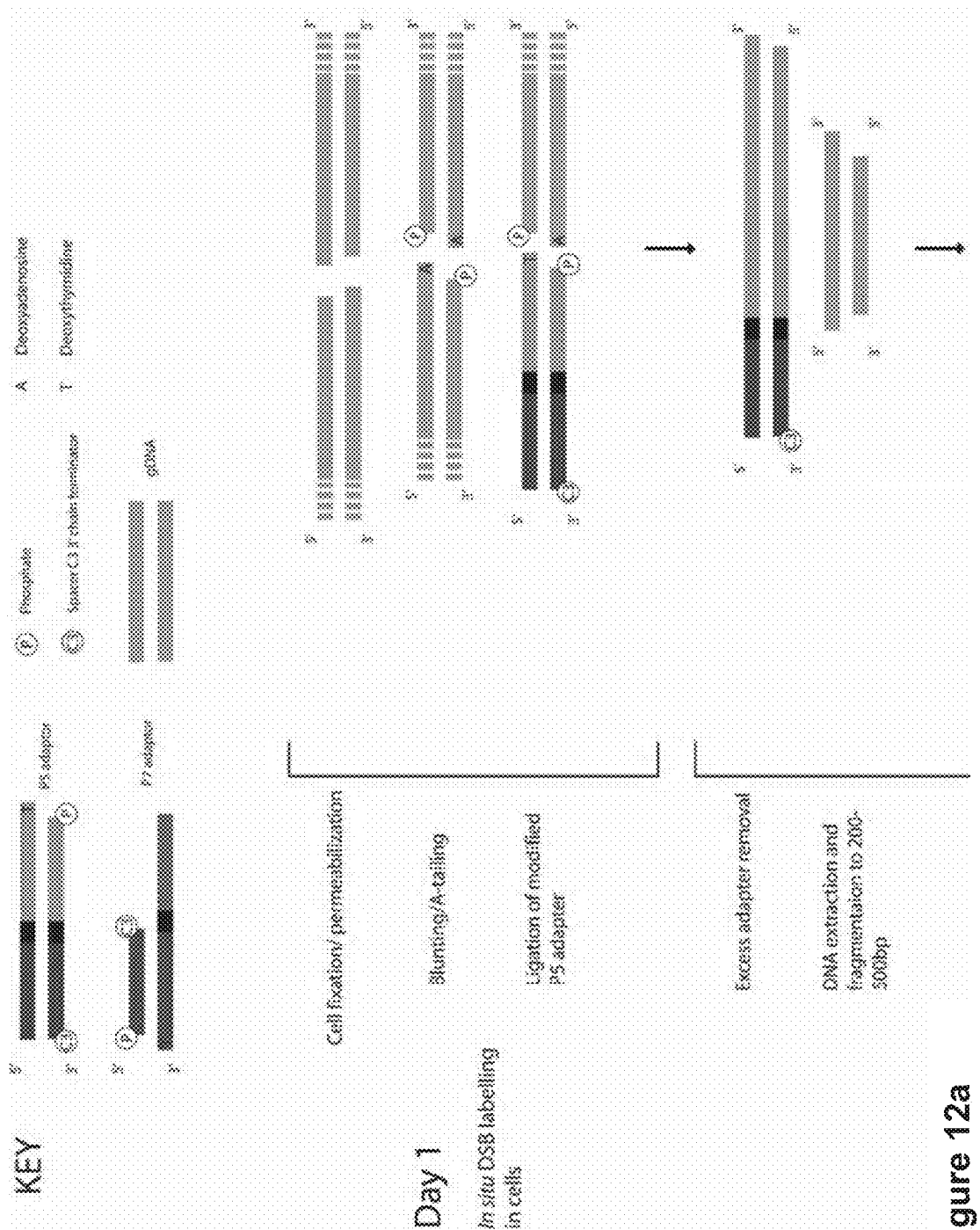
FIG. 12a and FIG. 12b. Exemplary embodiment indicating exemplary chemical modifications.
Figure 12B:
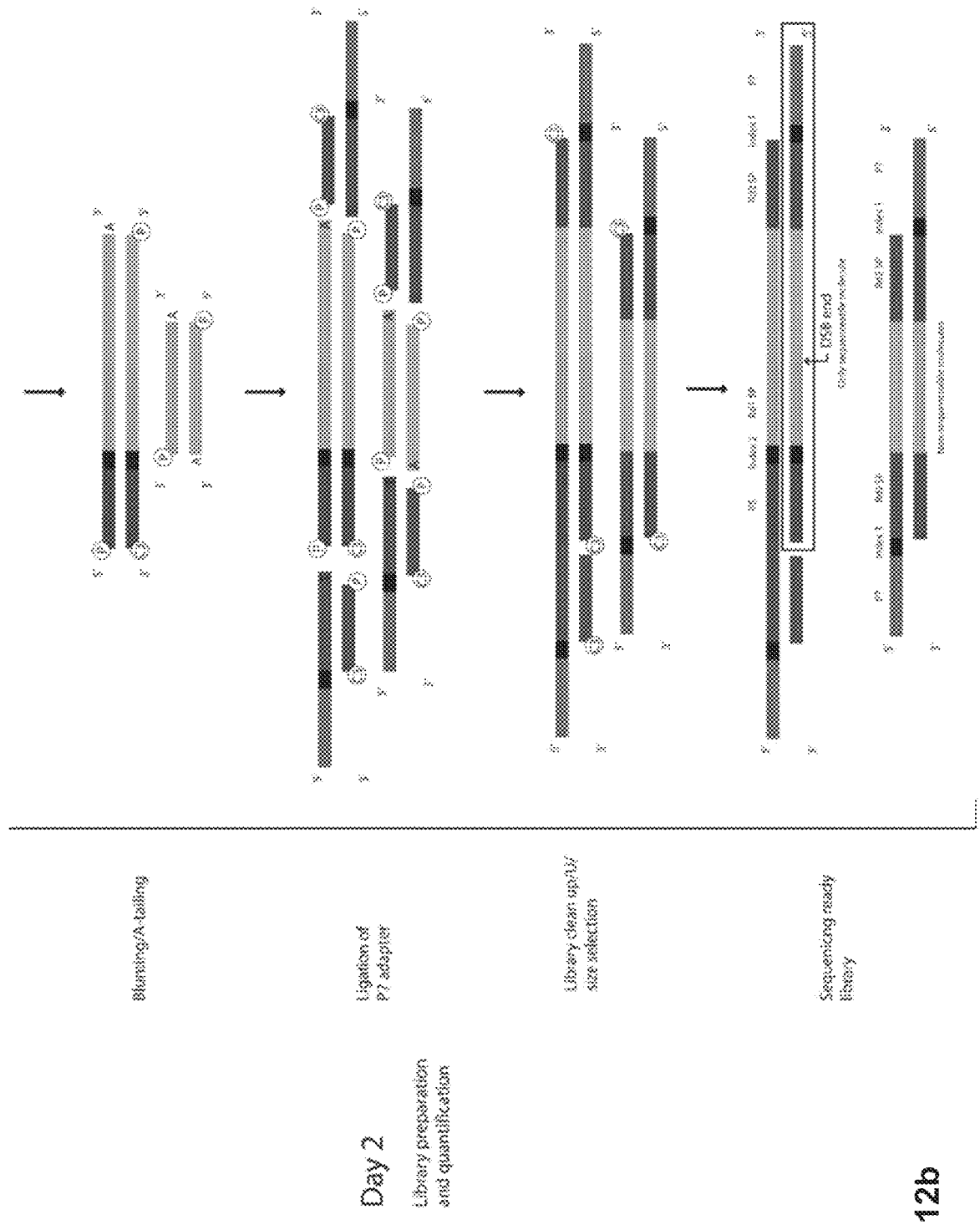

The second adaptor is not capable of ligating to the first adaptor. In a particular embodiment, this prevention is due to the inclusion of a 3' protective feature on the first adaptor. In relevant embodiments, this prevention is due to the inclusion of 5' and/or 3' protective features on the first adaptor pair. In particular, the first oligonucleotide of the first adaptor (i.e. the oligonucleotide capable of binding to a 3' terminus) may comprise a 3' protective feature, such as a spacer C3 3' chain terminator, to prevent adaptor ligation to this strand (see FIG. 12).

The first and/or second oligonucleotides of the second adaptor pair may comprise a 3' and/or a 5' protective feature. These protective features may be any as disclosed herein, particularly any disclosed in connection with the second pair of oligonucleotides discussed in relation to step iii) of the methods disclosed herein.

In embodiments wherein step d) is performed before step b), the first and/or second oligonucleotides of the second adaptor pair may comprise a 3' and/or a 5' protective feature, and at least one protective feature may to prevent ligation of the adaptors of step b) to those of step d). For instance, the oligonucleotide of the second adaptor capable of binding to a 3' terminus may comprise a 3' protective feature, such as a spacer C3 3' chain terminator.

The first and/or second oligonucleotides of the second adaptor pair may comprise any features disclosed in connection with the second pair of oligonucleotides discussed in relation to step iii) of the methods disclosed herein. In particular, the second adaptor pair may include or not include the sequences disclosed in connection with the second pair of oligonucleotides discussed in relation to step iii).

The second adaptor pair may be introduced by tagmentation. As such, the fragmentation and ligation of the second adaptor may be the same step. For instance, steps c) and d) may be combined.

The second adaptor includes an oligonucleotide that is ligatable to a 5' terminus and which comprises a sequence identical to at least part of a primer immobilised to the substrate. Hence, when this oligonucleotide acts as a template during polymerisation, the new strand will include a sequence which is capable of hybridising to said primer. Thus, the length of the relevant region of the adaptor sequence and the relevant region of the primer should be adequate for this function. The length of the identical region may be 5, 10, 15, 20, 21, 24, or more bases. The other oligonucleotide within the second adaptor does not include a sequence complementary to this so-called identical region. As such, the second adaptor is not capable of binding to the substrate via hybridisation.

After step f), the methods may further comprise contacting any hybridised nucleic acid with a polymerase under conditions suitable for the extension of the immobilised primer to synthesise a nucleic acid which is a chain of nucleotides that are complementary to the hybridised nucleic acid. The newly formed nucleic acid may then be amplified. In some embodiments, the primer for amplification is also immobilised to the substrate and may, for instance, be suitable for bridge amplification. This process is known in the art and forms clonal clusters of nucleic acids. In other embodiments, the primer for implication may be in solution, for instance for some embodiments wherein the substrate is bead. The amplified nucleic acids may then be sequenced in the usual way, for instance by sequencing-by-synthesis. The adaptors may comprise a site for the binding of a sequencing primer to assist this process. The adaptors may also comprise an index as disclosed herein.

Thus, in an embodiment, the methods may further comprise:
  g) obtaining sequence information for any nucleic acids that hybridised to the substrate in step f).

Methods including step g) may be referred to as methods for identifying DNA DSBs in a nucleic acid sample.

The features disclosed in connection with step vi) of the methods disclosed herein are also appliable to step g).

In any embodiments of products or methods comprising an oligonucleotide comprising AATGATACGGCGAC-CACCGA (SEQ ID NO: 34), or variants thereof, the oligonucleotide may comprise AATGATACGGCGAC-CACCGAGATCTACAC (SEQ ID NO: 41), or variants as defined for SEQ ID NO: 34. In any embodiments of products or methods comprising an oligonucleotide comprising SEQ ID NO: 31 or comprising no more than 5, 10, 15, or 20 bases of the sequence TCGGTGGTCGCCGTATCATT (SEQ ID NO: 31), the oligonucleotide may comprise SEQ ID NO: 38 or 42, or may comprise no more than 5, 10, 15, 20, 25, or 29 bases of the sequence GTGTA-GATCTCGGTGGTCGCCGTATCATT (SEQ ID NO: 42), or no more than 5, 10, 15, or 19 bases of the sequence TCGGTGGTCGCCGTATCATTC (SEQ ID NO: 38).

Figure 16:
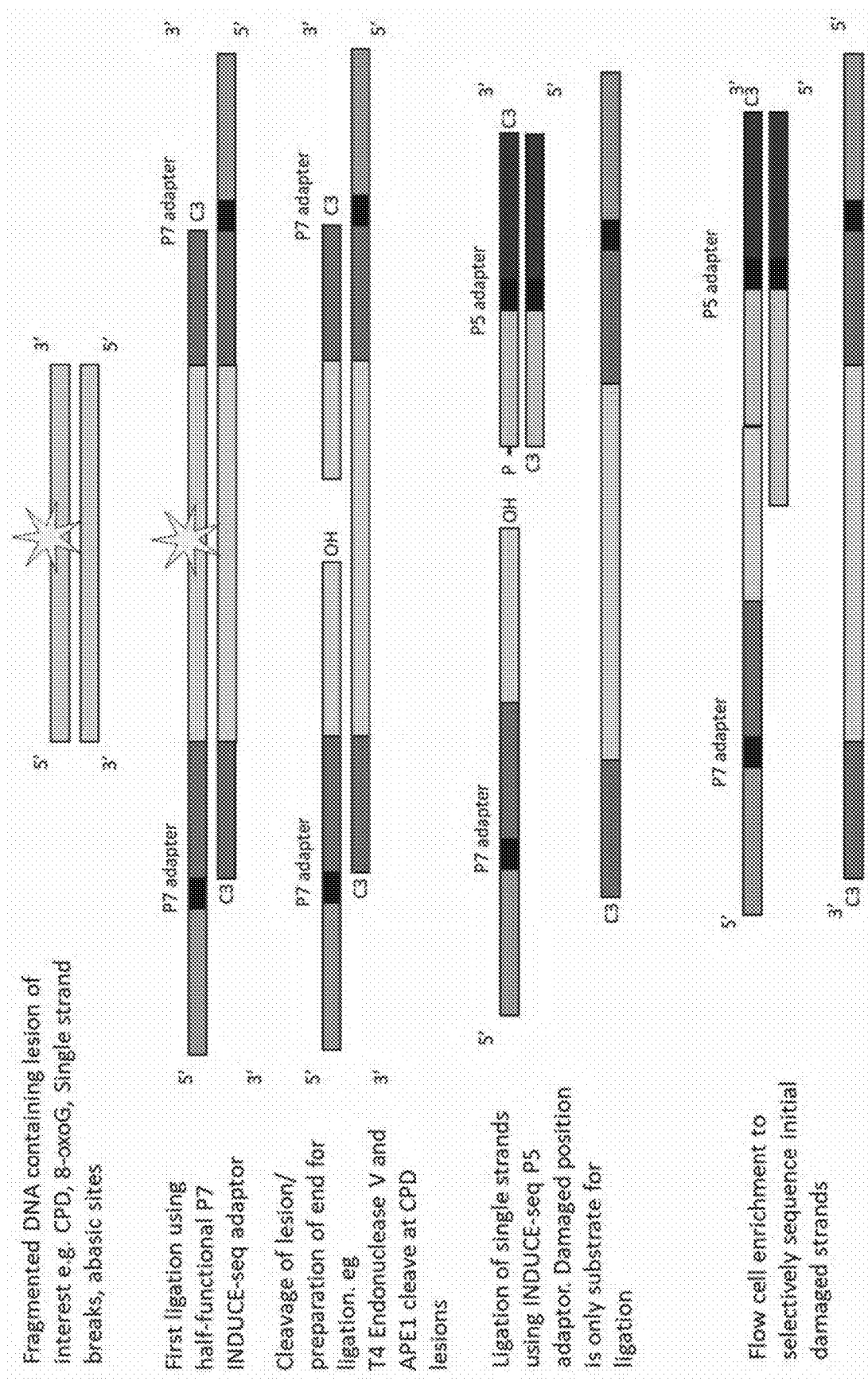
FIG. 16. Exemplary embodiment of detecting a DNA lesion affecting one strand. This embodiment involves the ligation of the half functional adaptor before the fully functional adaptor.

FIG. 16 discloses an embodiment wherein a feature of interest, such as a lesion in a single strand of double-stranded DNA, is identified by the methods of the invention. The feature of interest may be any feature capable of being specifically cleaved. For instance, any feature which would result in the cleavage of a single strand of double-stranded DNA at the site of the feature of interest. The feature of interest may be, for instance, a cyclobutane pyrimidine dimer (CPD), 8-oxoguanine, an abasic site, and any combination thereof. In embodiments, the strand of DNA comprising the feature of interest may be cleaved, and the double-stranded sample denatured, to result in a 3' terminus to which an adaptor may be ligated.

Thus, in an aspect of the invention, there is provided a method of sample preparation for identifying a feature of interest in a nucleic acid sample, wherein the preparation comprises modifying nucleic acids associated with a feature of interest to be suitable for binding to a substrate comprising immobilised primers, the method comprising:
  a) providing a sample comprising a plurality of nucleic acids, exposing the plurality of nucleic acids to conditions capable of cleaving at least one strand of a nucleic acid at a feature of interest, and denaturing the plurality of nucleic acids into single-stranded nucleic acids;
  b) exposing the plurality of nucleic acids to a first adaptor under conditions conducive to ligation, wherein the first adaptor comprises an oligonucleotide capable of being ligated to a 3' terminus of a strand of a cleavage site and which comprises a sequence that is capable of binding to a primer immobilised to the substrate by hybridisation;
  c) fragmenting the plurality of nucleic acids; and
  d) exposing the plurality of nucleic acids to a second adaptor under conditions conducive to ligation, wherein the second adaptor comprises an oligonucleotide capable of being ligated to a 5' terminus of a strand at a break induced by fragmentation, but is not capable of being ligated to the first adaptor, and which does not comprise a sequence that is capable of binding to a primer immobilised to the substrate by hybridisation. The oligonucleotide of the second adaptor capable of being ligated to a 5' terminus of a strand at a break induced by fragmentation may comprise a sequence identical to a region of a second primer.

All features disclosed in connection with the methods of identifying DNA DSBs are also relevant to the methods for identifying a feature of interest. In particular, steps b), c) and d) of the method of sample preparation for identifying a feature of interest in a nucleic acid sample may be the same as steps b), c), and d) as disclosed for the method of sample preparation for identifying DNA DSBs in a nucleic acid sample. The adaptors may be the same as disclosed for identifying DSBs and the methods may be for preparing a library suitable for hybridising to any substrate disclosed herein. For embodiments comprising the ligation of a double-stranded adaptor to a single-stranded nucleic acid, a splint oligo, as disclosed herein, may be included.

In some embodiments, the steps may be performed in the order: c), d), a), and then b). This is the order shown in FIG. 16. Thus, in an embodiment, there is provided a method of sample preparation for identifying a feature of interest in a nucleic acid sample, wherein the preparation comprises modifying nucleic acids associated with a feature of interest to be suitable for binding to a substrate comprising immobilised primers, the method comprising, in order:
  c) fragmenting a sample comprising a plurality of nucleic acids; and
  d) exposing the plurality of nucleic acids to a second adaptor under conditions conducive to ligation, wherein the second adaptor comprises an oligonucleotide capable of being ligated to a 5' terminus of a strand at a break induced by fragmentation, and which does not comprise a sequence that is capable of binding to a primer immobilised to the substrate by hybridisation; optionally comprising a sequence identical to a region of a second primer;
  a) exposing the plurality of nucleic acids to conditions capable of cleaving at least one strand of a nucleic acid at a feature of interest, and denaturing the plurality of nucleic acids into single-stranded nucleic acids;
  b) exposing the plurality of nucleic acids to a first adaptor under conditions conducive to ligation, wherein the first adaptor comprises an oligonucleotide capable of being ligated to a 3' terminus of a strand of a cleavage site, but is not capable of being ligated to the second adaptor, and which comprises a sequence that is capable of binding to a primer immobilised to the substrate by hybridisation.

All downstream steps and features disclosed in connection with the methods of identifying DNA DSBs are also relevant to the methods for identifying a feature of interest. In particular, the method may comprise denaturing the sample into single-stranded nucleic acids, for instance to denature any double-stranded adaptors. The method may further comprise contacting the plurality of nucleic acids with the substrate comprising immobilised primers under conditions suitable for hybridisation of the immobilised primers to complementary nucleic acids. In addition, the method may further comprise obtaining sequence information for any nucleic acids hybridised to the substrate.

In another embodiment, there is provided a method of sample preparation for identifying a feature of interest in a nucleic acid sample, wherein the preparation comprises modifying nucleic acids associated with a feature of interest to be suitable for binding to a substrate comprising immobilised primers, the method comprising:
  α) exposing a sample comprising a plurality of nucleic acids to conditions capable of cleaving at least one strand of a nucleic acid at a feature of interest, and denaturing the plurality of nucleic acids into single-stranded nucleic acids;
  β) exposing the sample, under ligation conditions, to a first pair of oligonucleotides a first one of which comprises a 5' binding feature that enables ligation of said oligonucleotide to a first strand of said DSB, a hybridization site (RD1 SP) to which a first sequencing primer can bind and a binding sequence for separating said DSB from a pool of DSBs; and a second oligonucleotide that is complementary to said first oligonucleotide of the first pair; wherein either or both of said oligonucleotides comprise, a 3' and/or 5' protective feature;
  γ) fragmenting the nucleic acid of said sample into fragments; and
  δ) exposing said fragments, under ligation conditions, to a second pair of oligonucleotides a first one of which comprises a hybridization site (RD2 SP) to which a second sequencing primer can bind; and a second longer oligonucleotide that is in part complementary to said first oligonucleotide of the second pair and comprises a 3' binding feature for binding to a second strand of said fragmented nucleic acid, a sequence complimentary to said hybridization site, and a further sequence that is, optionally, a binding sequence for enabling bridge amplification; and wherein either or both of said oligonucleotides comprise a 3' and/or 5' protective feature.

In some embodiments, the order of steps may be step γ), step δ), step α), and then step β). Thus, in another embodiment, there is provided a method of sample preparation for identifying a feature of interest in a nucleic acid sample, wherein the preparation comprises modifying nucleic acids associated with a feature of interest to be suitable for binding to a substrate comprising immobilised primers, the method comprising, in order:
  γ) fragmenting a nucleic acid sample into nucleic acid fragments;
  δ) exposing said fragments, under ligation conditions, to a second pair of oligonucleotides a first one of which comprises a hybridization site (RD2 SP) to which a second sequencing primer can bind; and a second longer oligonucleotide that is in part complementary to said first oligonucleotide of the second pair and comprises a 3' binding feature for binding to a second strand of said fragmented nucleic acid, a sequence complimentary to said hybridization site, and a further sequence that is, optionally, a binding sequence for enabling bridge amplification; and wherein either or both of said oligonucleotides comprise a 3' and/or 5' protective feature.
  α) exposing the sample to conditions capable of cleaving at least one strand of a nucleic acid at a feature of interest, and denaturing the plurality of nucleic acids into single-stranded nucleic acids; and
  β) exposing the sample, under ligation conditions, to a first pair of oligonucleotides a first one of which comprises a 5' binding feature that enables ligation of said oligonucleotide to a first strand of said DSB, a hybridization site (RD1 SP) to which a first sequencing primer can bind and a binding sequence for separating said DSB from a pool of DSBs; and a second oligonucleotide that is complementary to said first oligonucleotide of the first pair; wherein either or both of said oligonucleotides comprise, a 3' and/or 5' protective feature.

The method may further comprise:

ε) denaturing the fragments to provide single strand nucleic acids.

The method may further comprise:

ζ) separating the strands of part ζ) into two groups: group A those fragments that have ligated at a first end the first hybridization site and binding sequence provided by the oligonucleotide of part β) and at another end the second hybridization site and further sequence provided by the oligonucleotide of part δ) and group B those fragments that do not have ligated at a first end the hybridization site and binding sequence provided by the oligonucleotide of part β) and at another end the second hybridization site and further sequence provided by the oligonucleotide of part δ).

The method may further comprise:

η) sequencing the strands of group A using primers that bind to the first and/or second hydrization sites.

In further aspect of the invention, the methods may be adapted to be particularly suitable for use with bead-based systems. For instance, Ion Torrent sequencing. A particular embodiment is exemplified in FIGS. 14 and 15.

As such, in an aspect of the invention, there is provided a method of sample preparation for identifying DNA DSBs in a nucleic acid sample, wherein the preparation comprises modifying DSB-associated nucleic acids to be suitable for binding to a substrate comprising an immobilised first primer, the method comprising:

1) providing a sample comprising a plurality of nucleic acids;
2) exposing the plurality of nucleic acids to a first adaptor under conditions conducive to ligation, wherein the first adaptor comprises an oligonucleotide capable of being ligated to a 3' terminus of a strand of a DSB and which comprises a sequence that is capable of hybridising to a second primer;
3) fragmenting the plurality of nucleic acids;
4) exposing the plurality of nucleic acids to a second adaptor under conditions conducive to ligation, wherein the second adaptor comprises an oligonucleotide capable of being ligated to a 5' terminus of a strand at a break induced by fragmentation, but is not capable of being ligated to the first adaptor, and which comprises a sequence identical to a region of the immobilised first primer; and
5) contacting the plurality of nucleic acids with the second primer under conditions suitable for extension of the primer.

The sample comprising a plurality of nucleic acids may be any as disclosed herein. In particular, the sample may be suspected of containing DSBs, may be treated with agents capable of causing of suspected of being capable of causing DSBs, or may comprise or be suspected of comprising a feature of interest that can be converted into a DSB. The sample may include a feature of interest capable of being specifically cleaved.

The sample may be any DNA sample capable of comprising DSBs, for instance gDNA.

In a particular embodiment, step 2) is:

exposing the plurality of nucleic acids to a first adaptor pair under conditions conducive to ligation, wherein the first adaptor pair is capable of being ligated to at least a 3' terminus of a strand of a DSB, and wherein the first adaptor pair comprises first and second oligonucleotides that are at least partially complementary, and the first oligonucleotide is ligatable to a 3' terminus and comprises a sequence that is capable of hybridising to a second primer; and wherein step 4) is:

exposing the plurality of nucleic acids to a second adaptor pair under conditions conducive to ligation, wherein the second adaptor pair is capable of being ligated to at least a 5' terminus of a strand at a break induced by fragmentation but is not capable of being ligated to the first oligonucleotide of the first adaptor pair, wherein the second adaptor comprises first and second partially complementary oligonucleotides, and the first oligonucleotide is ligatable to a 5' terminus and comprises a sequence identical to a region of the immobilised first primer, and the second oligonucleotide does not comprise a sequence that is complementary to said sequence identical to a region of the immobilised first primer.

In particular embodiments, the oligonucleotide of the second adaptor pair that is ligatable to a 5' terminus comprises 5, 10, 15, 20, or all 23 bases of the sequence according to AACCCACTACGCCTCCGCTTTCC (SEQ ID NO: 40). The other oligonucleotide is of a sequence that does not comprise a sequence of more than 5, 10, 15, 20 bases, or does not comprise all 22 bases, of the sequence GGAAAGCGGAGGCGTAGTGGTT (SEQ ID NO: 36).

The oligonucleotides according to SEQ ID NO: 36 and SEQ ID NO: 40 may comprise from 1 to 12, 1 to 10, 1 to 8, 1 to 5, 1 to 3, 2, or 1 modifications such as substitutions, deletions, or insertions. In an embodiment, the modifications are substitutions.

The first and/or second oligonucleotides of the first adaptor pair may comprise a 3' and/or a 5' protective feature. These protective features may be any as disclosed herein, particularly any disclosed in connection with the first pair of oligonucleotides discussed in relation to step i) of the methods disclosed herein.

The first and/or second oligonucleotides of the second adaptor pair may comprise a 3' and/or a 5' protective feature. These protective features may be any as disclosed herein, particularly any disclosed in connection with the second pair of oligonucleotides discussed in relation to step iii) of the methods disclosed herein.

In particular embodiments, the second adaptor is not capable of being ligated to the first adaptor due to the presence of a 3' modification of the first adaptor. For instance, a C3 3' chain terminator.

The oligonucleotide of the second adaptor that is ligatable to a 5' terminus comprises a sequence identical to a region of a second primer such that, when a complementary strand is generated, the complementary strand comprises a region to which the primer can bind by hybridisation. This sequence identical to a region of a second primer may be identical to 5, 10, 15, 20, 21, 24, or more bases of an immobilised primer.

The method may further comprise denaturing the plurality of nucleic acids to form a plurality of single-stranded nucleic acids. The features of this step may be any as disclosed herein in connection with other embodiments of the invention.

The method may further comprise contacting the plurality of nucleic acids with the substrate comprising the immobilised first primer under conditions suitable for hybridisation of the immobilised first primer to complementary nucleic acids. For instance, the sample of nucleic acids with ligated adaptors may then be bound to the substrate, such as a bead comprising immobilised primers. The primers may be immobilised to the bead such that the 5' end is proximal and the 3' end is distal to the point of immobilisation.

Routine techniques may be used such that the substrate, such as the bead, displays multiple copies of a nucleic acid with the same sequence.

The methods may further comprise obtaining sequence information for any nucleic acids hybridised to the substrate. The adaptors may comprise sites for the binding of sequencing primers, to assist with this process. The adaptors may comprise index sequences to assist with this process.

According to a further aspect of the invention there is provided a double strand adaptor, suitable for identifying DNA double-strand breaks (DSBs) in a nucleic acid sample, such as a gDNA sample, comprising:
- a first oligonucleotide that comprises a sequence according to AACCCACTACGCCTCCGCTTTCC (SEQ ID NO: 40); and
- a second oligonucleotide of a sequence that does not comprise a sequence of more than 5, 10, 15, 20 bases, or does not comprise all 22 bases, of the sequence GGAAAGCGGAGGCGTAGTGGTT (SEQ ID NO: 36); wherein either or both of said oligonucleotides comprise, respectively, a 3' and/or 5' protective feature.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Any features disclosed in connection with the statements of invention featuring steps i), ii), iii), etc may be combined with features disclosed in connection with the statements of invention featuring steps a), b), c) etc. Any features disclosed in connection with the statements of invention featuring steps a), b), c), etc may be combined with features disclosed in connection with the statements of invention featuring steps i), ii), iii) etc Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

The present invention will now be described by way of example only with particular reference to the following figures wherein:

EXAMPLES

Methods
Cell Culture and Treatment

HEK293, HEK293T, and U2OS DIVA cells were cultured in DMEM (Life Technologies) supplemented with 10% FBS (Life Technologies) at 37° C. at 5% $CO_2$. HEK293 cells were nucleofected with 224 pmol Ribonucleoprotein (RNP) per $3.5 \times 10^5$ cells using a Lonza 4D-Nucleofector X unit with pulse code CM-130. Cells were harvested at 0, 7, 12, 24, and 30 h post nucleofection for INDUCE-seq processing. To stimulate AsiSI-dependent DSB induction, DIVA cells were treated with 300 nM 4OHT (Sigma, H7904) for 4 h.

Cas9 Protein and sgRNA

The guide RNA targeting EMX1 (GAGTCCGAGCA-GAAGAAGAA; SEQ ID NO: 29) was synthesized as a full-length non-modified sgRNA oligonucleotide (Synthego). Cas9 protein was produced in-house (AstraZeneca) and contained an N-terminal 6xHN tag.

INDUCE-Seq Method

Cells were seeded to 96 well plates pre-coated with Poly-D-lysine (Greiner bio-one, 655940) at a density of $\sim 1 \times 10^5$/well and crosslinked in 4% Paraformaldehyde (PFA) (Pierce, 28908) for 10 min at room temperature (rt). Cells were washed in 1xPBS to remove formaldehyde and stored at 4° C. for up to 30 days. The INDUCE-seq method was initiated by permeabilising cells. Between incubation steps, cells were washed in 1xPBS at rt. Cells were permeabilised by incubation in Lysis buffer 1 (10 mM Tris-HCL pH 8, 10 mM NaCl, 1 mM EDTA, 0.2% Triton X-100, pH 8 at 4° C.) for one hour at rt, followed by incubation in Lysis buffer 2 (10 mM Tris-HCL, 150 mM NaCl, 1 mM EDTA, 0.3% SDS, pH 8 at 25° C.) for one hour at 37° C. Permeabilised cells were washed three times in 1x CutSmart® Buffer (NEB, B7204S) and blunt-end repaired using NEB Quick Blunting Kit (E1201L)+100 µg/mL BSA in a final volume of 50 µL at rt for one hour. Cells were then washed three times in 1x CutSmart® Buffer and A-tailed to add a single dATP to the 3' end of the double stranded DNA using NEBNext® dA-Tailing Module (NEB, E6053L) in a final volume of 50 µL at 37° C. for 30 mins. A-tailed cells were washed three times in 1x CutSmart® buffer then incubated in 1xT4 DNA Ligase Buffer (NEB, B0202S) for 5 mins at rt. A-tailed ends were labelled by ligation using the T4 DNA ligase (NEB, M0202M)+0.4 µM of P5 adaptor in a final volume of 50 µL at 16° C. for 16-20 h. Following ligation, excess P5 adaptor was removed by washing cells 10 times in wash buffer at rt (10 mM Tris-HCL, 2 M NaCl, 2 mM EDTA, 0.5% Triton X-100, pH 8 at 25° C.), incubating for 2 mins each wash step. Cells were washed once in PBS and then once in nuclease free $H_2O$ (IDT, Nov. 5, 2001-04). Genomic DNA was extracted by incubating cells in DNA extraction buffer (10 mM Tris-HCL, 100 mM NaCl, 50 mM EDTA, 1.0% SDS, pH 8 at 25° C.)+1 mg/mL Proteinase K (Invitrogen, AM2584) in a final volume of 100 µL for 5 mins at rt. The cell lysates were transferred to 1.5 mL Eppendorf RNA/DNA LoBind tubes (Fisher Scientific, 13-698-792) and incubated at 65° C. for 1 hour, shaking at 800 rpm. DNA was purified using Genomic DNA Clean & Concentrator™-10 (Zymo Research, D4010), and eluted using 100 µL Elution Buffer. DNA yield was assessed using 1 µL sample and Qubit DNA HS Kit (Invitrogen, Q32854) before proceeding to library preparation. Genomic DNA was fragmented to 300-500 bp using a Bioruptor Sonicator, and size selected using SPRI beads (GC Biotech, CNGS-0005) to remove fragments <150 bp. Fragmented and size-selected DNA was end-repaired using NEBNext® Ultra™ II DNA Module (NEB, E7546L). Fragmented and end-repaired DNA was added directly to the ligation reaction using NEBNext® Ultra™ II Ligation Module (NEB, E7595L) according to the manufacturer's instructions using 7.5 µM Modified half-functional P7 adaptor and omitting USER enzyme addition. The ligated sequencing libraries were purified using SPRI beads. Libraries were purified twice more using SPRI beads, and size selected to remove fragments <200 bp to remove residual adaptor DNA. Final clean libraries were quantified by qPCR using the KAPA Library Quantification Kit for Illumina® Platforms (Roche, 07960255001). Samples were pooled and concentrated to the desired volume for sequencing using a SpeedVac. Sequencing was performed on an Illumina NextSeq 550 using 1×75 bp High Capacity flow cell.

INDUCE-Seq Adaptors

Figure 2:
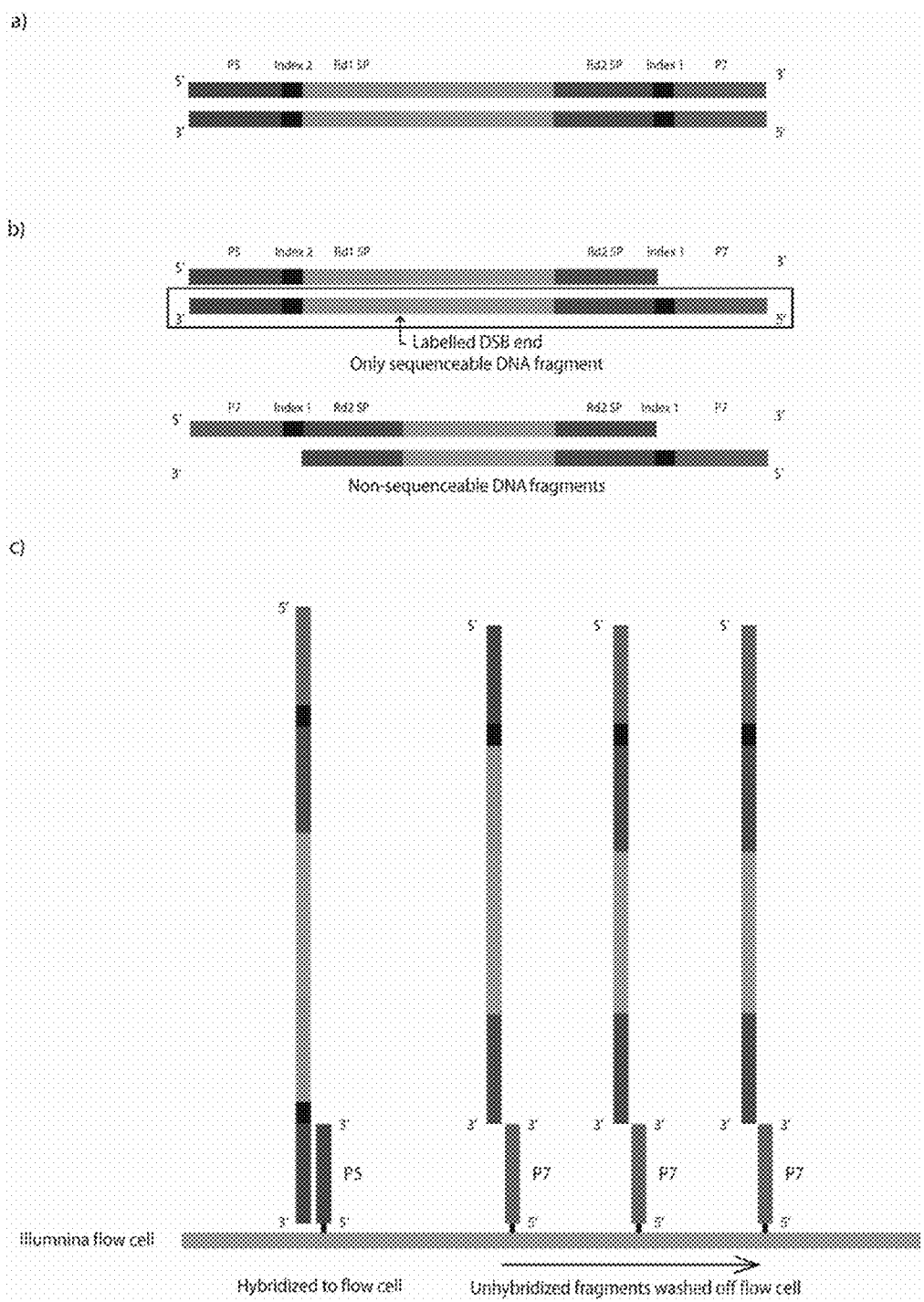
FIG. 2. Detailed schematic of flow cell enrichment adaptor design. (a) Structure of a complete adaptor ligated dsDNA fragment for sequencing. 3' P5 and P7 adaptors hybridize with the flow cell. Sequencing primers bind to the Read 1 Sequencing primer (RD1 SP) and the Read 2 Sequencing primer (RD2 SP) sequences during the first and second sequencing read. Indexes allow differentiation of different samples in a library pool. (b) Structure of DNA fragments present in an INDUCE-seq library. Only the DSB ligated fragment is comprised of all the adaptor components required for sequencing. (c) Loading of the INUCE-seq library on to the sequencing flow cell will enrich for DSB ligated fragments via hybridization of the 3' ends of P5 adaptor sequences. No other fragments can interact with flow cell and will be removed.

All modified INDUCE-seq adaptor oligonucleotides were purchased from IDT. Single stranded oligonucleotides were annealed at a final concentration of 10 µM in Nuclease-free Duplex Buffer (IDT, Nov. 1, 2003-01) by heating to 95° C. for 5 minutes and slowly cooling to 25° C. using a thermocycler. An overview of the structure of the adaptor oligonucleotides is provided in FIG. 2.

In Situ DSB Induction with HindIII

Pilot INDUCE-seq experiments were performed by inducing DSBs in situ in HEK293T cells using the restriction enzyme HindIII-HF® (NEB, R3104S). This process was the same as described for the full INDUCE-seq method, with the addition of DSB induction prior to end blunting. Following cell permeabilization DSBs were induced using 50 U HindIII-HF® in 1× CutSmart® Buffer in a final volume of 50 µL. Digestions were performed at 37° C. for 18 hours.

INDUCE-Seq Data Analysis Pipeline

Demultiplexed FASTQ files were obtained and passed through Trim Galore! (Krueger 2015) to remove the adaptor sequence at the 3' end of reads using the default settings. Quality of the sequencing data was assessed using FastQC (Andrews 2010). Following read alignment to the human reference genome (GRCh37/hg19) using BWA-mem (Li and Durbin 2009), alignments mapped with a low alignment score (MAPQ <30) were removed using SAMtools (Li et al. 2009) and soft-clipped reads were filtered using a custom AWK script to ensure accurate DSB assignment. The resulting BAM files were converted into BED files using bedtools bam2 bed function (Quinlan and Hall 2010), after which the list of read coordinates were filtered using regions of poor mappability, chromosome ends, and incomplete reference genome contigs, to remove these features from the data. DSB positions were assigned as the first 5' nucleotide upstream of the read relative to strand orientation and were output as a 'breakends' BED file. Care was taken to remove optical duplicates while retaining real recurrent DSB events. By maintaining each read ID, flow cell X and Y positional information was used to filter out optical duplicates using a custom AWK script. The final output was a BED file containing a list of quantified single nucleotide break positions.

HindIII-Induced DSB Analysis in HEK293T Cells

The positions of HindIII target sites within hg19 were first predicted in silico using the tool SeqKit locate (Shen et al. 2016), allowing a max mismatch of 2 bp from the HindIII target sequence AAGCTT. The number of breaks overlapping with these predicted sites was calculated using bedtools intersect. To compare with the DSBCapture EcoRV experiment (Lensing et al. 2016), the same coverage threshold of ≥5 breaks per site was used to define each HindIII induced break site.

Asisi-Induced DSB Detection and Analysis in DIvA Cells

The positions of AsiSI target sites were calculated in the same way as for HindIII, however with no mismatches allowed and using the sequence GCGATCGC. As DIVA cells are female, sites present on the Y chromosome were removed leaving 1211 sites for chr1-X. To stringently calculate genuine AsiSI induced breaks, the 8 bp AsiSI site was reduced to 1 bp genomic intervals at the predicted break positions. This reduced each 8 bp genomic interval to two 1 bp intervals; at position 6 on the plus strand, and position 3 on the minus strand. Direct overlaps were then calculated between 1 bp breakend positions and the predicted AsiSI break sites using bedtools intersect. Matching strand orientation was required for each overlap to be considered a genuine AsiSI-induced break site.

CRISPR Off-Target Analysis Pipeline

Two sets of potential off-target sites for EMX1 in hg19 were first predicted using the command line version of Cas-OFFinder (Bae et al. 2014), allowing up to 6 mismatches in the spacer and canonical PAM combined for the first set, and up to 7 mismatches for the second. Next, both sets of predicted sequences were filtered based on the mismatch number in the seed region, defined as the 12 nucleotides proximal to the PAM. Each set was filtered for up to 2, 3, 4 and 5 mismatches in the seed, generating a set of 8 files with different mismatch filtering parameters. To define CRISPR-induced DSBs, each 23 bp predicted site was first reduced to a 2 bp interval flanking the expected CRISPR break position, 3 bp upstream of the PAM. Overlaps were then calculated between these 2 bp expected break regions and the INDUCE-seq 1 bp breakend positions using bedtools intersect (Quinlan and Hall 2010), returning a set of DSBs identified at expected CRISPR break sites. Finally, DSBs overlapping with CRISPR sites were filtered based on the site mismatch number and the number of breaks detected at the site. Sites possessing mismatches >n were required to have more than 1 DSB overlap to be retained as a genuine off-target site. Each set of break overlaps was filtered using a mismatch value of >2, >3, >4 and >5, resulting in a total of 32 filter conditions and off-target datasets for each INDUCE-seq sample.

Calculating Overlaps Between CRISPR Off-Target Detection Methods

EMX1 off-target sites were compared with alternative methods CIRCLE-seq, Digenome-seq, GUIDE-seq, BLISS, and HTGTS. Genome interval files were generated for each respective off-target detection method. Overlaps of the EMX1 off-targets detected by each method were calculated using bedtools intersect (Quinlan and Hall 2010).

Amplicon-Seq Validation of Mutational Outcome

Amplicon sequencing DNA libraries were prepared using a custom panel of rhAmpSeq RNase-H dependent primers (IDT) that flank the INDUCE-seq identified off-targets for EMX1. Multiplex PCR was carried out according to manufacturer's instructions using the rhAmpSeq HotStart Master Mix 1, the custom primer mix, and 10 ng of genomic DNA. PCR products were purified using SPRI beads and illumina sequencing P5 and P7 index sequences were incorporated through a second multiplex PCR using rhAmpSeq HotStart Master Mix 2. Resulting sequencing libraries were pooled and sequenced using an Illumina NextSeq 550 Mid Output flow cell with 2×150 bp chemistry. Editing outcomes at the on- and off-targets were determined using CRISPResso software (Pinello et al. 2016) v2.0.32 with the following parameters: CRISPRessoPooled-q30-ignore_substitutions max_paired_end_reads_overlap 151. Indel frequencies were compared using CRISPRessoCompare.

Results

Figure 5:
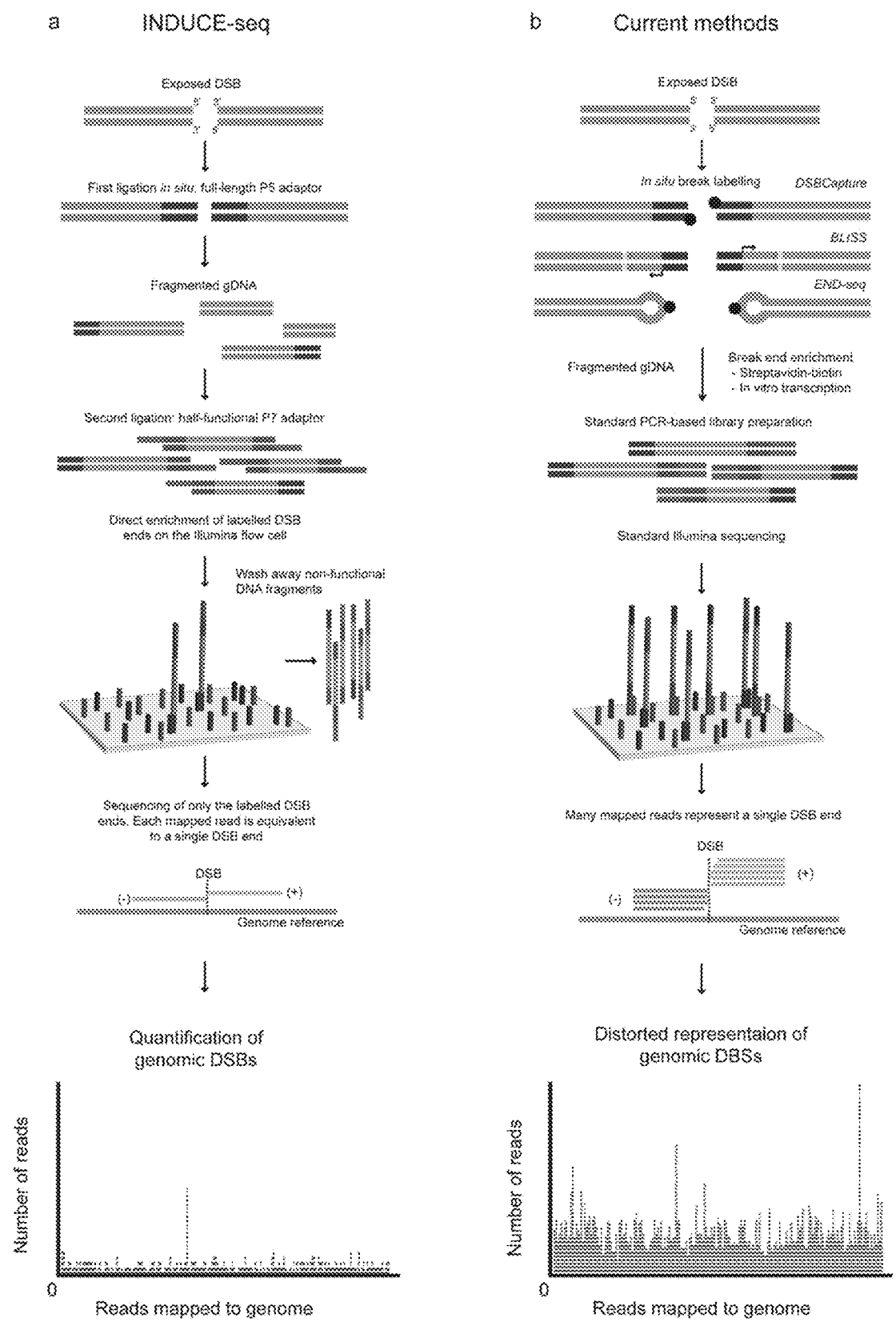
FIG. 5. Comparison of INDUCE-seq and current DSB mapping workflows. (a) Overview of INDUCE-seq workflow. The sequencing of INDUCE-seq libraries generates a quantitative output where one read is equivalent to one break. (b) Overview of the DSBCapture, BLISS and END-seq workflows. Sequencing following standard library construction generates an output one read is not equivalent to a single DSB.

Break measurement by INDUCE-seq is achieved via a two-stage, PCR-free library preparation (FIGS. 1 and 5).

Stage one consists of labelling in situ end-prepared DSBs via ligation of a full-length, chemically modified P5 adaptor to DSB ends. In stage two, extracted, fragmented, and end-prepared gDNA is ligated using a second chemically modified half-functional P7 adaptor. The resulting DSB-labelled DNA fragments that comprise both the P5 and half-functional P7 adaptors can interact with the Illumina flow cell and subsequently be sequenced using single-read sequencing. DNA fragments that do not possess the P5 adaptor remain non-functional as they lack the sequence required to hybridize to the flow cell. This methodology enables the enrichment of functionally labelled DSB sequences and the elimination of all other genomic DNA fragments, which would otherwise contribute to system noise. The avoidance of break amplification produces a sequencing output where a single sequencing read is equivalent to a single labelled DSB end (compare FIGS. 5a and 5b, see FIG. 8a). This innovation enables the direct measurement, and therefore quantification, of DSBs by sequencing, representing a major advance in the accurate measurement of DSBs in the genome.

Figure 6:
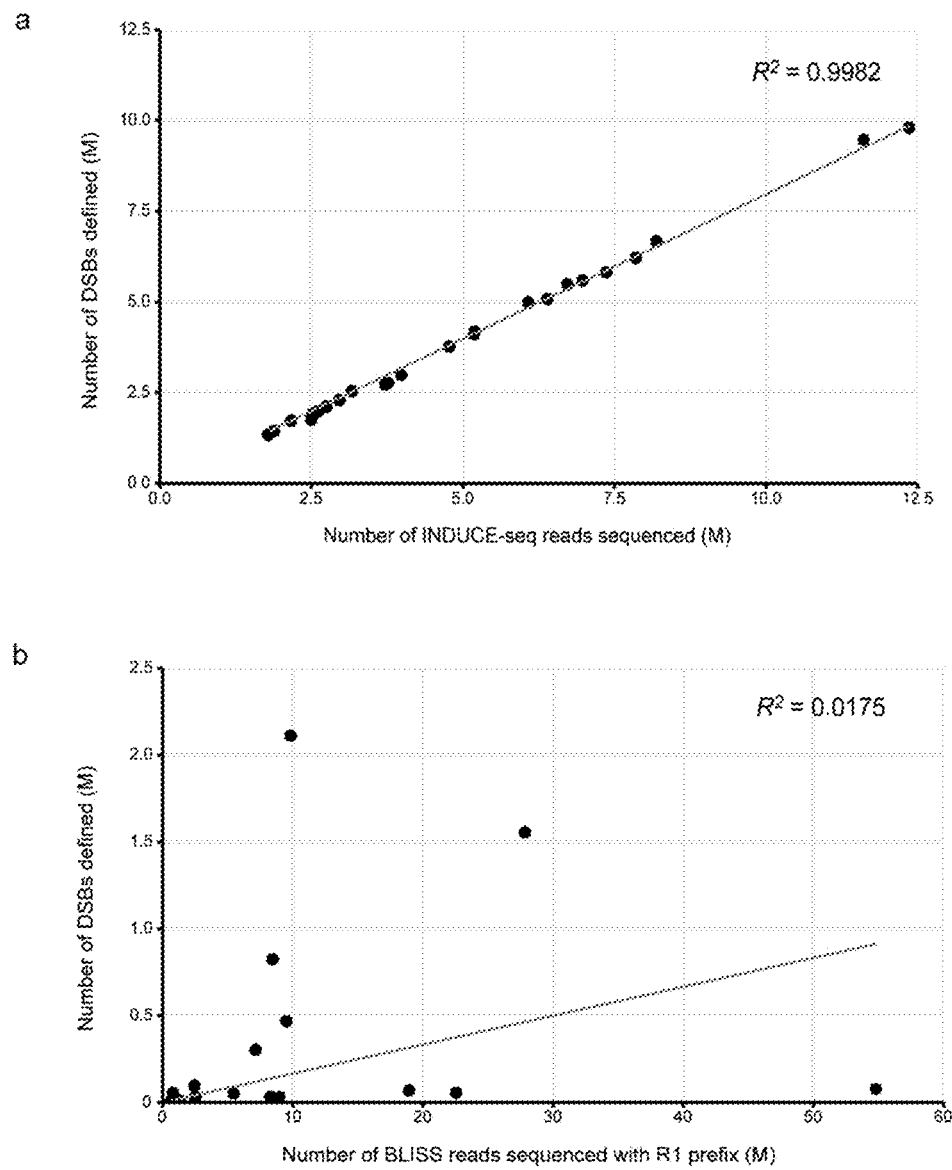
FIG. 6. Comparison between the number of reads sequenced and number of DSBs defined for INDUCE-seq and BLISS NGS libraries. (a) Scatter plot of the number of INDUCE-seq reads sequenced and the number of breaks defined from individual INDUCE-seq experiments. (b) Scatter plot showing the number of BLISS reads sequenced with the correct read 1 (R1) barcode prefix and the number of breaks defined following duplicate-removal using UMI correction, from individual BLISS experiments.

Following in situ break labelling, currently available DSB detection methods BLISS, DSBCapture and END-seq, all employ an enrichment protocol to separate DSB-labelled DNA fragments from the remaining genomic DNA. This is followed by a PCR-based library preparation, and sequencing (FIG. 5b). This amplification-based approach results in a sequencing output where a single read is not equivalent to a single break, where a PCR error correction protocol such as unique molecular identifiers (UMI) is required to attempt DSB quantification (FIG. 5b and FIG. 6b) (Yan et al. 2017). Importantly, the novel INDUCE-seq library preparation and adaptor combination is compatible with any published in situ DSB labelling protocol.

Figure 3A:
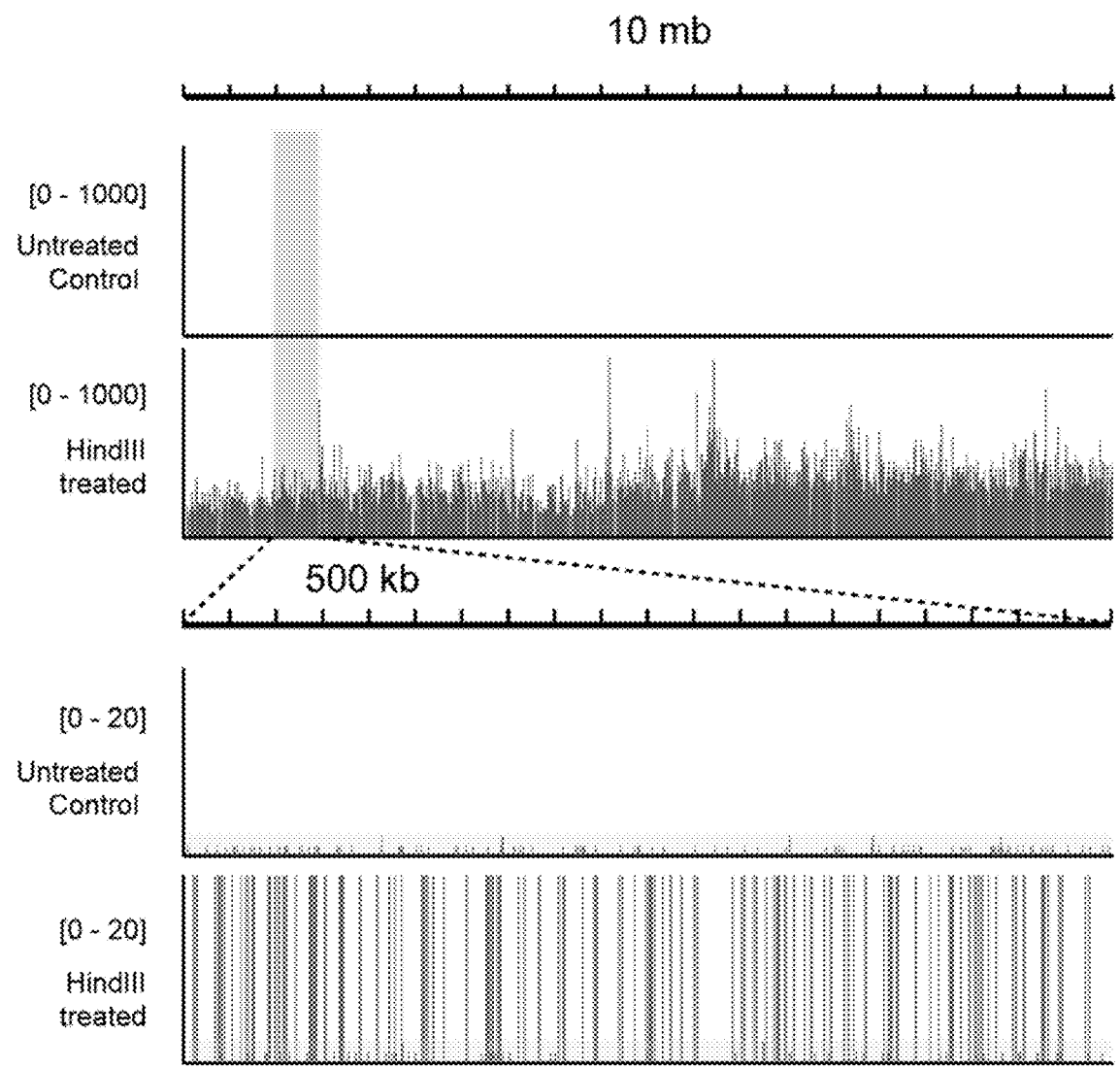
(FIG. 3a) INDUCE-seq detects highly recurrent induced DSBs and single endogenous DSBs simultaneously with high resolution. Genome browser view of INDUCE-seq reads mapped to a 10 mb section of the genome from HEK293T cells following in situ cleavage with the restriction endonuclease HindIII. (Top panel) Highly recurrent enzyme-induced breaks represent the vast majority of reads when viewed at the high level (10 mb, 0-1000 reads). (Bottom panel) A closer zoom (pink highlight, 500 kb, 0-20 reads) reveals low level single endogenous breaks present in both the untreated sample and amongst the recurrent HindIII-induced breaks (Green highlight).
Figure 3G:
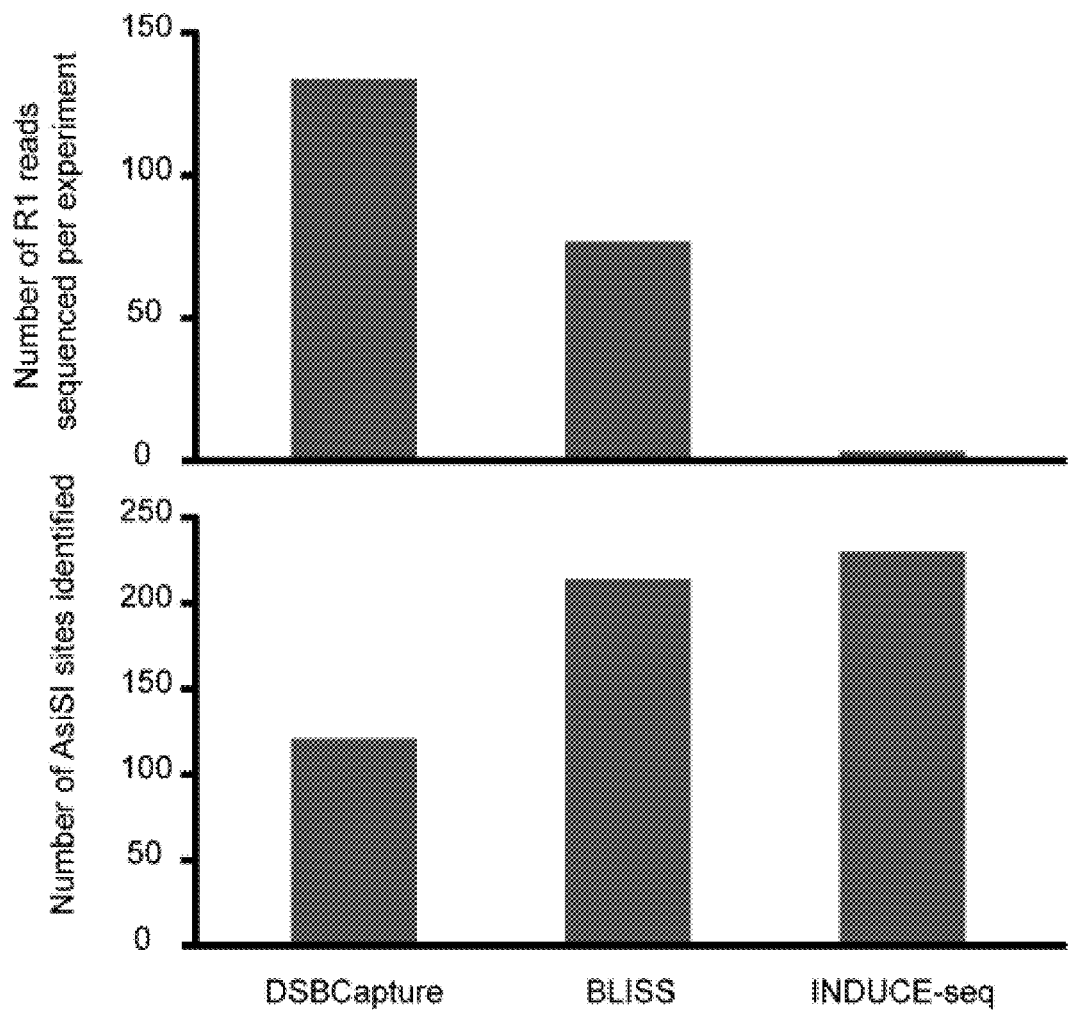
(FIG. 3g) Comparison between INDUCE-seq, DSBCapture and BLISS in detecting AsiSI induced breaks in live DiVA cells. The number of reads sequenced (top panel) is compared to the number of AsiSI sites identified for each experiment (bottom panel). INDUCE-seq sensitively detects the greatest number of AsiSI sites using 40-fold fewer reads than DSBCapture and 23-fold fewer reads than BLISS.
Figure 7A:
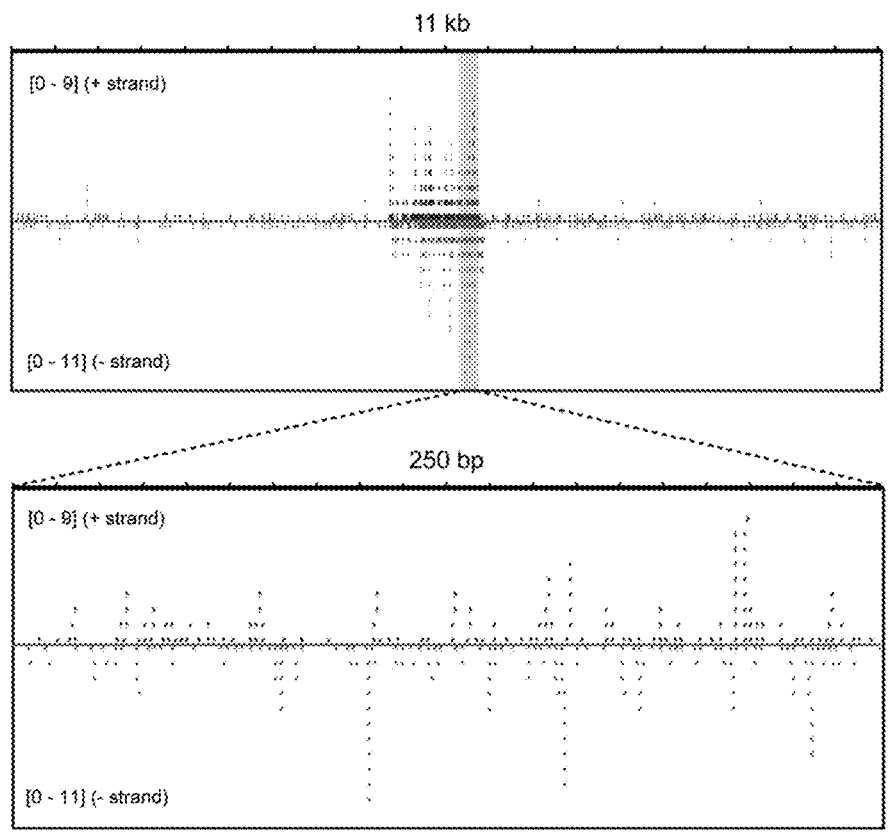
(FIG. 7a) 11 kb view of a ch17 DSB hotspot. Purple arrows represent DSB ends labelled on the right side (+ strand) and blue arrows represent DSB ends labelled on the left side (− strand). Recurrent DSBs are evenly distributed throughout the hotspot region.
Figure 7B:
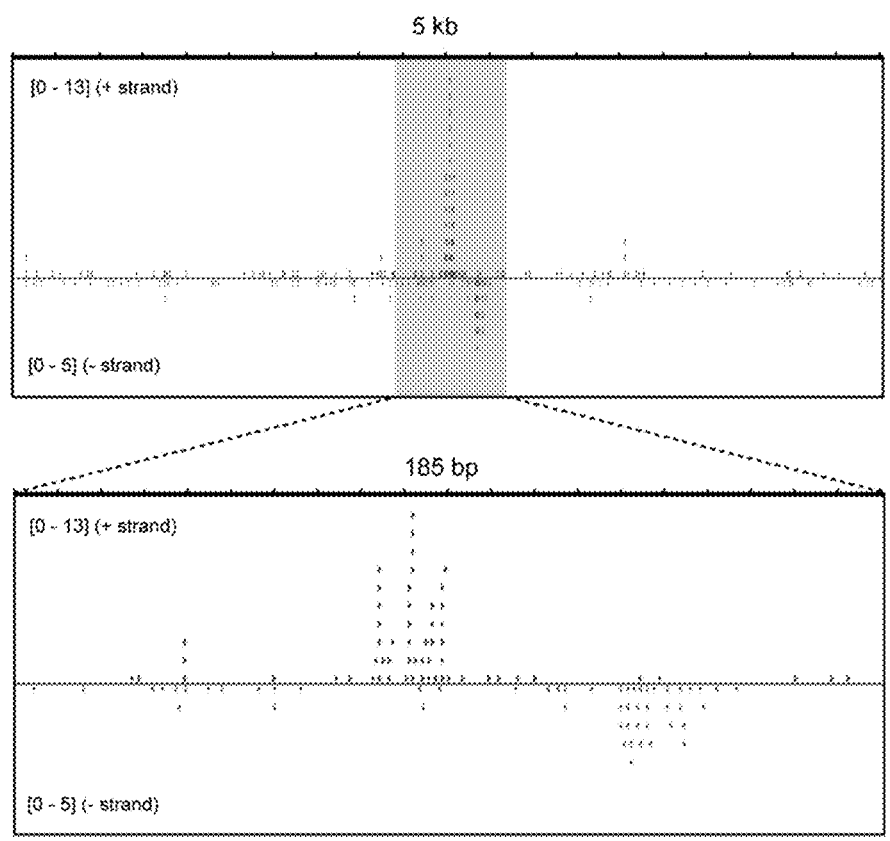
(FIG. 7b) 5 kb view of a chr11 DSB hotspot. Recurrent DSBs can be detected at different positions on the plus and minus strands.

To demonstrate the features of the INDUCE-seq methodology, we first examined how INDUCE-seq measures DSBs genome-wide following the induction of defined DSBs in fixed and permeabilised cells using a high-fidelity HindIII restriction endonuclease. This approach has been used previously to benchmark the methods BLISS, END-seq and DSBCapture. As shown in FIG. 3a, INDUCE-seq simultaneously detects hundreds of millions of highly recurrent HindIII-induced DSBs, in addition to hundreds of thousands of lower-level endogenous DSBs from within the same sample, without the need for any form of error-correction. This enables the precise quantification and characterisation of endogenous DSBs in the genome for the first time. FIG. 7 shows an example of endogenous DSB detection using INDUCE-seq in HEK293 cells. Collectively, these observations show the remarkably broad dynamic range and sensitivity achievable with INDUCE-seq. FIG. 3.b shows that INDUCE-seq detects the expected HindIII cleavage pattern, where two semi-overlapping symmetrical blocks of forward and reverse sequencing reads map to the known HindIII cleavage sites on both the forward and reverse strand. This confirms that INDUCE-seq can be used to precisely measure DSB end structures at single nucleotide resolution. We measured a dramatic increase in breaks per cell following treatment of cells with HindIII, from fewer than 10 endogenous breaks per untreated cell to more than 3000 induced breaks per treated cell. This demonstrates that INDUCE-seq is capable of quantitatively measuring breaks-per-cell across three orders of magnitude (FIG. 3c). Compared with an equivalent experiment using the method DSBCapture to detect EcoRV induced breaks, we found that a greater proportion of both total, and aligned INDUCE-seq reads were mapped to restriction sites. Significantly, 96.7% of aligned reads were mapped to restriction sites, representing a 25% improvement in fidelity of break detection over DSBCapture (FIG. 3d). Importantly, INDUCE-seq used 800-fold fewer cells than the DSBCapture experiment, and identified a similar proportion of HindIII restriction sites (92.7%) to that identified by DSBCapture for EcoRV (93.7%) (FIG. 3e). In addition to on-target HindIII sites comprising the sequence AAGCTT, we identified a substantial number of DSBs at a variety of HindIII off-target sequences, differing by one or two mismatching bases (FIG. 3f). The total number of HindIII induced DSBs measured by INDUCE-seq ranged from ~150,000,000 at on-target sites to just five DSBs at the lowest ranking off-target site. INDUCE-seq therefore quantitatively detects breaks across eight orders of magnitude, demonstrating a vastly enhanced dynamic range of break detection over other methods. Enhanced sensitivity was also observed when similar experiments which measure the DSBs induced at AsiSI sites in live DiVA cells were conducted. Despite sequencing 40-fold fewer reads than a corresponding DSBcapture experiment, and 23-fold fewer reads than BLISS, INDUCE-seq detected the presence of breaks at 230 AsiSI sites. This represents an increase over the 214 sites detected by BLISS, and 121 sites detected by DSBCapture. This demonstrates that INDUCE-seq is significantly more sensitive, efficient, and therefore cost effective than any current break detection method (FIG. 3g).

Figure 4A:
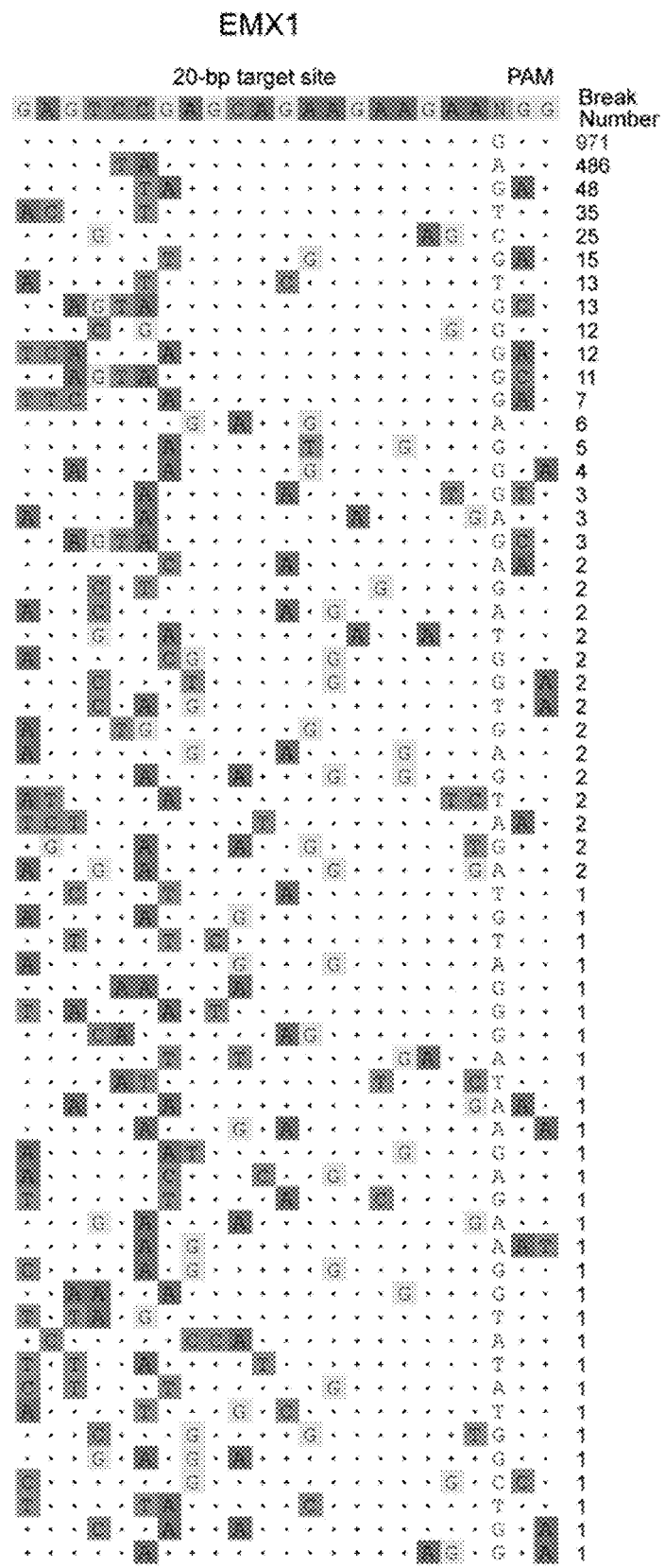
(FIG. 4a) Off-target sequences and the number of breaks identified using INDUCE-seq for the EMX1 sgRNA. This figure includes GAGTCCGAGCAGAAGAAGAANGG (SEQ ID NO: 44).
Figure 8:
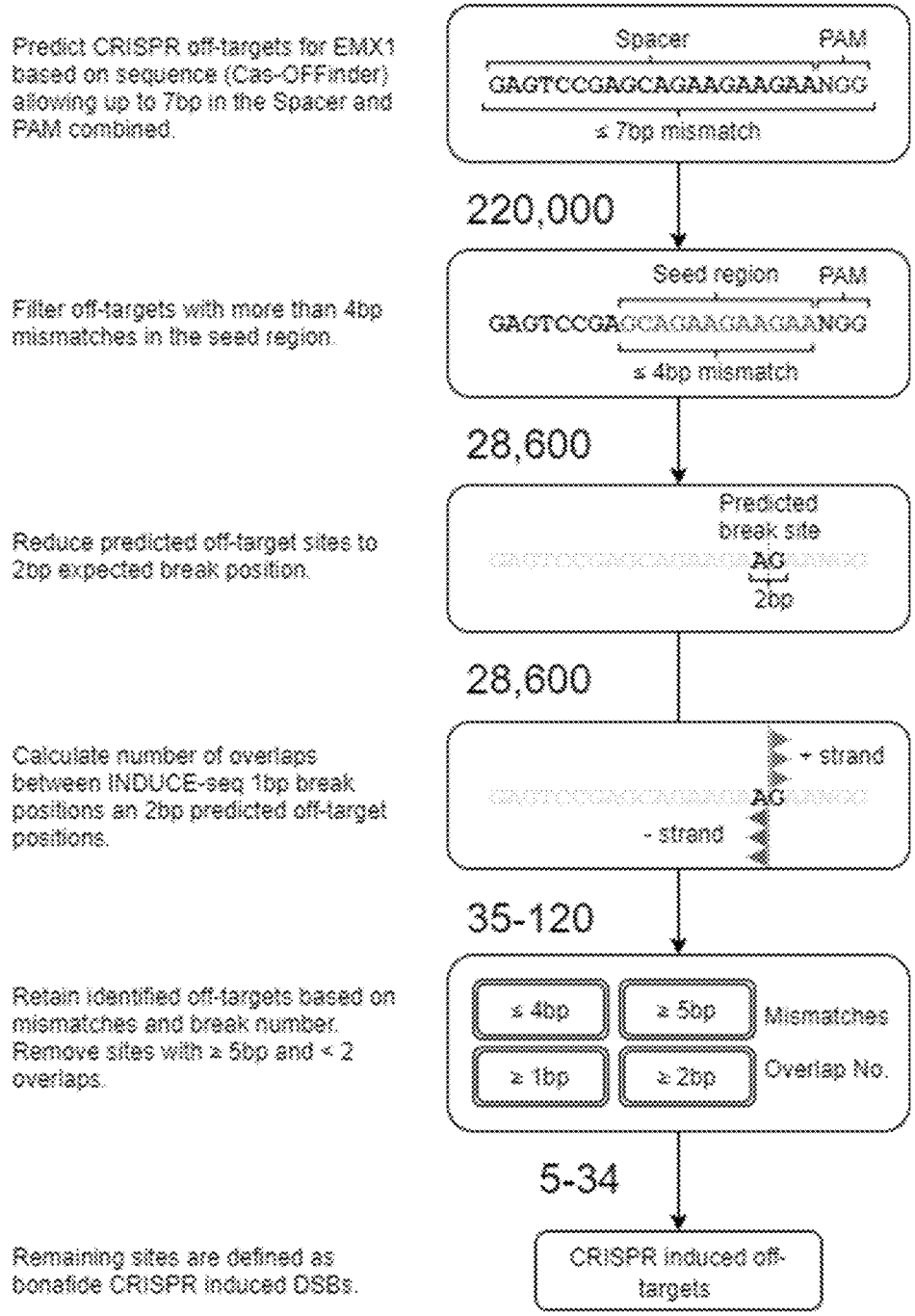
FIG. 8. Schematic of the off-target discovery pipeline used for INDUCE-seq. The sequence in FIG. 8 is SEQ ID NO: 44.
Figure 9:
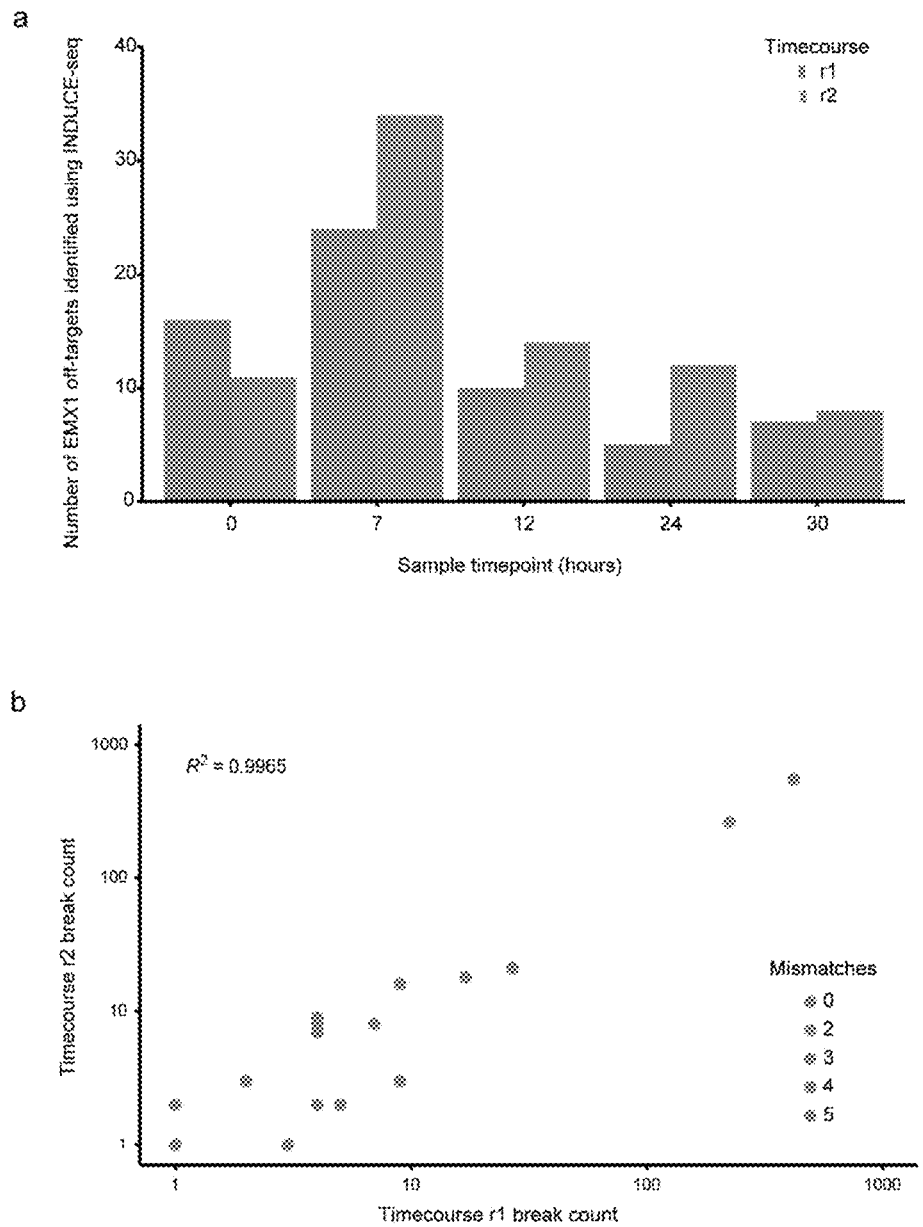
FIG. 9. CRISPR off-target discovery using INDUCE-seq is highly reproducible. (a) Comparison between the number of EMX1 off-targets detected across r1 and r2 timecourse experiments. (b) Scatterplot showing the break number found at CRISPR off-target sites identified in both independent experiments.
Figure 10A:
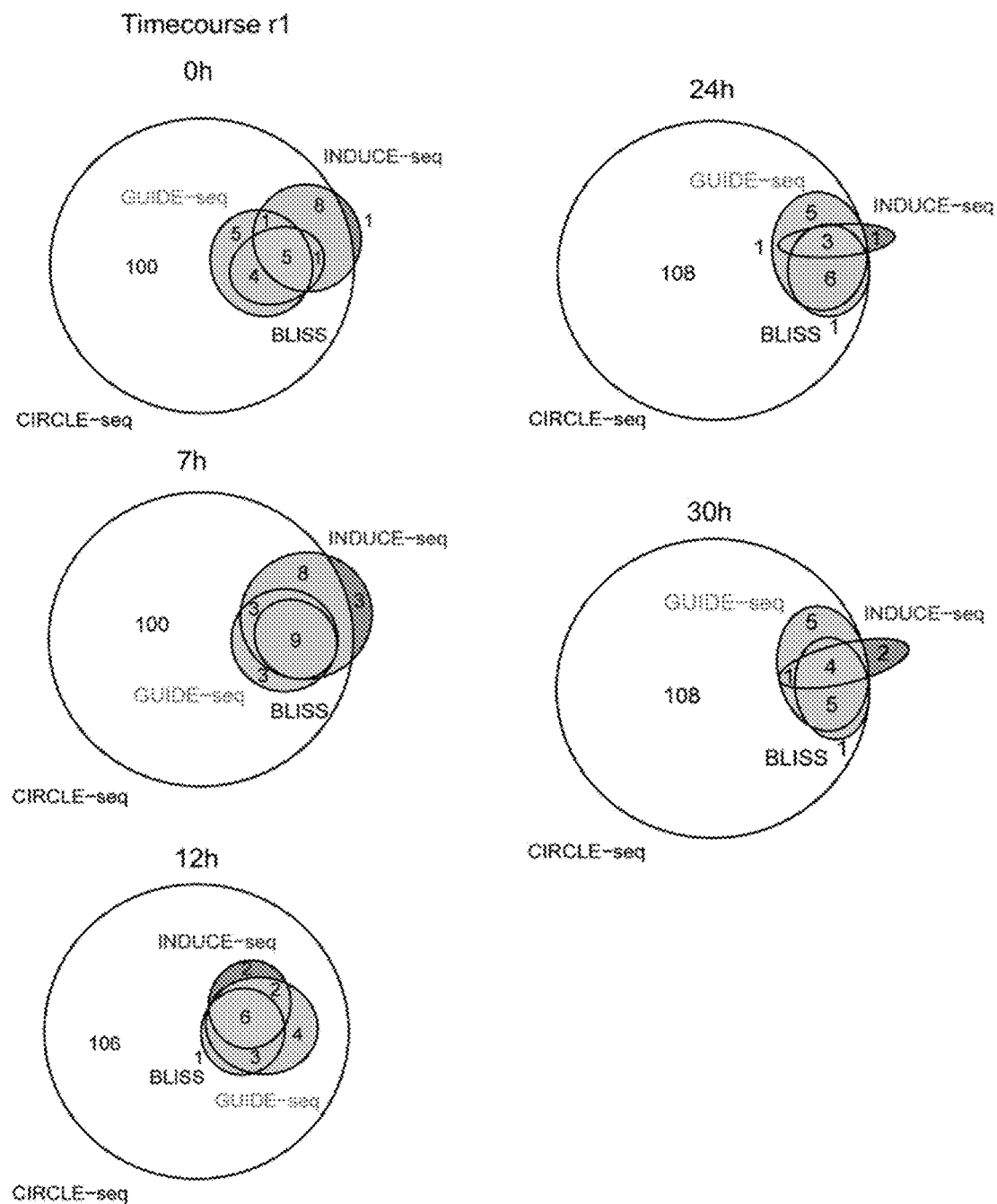
FIG. 10. Venn diagrams showing intersection of the off-targets identified by INDUCE-seq, CIRCLE-seq, GUIDE-seq and BLISS. (a and b) Overlaps calculated for samples 0 h to 30 h in isolation from the independent experiments r1 (FIG. 10a) and r2 (FIG. 10b).
(FIG. 10c and FIG. 10d) The combined overlaps from all time points for set r1 (FIG. 10c) and r2 (d).
(FIG. 10e) Overlaps calculated between methods when all INDUCE-seq samples are combined.
Figure 10B:
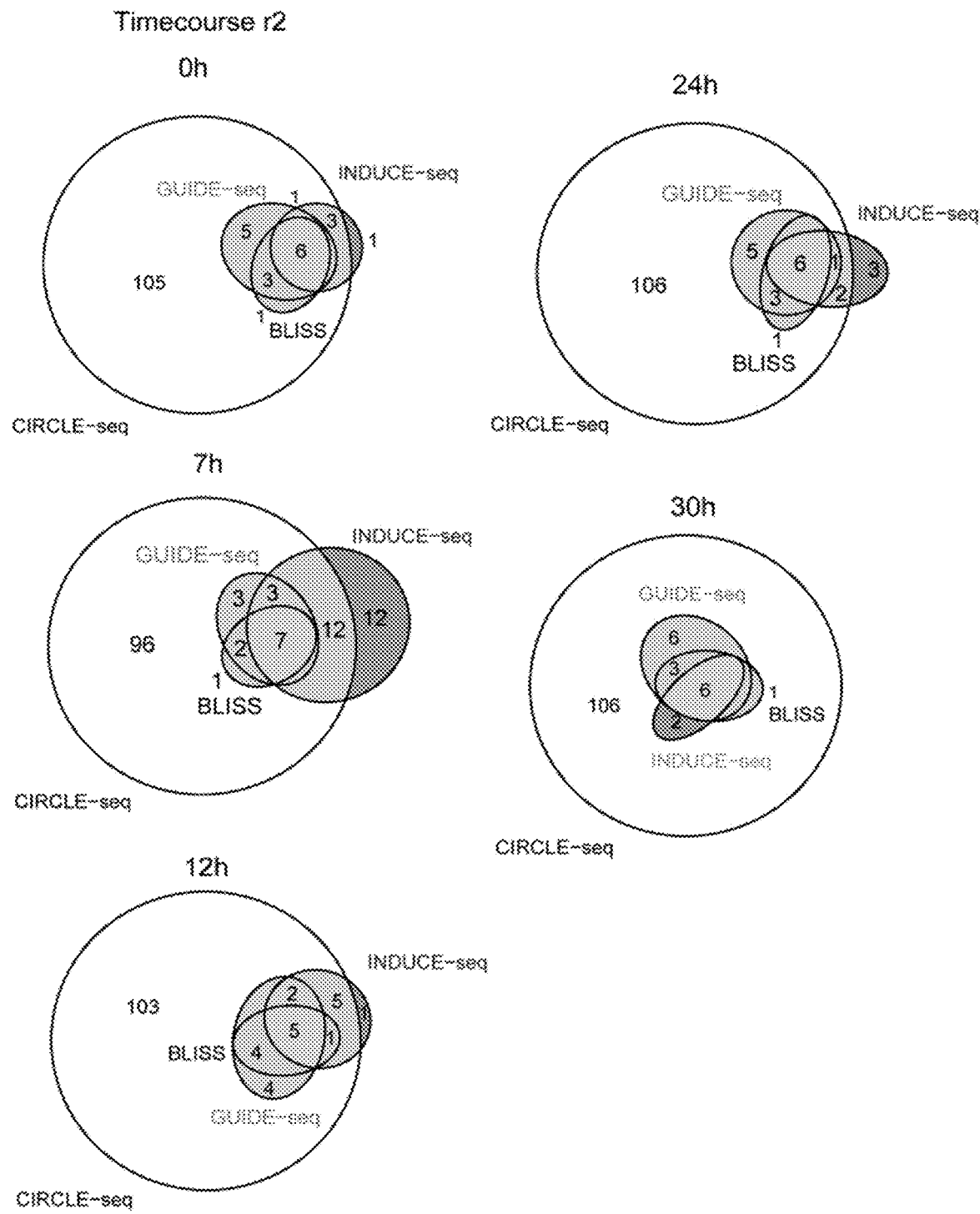
Figure 10C:
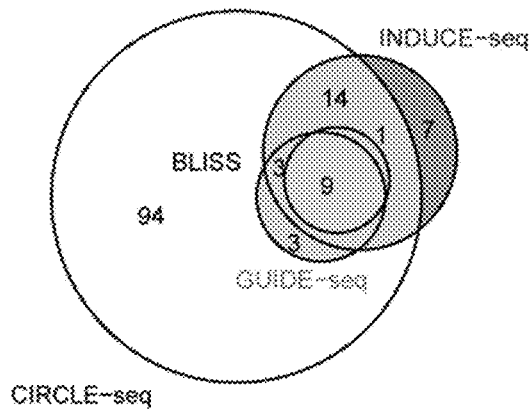
Figure 10D:
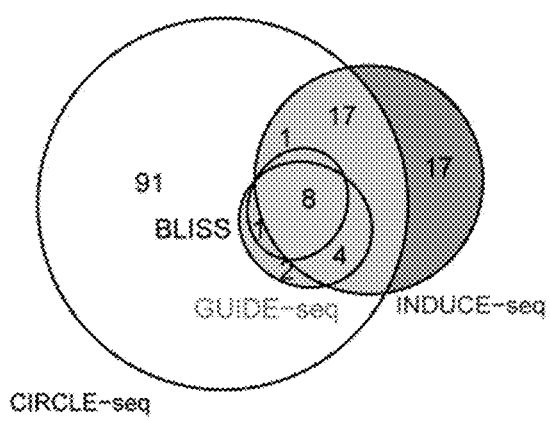
Figure 10E:
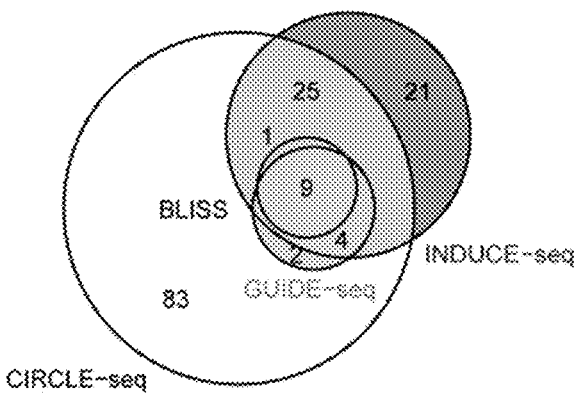

Having established the characteristics of break detection by INDUCE-seq, next we applied it to the detection of CRISPR/Cas9 induced on and off-target DSBs in the genome. This analysis is of central importance in safety profiling for the development of CRISPR-based therapies. Following RNP nucleofection of HEK293 cells with the extensively characterised EMX1 sgRNA, off-targets were determined at 0, 7, 12, 24 and 30 hours post nucleofection, as defined by a custom data analysis pipeline (FIG. 4a, FIG. 8, and FIG. 9). FIG. 3a also shows break number detected at the on-target and each of the 60 off-targets for EMX1, with mismatches varying from 2 bp to 6 bp compared to the target site.

Figure 4B:
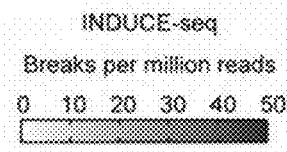
(FIG. 4b) INDUCE-seq reveals the kinetics of EMX1-induced DSB formation in a cell population. Quantification of the number of breaks detected per million reads for each sample revealed high Cas9 activity both on- and off-target immediately following cell nucleofection.
Figure 4C:
(FIG. 4c) The comparison between off-targets identified by INDUCE-seq with established in vitro methods CIRCLE-seq and Digenome-seq, in addition to cell-based methods GUIDE-seq, BLISS, and HTGTS. INDUCE-seq detects many off-targets that were previously only identifiable by in vitro approaches. Substantially more off-target sites were identified than by any of the current cell-based methods. INDUCE-seq also identifies multiple off-targets not detected by any other method.

This experiment reveals a profile of the kinetics of break induction by the EMX1 guide, offering insights into the mechanism of the CRISPR/Cas9 editing process. As shown in FIG. 4b, the majority of on- and off-target activity was observed immediately following nucleofection and during the early stages of the timecourse. These results demonstrate the rapidity of editing by this sgRNA. When compared to existing technologies, we find that INDUCE-seq significantly outperforms alternative cell-based methods GUIDE-seq, BLISS and HTGTS, as well as capturing several sites that were previously only identified using in vitro off-target discovery methodologies CIRCLE-seq and Digenome-seq. Importantly, INDUCE-seq also detects novel off-target break sites not previously detected by any other method (FIG. 4c and FIG. 10).

Figure 4D:
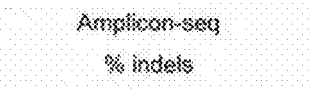
(FIG. 4d) Amplicon-sequencing to measure the indel frequency at INDUCE-seq identified off-targets. Amplicon sequencing could only identify 4 of the 60 off-targets identified by INDUCE-seq and is limited by the background indel false-discovery rate of 0.1%. These findings are consistent with previous studies that measured EMX1 off-target indel frequencies at 48 hours post EMX1 RNP nucleofection.
Figure 11A:
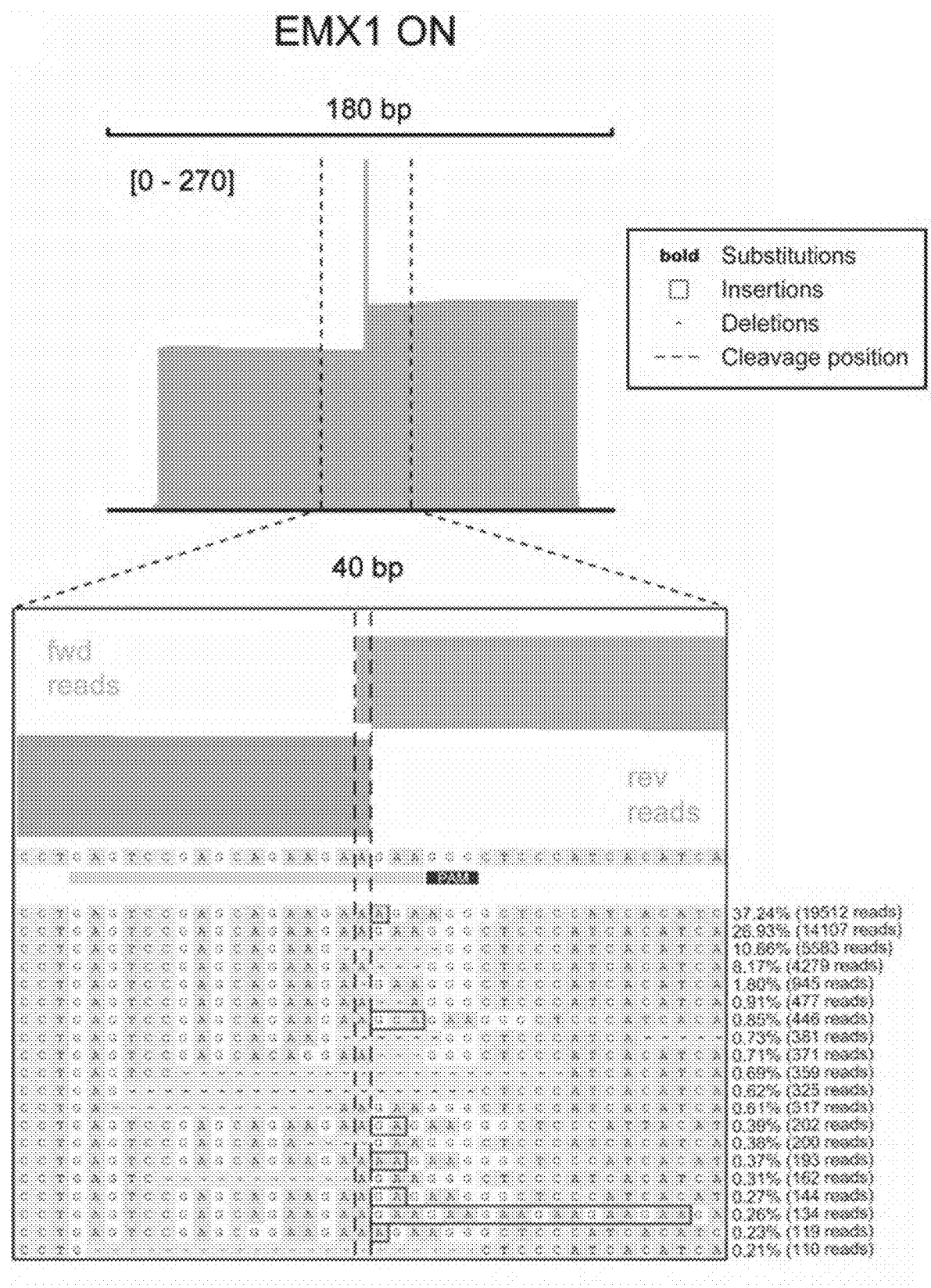
FIG. 11. The DSB pattern at CRISPR induced on- and off-targets correlates with editing outcome. Coverage tracks of the EMX1 on-target (FIG. 11a) and the top ranking off-targets (the displayed sequences in order from top to bottom, are SEQ ID NOs: 45-65), OT-1 (the displayed sequences in order from top to bottom, are SEQ ID NOs: 66-87) (FIG. 11b), and OT-2 (the displayed sequences in order from top to bottom, are SEQ ID NOs: 88-105) (FIG. 11c), spanning 180 bp. A close-up view of the 40 bp region surrounding each target site shows a distinct 1 bp overhanging cleavage pattern rather than the usual Cas9 induced blunt DSB. Corresponding indel spectra at each site shows the position of the mutations in relation to the observed break sites.
Figure 11B:
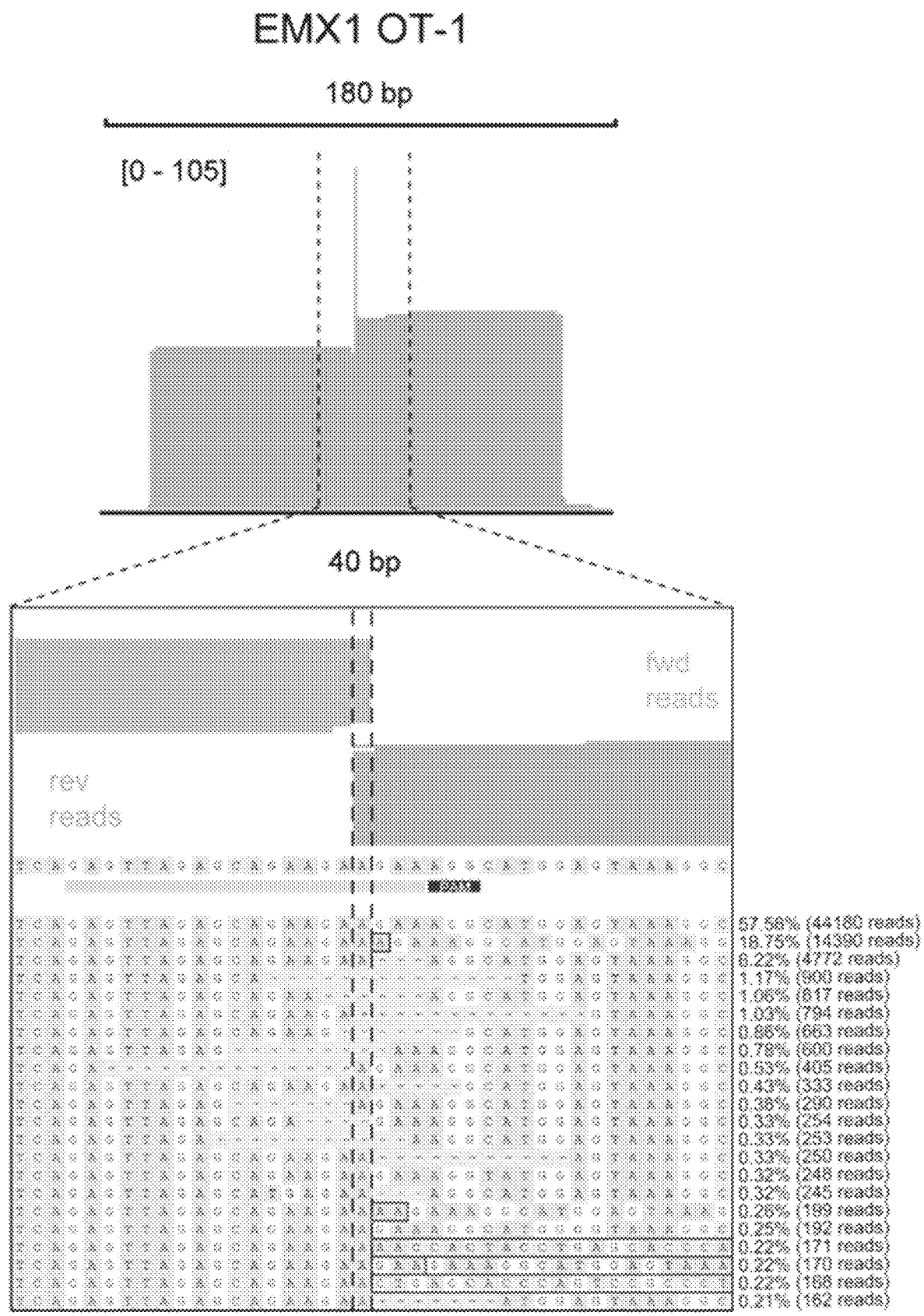
Figure 11C:
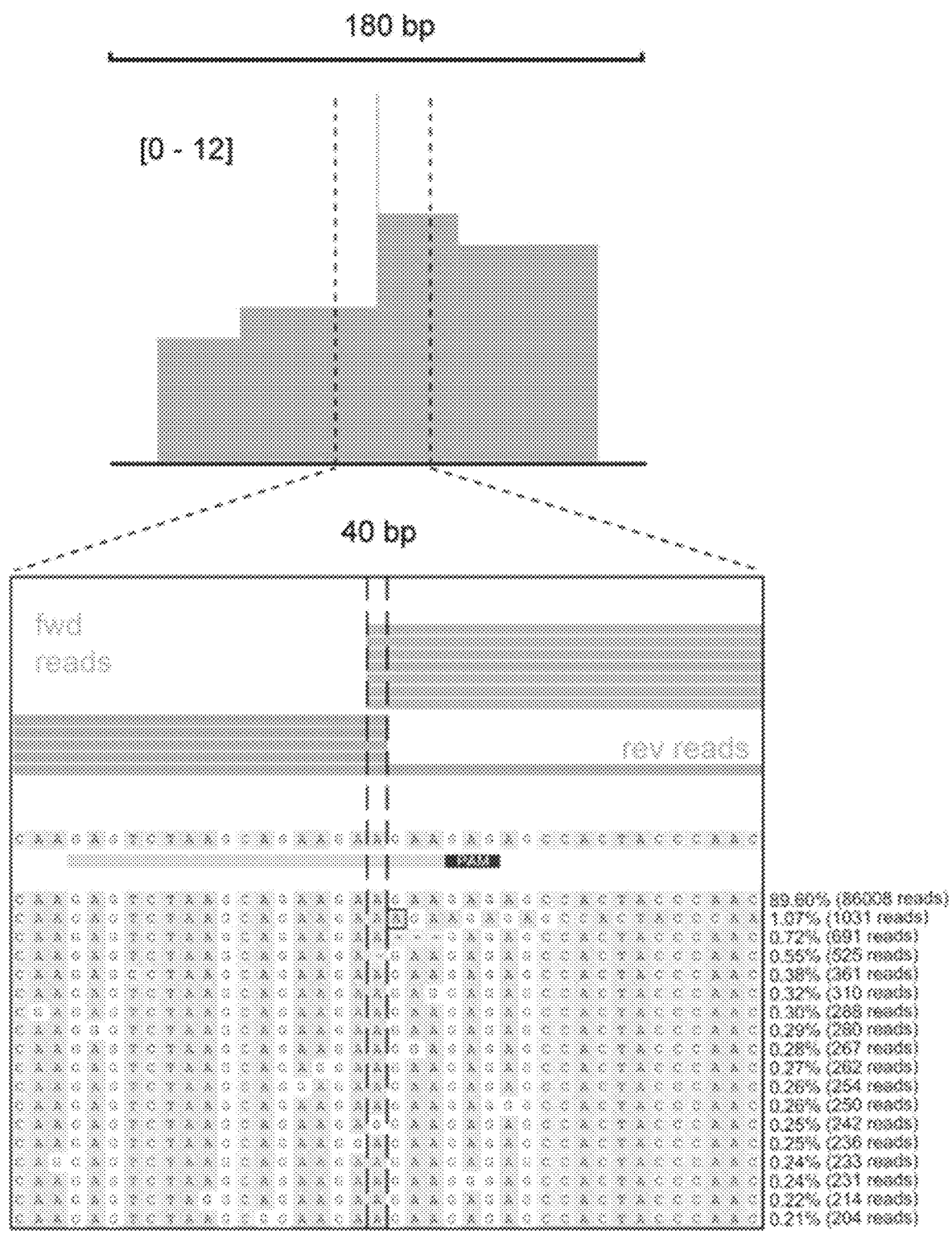

Finally, using DNA from the same samples, we measured the editing outcome at these on- and off-target breakage sites identified by INDUCE-seq, using amplicon sequencing. Amplicon sequencing is only able to detect indels above a background false-discovery rate of 0.1%. Therefore, evidence of editing was detected at the on-target, and only at four of the 60 off-target sites that were identified throughout the time course (FIG. 4d). This observation is in agreement with an identical previous study, which identified five off-targets with indel frequencies >0.1% at 48 hours post nucleofection of HEK293 cells with EMX1 RNP (FIG. 4d, far-right column, 48 h). This data demonstrates that INDUCE-seq can detect and quantify CRISPR induced off-target DSBs with a much greater sensitivity than is possible for the detection of indels using amplicon sequencing. This observation highlights the need for more sensitive methods for the detection of editing outcomes, in order to evaluate the safety of genome editing. Interestingly, close examination of the break pattern and the subsequent indel profile at both the on-target and the top two off-target sites, reveals a sgRNA-specific cleavage pattern that is reflected in, and correlates with, editing outcome (FIG. 11). This raises the possibility of using the DSB pattern observed at CRISPR-induced break sites to predict the eventual editing outcome at both the on- and off-target sites.

Discussion

We have developed a novel PCR-free methodology to prepare DNA libraries for next generation sequencing of DSBs in the genome. This enables the direct measurement of break ends in cells for the first time. Our approach overcomes the problem of poor signal-to-noise ratios for DSBs associated with PCR-amplification typically employed in standard NGS library preparations. The novel INDUCE-seq adaptor design essentially allows the sequencing flow cell to be used to enrich for the labelled DSB sequences, avoiding the need for their amplification. Improvement in the signal-to-noise ratio is achieved instead by filtering the noisy break ends generated during sample preparation that are not associated with genuine physiological DSBs found in cells. We demonstrate the characteristics of INDUCE-seq for measuring genomic DSBs in a range of different applications. We reveal its capability to sensitively and quantitatively detect low-level endogenous and high-level restriction enzyme-induced breaks simultaneously. This has not been possible previously without the need for complex and costly error-correction methods that have their own limitations and drawbacks. We compare our results with the currently available break detection methods to demonstrate how it improves on these, not only in terms of its accuracy and sensitivity, but also in terms of its simplicity, scalability, ease of use and cost effectiveness. These are all essential features of an assay that can be used to assess the safety profiling of synthetic guides for CRISPR genome editing. We demonstrate how INDUCE-seq performs compared to several of the current DSB detection methods for the detection of both on- and off-target editing by the EMX1 sgRNA. We reveal that in addition to detecting many of the off-target sites measured cumulatively by five other methods, INDUCE-seq also identifies a significant number of novel off-target sites that current methods are unable to detect. We suggest that INDUCE-seq could be a very important method for safety profiling and synthetic guide RNA design for the future development of genome editing as a therapeutic modality. Such features include genome-wide mutations, single strand breaks and gaps, as well as other types of DNA damage that can be converted into breaks. The development of INDUCE-seq and its derivative assays could have significant implications in a range of different biomedical applications.

TABLE 1

| Primer Pair | Sequence (5'-3') | Identifier |
|---|---|---|
| First Primer Pair (P5 Adaptor) | P-GATCGGAAGAGCGTCGTGTAGGGAAAGAGTGTAGATCTCGGTGGTCGCCGTATCATTC /3SpC3/ | SEQ ID NO: 1 |
| | A*ATGATACGGCGACCACCGAGATCTACACTCTTTCCCTACACGACGCTCTTCCGATC*T | SEQ ID NO: 2 |
| Second Primer Pair (P7 Adaptor) | P-GATCGGAAGAGCACACGTCTGAACTCCAGTCAC/3SpC3/ | SEQ ID NO: 3 |
| | C*AAGCAGAAGACGGCATACGAGAT[INDEX]GTGACTGGAGTTCAGACGTGTGCTCTTCCGATC*T | SEQ ID NO: 4 |
| | C*AAGCAGAAGACGGCATACGAGATCGTGATGTGACTGGAGTTCAGACGTGTGCTCTTCCGATC*T | SEQ ID NO: 5 |
| | C*AAGCAGAAGACGGCATACGAGATACATCGGTGACTGGAGTTCAGACGTGTGCTCTTCCGATC*T | SEQ ID NO: 6 |
| | C*AAGCAGAAGACGGCATACGAGATGCCTAAGTGACTGGAGTTCAGACGTGTGCTCTTCCGATC*T | SEQ ID NO: 7 |
| | C*AAGCAGAAGACGGCATACGAGATTGGTCAGTGACTGGAGTTCAGACGTGTGCTCTTCCGATC*T | SEQ ID NO: 8 |
| | C*AAGCAGAAGACGGCATACGAGATCACTGTGTGACTGGAGTTCAGACGTGTGCTCTTCCGATC*T | SEQ ID NO: 9 |
| | C*AAGCAGAAGACGGCATACGAGATATTGGCGTGACTGGAGTTCAGACGTGTGCTCTTCCGATC*T | SEQ ID NO: 10 |
| | C*AAGCAGAAGACGGCATACGAGATGATCTGGTGACTGGAGTTCAGACGTGTGCTCTTCCGATC*T | SEQ ID NO: 11 |
| | C*AAGCAGAAGACGGCATACGAGATTCAAGTGTGACTGGAGTTCAGACGTGTGCTCTTCCGATC*T | SEQ ID NO: 12 |
| | C*AAGCAGAAGACGGCATACGAGATCTGATCGTGACTGGAGTTCAGACGTGTGCTCTTCCGATC*T | SEQ ID NO: 13 |
| | C*AAGCAGAAGACGGCATACGAGATAAGCTAGTGACTGGAGTTCAGACGTGTGCTCTTCCGATC*T | SEQ ID NO: 14 |
| | C*AAGCAGAAGACGGCATACGAGATGTAGCCGTGACTGGAGTTCAGACGTGTGCTCTTCCGATC*T | SEQ ID NO: 15 |
| | C*AAGCAGAAGACGGCATACGAGATTACAAGGTGACTGGAGTTCAGACGTGTGCTCTTCCGATC*T | SEQ ID NO: 16 |
| | C*AAGCAGAAGACGGCATACGAGATTGTTGACTGTGACTGGAGTTCAGACGTGTGCTCTTCCGATC*T | SEQ ID NO: 17 |
| | C*AAGCAGAAGACGGCATACGAGATACGAACTGTGACTGGAGTTCAGACGTGTGCTCTTCCGATC*T | SEQ ID NO: 18 |
| | C*AAGCAGAAGACGGCATACGAGATTCTGACATGTGACTGGAGTTCAGACGTGTGCTCTTCCGATC*T | SEQ ID NO: 19 |
| | C*AAGCAGAAGACGGCATACGAGATCGGGACGGGTGACTGGAGTTCAGACGTGTGCTCTTCCGATC*T | SEQ ID NO: 20 |
| | C*AAGCAGAAGACGGCATACGAGATGTGCGGACGTGACTGGAGTTCAGACGTGTGCTCTTCCGATC*T | SEQ ID NO: 21 |
| | C*AAGCAGAAGACGGCATACGAGATCGTTTCACGTGACTGGAGTTCAGACGTGTGCTCTTCCGATC*T | SEQ ID NO: 22 |
| | C*AAGCAGAAGACGGCATACGAGATAAGGCCACGTGACTGGAGTTCAGACGTGTGCTCTTCCGATC*T | SEQ ID NO: 23 |
| | C*AAGCAGAAGACGGCATACGAGATTCCGAAACGTGACTGGAGTTCAGACGTGTGCTCTTCCGATC*T | SEQ ID NO: 24 |
| | C*AAGCAGAAGACGGCATACGAGATTACGTACGGTGACTGGAGTTCAGACGTGTGCTCTTCCGATC*T | SEQ ID NO: 25 |
| | C*AAGCAGAAGACGGCATACGAGATATCCACTCGTGACTGGAGTTCAGACGTGTGCTCTTCCGATC*T | SEQ ID NO: 26 |
| | C*AAGCAGAAGACGGCATACGAGATATATCAGTGTGACTGGAGTTCAGACGTGTGCTCTTCCGATC*T | SEQ ID NO: 27 |
| | C*AAGCAGAAGACGGCATACGAGATAAAGGAATGTGACTGGAGTTCAGACGTGTGCTCTTCCGATC*T | SEQ ID NO: 28 |

*Phosphorothioate linkage Resistance to exonuclease activity
/3SpC3/ C3 Spacer phosphoramidite (covalent block)
Resistance to exonuclease, ligase, and 5' >3 ' polymerase activity
-P 5' Phosphate group Facilitate 5' ligation
INDEX Illumina sequencing index sequence Enable demultiplexing of pooled sequencing libraries
*T 3' deoxythymidine triphosphate 'T-tail' with phosphorothioate linkage Provide substrate for ligation to 'A-tailed' DNA fragments

TABLE 2

| Oligo modification (P5 or P7 adaptor) | Activity |
| --- | --- |
| Phosphorothioate linkages (5' and 3' ends of oligo) | Resist 5' > 3' and 3' > 5' exonuclease activity. |
| Phosphorothioate linkages (throughout oligo) | Resist endonuclease activity. |
| C3 Spacer phosphoramidite (3') | Resist exonuclease, ligase, terminal transferase, 5' > 3' polymerase activity. |
| 3' Phosphate group | Inhibit degradation by some 3'-exonucleases, can be used to block extension by DNA polymerases, and resist ligation. |
| 2'-O-Methyl (2'OMe) | DNA oligonucleotides that include this modification are typically 5-to 10-fold less susceptible to DNases than unmodified DNA. |
| Inverted dT (3') | Inverted dT at 3' end of an oligonucleotide leads to a 3'-3' linkage that will inhibit degradation by 3' exonucleases and extension by DNA polymerases. |
| 5' Inverted ddT | 5' Inverted ddT at the 5' end of an oligonucleotide resists ligation and may provide resistance to some forms of exonuclease. |
| Locked nucleic acid bases | Increases melting temperature of oligo and prevents spurious hybridisation, increases binding specificity. |
| Dideoxycytidine (ddC) (3') | 3' chain terminator that prevents 3' extension by polymerases. |

REFERENCES

Andrews, S. (2010). *FastQC: a quality control tool for high throughput sequence data.* Available at: www.bioinformatics.babraham.ac.uk/projects/fastqc [Accessed: 2019].

Bae, S., Park, J. and Kim, J. S. (2014). Cas-OFFinder: a fast and versatile algorithm that searches for potential off-target sites of Cas9 RNA-guided endonucleases. *Bioinformatics* 30 (10): 1473-1475.

Krueger, F. (2015). *Trim Galore: A wrapper tool around Cutadapt and FastQC to consistently apply quality and adapter trimming to FastQ files.* Available at: www.bioinformatics.babraham.ac.uk/projects/trim_galore/ [Accessed: 2019].

Lensing, S. V., Marsico, G., Hansel-Hertsch, R., Lam, E. Y., Tannahill, D. and Balasubramanian, S. (2016). DSBCapture: in situ capture and sequencing of DNA breaks. *Nature Methods* 13 (10): 855-+.

Li, H. and Durbin, R. (2009). Fast and accurate short read alignment with Burrows-Wheeler transform. *Bioinformatics* 25 (14): 1754-1760.

Li, H., Handsaker, B., Wysoker, A., Fennell, T., Ruan, J., Homer, N., . . . . Genome Project Data, P. (2009). The Sequence Alignment/Map format and SAMtools. *Bioinformatics* 25 (16): 2078-2079.

Pinello, L., Canver, M. C., Hoban, M. D., Orkin, S. H., Kohn, D. B., Bauer, D. E. and Yuan, G. C. (2016). Analyzing CRISPR genome-editing experiments with CRISPResso. *Nature Biotechnology* 34 (7): 695-697.

Quinlan, A. R. and Hall, I. M. (2010). BEDTools: a flexible suite of utilities for comparing genomic features. *Bioinformatics* 26 (6): 841-842.

Shen, W., Le, S., Li, Y. and Hu, F. Q. (2016). SeqKit: A Cross-Platform and Ultrafast Toolkit for FASTA/Q File Manipulation. *Plos One* 11 (10).

Yan, W. X., Mirzazadeh, R., Garnerone, S., Scott, D., Schneider, M. W., Kallas, T., . . . Crosetto, N. (2017). BLISS is a versatile and quantitative method for genome-wide profiling of DNA double-strand breaks. *Nature Communications* 8.

The invention claimed is:

1. A method of sample preparation for identifying DNA double-strand breaks (DSBs) in a nucleic acid sample, wherein the preparation comprises modifying DSB-associated nucleic acids to be capable of binding to a substrate comprising at least a first immobilised primer, the method comprising:
   a) providing a sample comprising a plurality of nucleic acids;
   b) exposing the plurality of nucleic acids to a first adaptor pair under conditions conducive to ligation, wherein the first adaptor pair comprises first and second oligonucleotides that are at least partially complementary to each other, and the first oligonucleotide is ligatable to a 3' terminus of a strand of a DSB and comprises a sequence that is capable of binding to the first immobilised primer by hybridisation;
   c) fragmenting the plurality of nucleic acids; and
   d) exposing the plurality of nucleic acids to a second adaptor pair under conditions conducive to ligation, wherein the second adaptor pair is capable of being ligated to at least a 5' terminus of a strand at a break induced by fragmentation but is not capable of being ligated to the first oligonucleotide of the first adaptor pair, wherein the second adaptor pair comprises first and second oligonucleotides that are partially complementary to each other, and the first oligonucleotide is ligatable to a 5' terminus and comprises a sequence identical to a region of a second primer, and the second oligonucleotide does not comprise a sequence that is complementary to said sequence identical to a region of the second primer.

2. The method of claim 1, wherein the method comprises modification of the DSB-associated nucleic acids to be capable of amplification, wherein the amplification comprises the use of the first immobilised primer and the second primer.

3. The method of claim 1, wherein the second primer is a second immobilised primer comprised by the substrate.

4. The method of claim 3, wherein the method comprises modification of the DSB-associated nucleic acids to be capable of amplification, wherein the amplification comprises the use of the first immobilised primer and the second immobilised primer.

5. The method of claim 4, wherein the amplification is bridge amplification.

6. The method of claim 1, wherein the second adaptor pair comprises the first oligonucleotide comprising a sequence according to CAAGCAGAAGACGGCATACGAGAT (SEQ ID NO: 32), and the second oligonucleotide comprising a sequence that does not comprise a sequence of more than 5, 10, 15, or 20 bases, or does not comprise all 24 bases, of the sequence ATCTCGTATGCCGTCTTCTGCTTG (SEQ ID NO: 30).

7. The method of claim 1, wherein the second adaptor pair comprises the first oligonucleotide comprising a sequence according to AATGATACGGCGACCACCGA (SEQ ID NO: 34), and the second oligonucleotide comprising a sequence that does not comprise a sequence of more than 5, 10, or 15 bases, or does not comprise all 20 bases, of the sequence TCGGTGGTCGCCGTATCATT (SEQ ID NO: 31).

8. The method of claim 1, wherein the first oligonucleotide of the first adaptor pair comprises a 3' protective feature; and/or wherein the second oligonucleotide of the second adaptor pair comprises a 3' protective feature.

9. The method of claim 1, wherein the second adaptor pair is not capable of being ligated to the first adaptor pair due to the presence of a 3' modification of the first adaptor pair.

10. The method of claim 1, wherein the oligonucleotide of the second adaptor pair that is ligatable to a 5' terminus comprises a sequence identical to 5, 10, 15, 20, 21, 24, or more bases of the second primer.

11. The method of claim 1, further comprising denaturing the plurality of nucleic acids to form a plurality of single-stranded nucleic acids.

12. The method of claim 1, further comprising contacting the plurality of nucleic acids with the substrate comprising immobilised primers under conditions suitable for hybridisation of the immobilised primers to complementary nucleic acids.

13. The method of claim 12, further comprising obtaining sequence information for any nucleic acids hybridised to the substrate.

14. The method of claim 1, wherein said sample comprising a plurality of nucleic acids is genomic DNA (gDNA).

15. The method of claim 1, wherein the steps are performed in the order a), b), c), and then d).

16. The method of claim 15, wherein the sample is exposed to conditions capable of causing a DSB at a feature in the nucleic acid sample prior to step b).

17. The method of claim 1, wherein the steps are performed in the order a), c), d), and then b), wherein the sample is exposed to conditions capable of causing or suspected of being capable of causing a DSB between steps d) and b).

18. The method of claim 17, wherein the sample is exposed to conditions capable of causing a DSB at a feature in the nucleic acid sample.

19. The method of claim 1, wherein said ligation in step b) occurs in situ or in vitro using a cell or tissue sample.

20. The method of claim 1, wherein the first adaptor pair comprises a first hybridization site to which a first sequencing primer can bind and/or the second adaptor pair comprises a second hybridization site to which a second sequencing primer can bind.

* * * * *

SEQUENCE LISTING

```
Sequence total quantity: 111
SEQ ID NO: 1            moltype = DNA  length = 58
FEATURE                 Location/Qualifiers
misc_feature            1..58
                        note = Adaptor Sequence
source                  1..58
                        mol_type = other DNA
                        organism = synthetic construct
SEQUENCE: 1
gatcggaaga gcgtcgtgta gggaaagagt gtagatctcg gtggtcgccg tatcattc      58

SEQ ID NO: 2            moltype = DNA  length = 58
FEATURE                 Location/Qualifiers
misc_feature            1..58
                        note = Adaptor Sequence
source                  1..58
                        mol_type = other DNA
                        organism = synthetic construct
SEQUENCE: 2
aatgatacgg cgaccaccga gatctacact ctttccctac acgacgctct tccgatct      58

SEQ ID NO: 3            moltype = DNA  length = 33
FEATURE                 Location/Qualifiers
```

```
misc_feature            1..33
                        note = Adaptor Sequence
source                  1..33
                        mol_type = other DNA
                        organism = synthetic construct
SEQUENCE: 3
gatcggaaga gcacacgtct gaactccagt cac                                    33

SEQ ID NO: 4            moltype = DNA  length = 64
FEATURE                 Location/Qualifiers
misc_feature            1..64
                        note = Adaptor Sequence
misc_difference         25..30
                        note = n is a, c, g, or t
source                  1..64
                        mol_type = other DNA
                        organism = synthetic construct
SEQUENCE: 4
caagcagaag acggcatacg agatnnnnnn gtgactggag ttcagacgtg tgctcttccg        60
atct                                                                    64

SEQ ID NO: 5            moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 5
caagcagaag acggcatacg agatcgtgat gtgactggag ttcagacgtg tgctcttccg        60
atct                                                                    64

SEQ ID NO: 6            moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 6
caagcagaag acggcatacg agatacatcg gtgactggag ttcagacgtg tgctcttccg        60
atct                                                                    64

SEQ ID NO: 7            moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 7
caagcagaag acggcatacg agatgcctaa gtgactggag ttcagacgtg tgctcttccg        60
atct                                                                    64

SEQ ID NO: 8            moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 8
caagcagaag acggcatacg agattggtca gtgactggag ttcagacgtg tgctcttccg        60
atct                                                                    64

SEQ ID NO: 9            moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 9
caagcagaag acggcatacg agatcactgt gtgactggag ttcagacgtg tgctcttccg        60
atct                                                                    64

SEQ ID NO: 10           moltype = DNA  length = 64
FEATURE                 Location/Qualifiers
misc_feature            1..64
```

```
                        note = Adaptor Sequence
source                  1..64
                        mol_type = other DNA
                        organism = synthetic construct
SEQUENCE: 10
caagcagaag acggcatacg agatattggc gtgactggag ttcagacgtg tgctcttccg    60
atct                                                                 64

SEQ ID NO: 11           moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 11
caagcagaag acggcatacg agatgatctg gtgactggag ttcagacgtg tgctcttccg    60
atct                                                                 64

SEQ ID NO: 12           moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 12
caagcagaag acggcatacg agattcaagt gtgactggag ttcagacgtg tgctcttccg    60
atct                                                                 64

SEQ ID NO: 13           moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 13
caagcagaag acggcatacg agatctgatc gtgactggag ttcagacgtg tgctcttccg    60
atct                                                                 64

SEQ ID NO: 14           moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 14
caagcagaag acggcatacg agataagcta gtgactggag ttcagacgtg tgctcttccg    60
atct                                                                 64

SEQ ID NO: 15           moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 15
caagcagaag acggcatacg agatgtagcc gtgactggag ttcagacgtg tgctcttccg    60
atct                                                                 64

SEQ ID NO: 16           moltype = DNA  length = 64
FEATURE                 Location/Qualifiers
misc_feature            1..64
                        note = Adaptor Sequence
source                  1..64
                        mol_type = other DNA
                        organism = synthetic construct
SEQUENCE: 16
caagcagaag acggcatacg agattacaag gtgactggag ttcagacgtg tgctcttccg    60
atct                                                                 64

SEQ ID NO: 17           moltype = DNA  length = 66
FEATURE                 Location/Qualifiers
misc_feature            1..66
                        note = Adaptor Sequence
source                  1..66
```

```
                        mol_type = other DNA
                        organism = synthetic construct
SEQUENCE: 17
caagcagaag acggcatacg agattgttga ctgtgactgg agttcagacg tgtgctcttc    60
cgatct                                                              66

SEQ ID NO: 18           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 18
caagcagaag acggcatacg agatacggaa ctgtgactgg agttcagacg tgtgctcttc    60
cgatct                                                              66

SEQ ID NO: 19           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 19
caagcagaag acggcatacg agattctgac atgtgactgg agttcagacg tgtgctcttc    60
cgatct                                                              66

SEQ ID NO: 20           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 20
caagcagaag acggcatacg agatcgggac gggtgactgg agttcagacg tgtgctcttc    60
cgatct                                                              66

SEQ ID NO: 21           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 21
caagcagaag acggcatacg agatgtgcgg acgtgactgg agttcagacg tgtgctcttc    60
cgatct                                                              66

SEQ ID NO: 22           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 22
caagcagaag acggcatacg agatcgtttc acgtgactgg agttcagacg tgtgctcttc    60
cgatct                                                              66

SEQ ID NO: 23           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 23
caagcagaag acggcatacg agataaggcc acgtgactgg agttcagacg tgtgctcttc    60
cgatct                                                              66

SEQ ID NO: 24           moltype = DNA   length = 66
FEATURE                 Location/Qualifiers
misc_feature            1..66
                        note = Adaptor Sequence
source                  1..66
                        mol_type = other DNA
                        organism = synthetic construct
```

```
SEQUENCE: 24
caagcagaag acggcatacg agattccgaa acgtgactgg agttcagacg tgtgctcttc    60
cgatct                                                               66

SEQ ID NO: 25           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 25
caagcagaag acggcatacg agattacgta cggtgactgg agttcagacg tgtgctcttc    60
cgatct                                                               66

SEQ ID NO: 26           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 26
caagcagaag acggcatacg agatatccac tcgtgactgg agttcagacg tgtgctcttc    60
cgatct                                                               66

SEQ ID NO: 27           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 27
caagcagaag acggcatacg agatatatca gtgtgactgg agttcagacg tgtgctcttc    60
cgatct                                                               66

SEQ ID NO: 28           moltype = DNA   length = 66
FEATURE                 Location/Qualifiers
misc_feature            1..66
                        note = Adaptor Sequence
source                  1..66
                        mol_type = other DNA
                        organism = synthetic construct
SEQUENCE: 28
caagcagaag acggcatacg agataaagga atgtgactgg agttcagacg tgtgctcttc    60
cgatct                                                               66

SEQ ID NO: 29           moltype = DNA   length = 20
FEATURE                 Location/Qualifiers
misc_feature            1..20
                        note = gRNA targeting EMX1
source                  1..20
                        mol_type = other DNA
                        organism = synthetic construct
SEQUENCE: 29
gagtccgagc agaagaagaa                                                20

SEQ ID NO: 30           moltype = DNA   length = 24
FEATURE                 Location/Qualifiers
misc_feature            1..24
                        note = Adaptor Sequence - optionally not present
source                  1..24
                        mol_type = other DNA
                        organism = synthetic construct
SEQUENCE: 30
atctcgtatg ccgtcttctg cttg                                           24

SEQ ID NO: 31           moltype = DNA   length = 20
FEATURE                 Location/Qualifiers
misc_feature            1..20
                        note = Adaptor Sequence - optionally not present
source                  1..20
                        mol_type = other DNA
                        organism = synthetic construct
SEQUENCE: 31
tcggtggtcg ccgtatcatt                                                20

SEQ ID NO: 32           moltype = DNA   length = 24
```

```
FEATURE                Location/Qualifiers
misc_feature           1..24
                       note = Adaptor Sequence
source                 1..24
                       mol_type = other DNA
                       organism = synthetic construct
SEQUENCE: 32
caagcagaag acggcatacg agat                                              24

SEQ ID NO: 33          moltype = DNA   length = 34
FEATURE                Location/Qualifiers
misc_feature           1..34
                       note = Adaptor Sequence
source                 1..34
                       mol_type = other DNA
                       organism = synthetic construct
SEQUENCE: 33
gtgactggag ttcagacgtg tgctcttccg atct                                   34

SEQ ID NO: 34          moltype = DNA   length = 20
FEATURE                Location/Qualifiers
misc_feature           1..20
                       note = Adaptor Sequence
source                 1..20
                       mol_type = other DNA
                       organism = synthetic construct
SEQUENCE: 34
aatgatacgg cgaccaccga                                                   20

SEQ ID NO: 35          moltype = DNA   length = 18
FEATURE                Location/Qualifiers
misc_feature           1..18
                       note = HindIII target site
source                 1..18
                       mol_type = other DNA
                       organism = synthetic construct
SEQUENCE: 35
tactcaagct taccccta                                                     18

SEQ ID NO: 36          moltype = DNA   length = 22
FEATURE                Location/Qualifiers
misc_feature           1..22
                       note = Adaptor Sequence - optionally may be absent
source                 1..22
                       mol_type = other DNA
                       organism = synthetic construct
SEQUENCE: 36
ggaaagcgga ggcgtagtgg tt                                                22

SEQ ID NO: 37          moltype = DNA   length = 32
FEATURE                Location/Qualifiers
misc_feature           1..32
                       note = Adaptor Sequence
source                 1..32
                       mol_type = other DNA
                       organism = synthetic construct
SEQUENCE: 37
gatcggaaga gcgtcgtgta gggaaagagt gt                                     32

SEQ ID NO: 38          moltype = DNA   length = 21
FEATURE                Location/Qualifiers
misc_feature           1..21
                       note = Adaptor Sequence
source                 1..21
                       mol_type = other DNA
                       organism = synthetic construct
SEQUENCE: 38
tcggtggtcg ccgtatcatt c                                                 21

SEQ ID NO: 39          moltype = DNA   length = 33
FEATURE                Location/Qualifiers
misc_feature           1..33
                       note = Adaptor Sequence
source                 1..33
                       mol_type = other DNA
                       organism = synthetic construct
SEQUENCE: 39
acactctttc cctacacgac gctcttccga tct                                    33
```

```
SEQ ID NO: 40          moltype = DNA  length = 23
FEATURE                Location/Qualifiers
misc_feature           1..23
                       note = Adaptor Sequence
source                 1..23
                       mol_type = other DNA
                       organism = synthetic construct
SEQUENCE: 40
aacccactac gcctccgctt tcc                                              23

SEQ ID NO: 41          moltype = DNA  length = 29
FEATURE                Location/Qualifiers
misc_feature           1..29
                       note = Adaptor Sequence
source                 1..29
                       mol_type = other DNA
                       organism = synthetic construct
SEQUENCE: 41
aatgatacgg cgaccaccga gatctacac                                        29

SEQ ID NO: 42          moltype = DNA  length = 29
FEATURE                Location/Qualifiers
misc_feature           1..29
                       note = Adaptor Sequence
source                 1..29
                       mol_type = other DNA
                       organism = synthetic construct
SEQUENCE: 42
gtgtagatct cggtggtcgc cgtatcatt                                        29

SEQ ID NO: 43          moltype = DNA  length = 18
FEATURE                Location/Qualifiers
misc_feature           1..18
                       note = HindIII target site
source                 1..18
                       mol_type = other DNA
                       organism = synthetic construct
SEQUENCE: 43
gggggggtaag cttgagta                                                   18

SEQ ID NO: 44          moltype = DNA  length = 23
FEATURE                Location/Qualifiers
misc_feature           1..23
                       note = EMX1 sgRNA target site
misc_difference        21
                       note = n is a, c, g, or t
source                 1..23
                       mol_type = other DNA
                       organism = synthetic construct
SEQUENCE: 44
gagtccgagc agaagaagaa ngg                                              23

SEQ ID NO: 45          moltype = DNA  length = 40
FEATURE                Location/Qualifiers
misc_feature           1..40
                       note = EMX1 ON read
source                 1..40
                       mol_type = other DNA
                       organism = synthetic construct
SEQUENCE: 45
cctgagtccg agcagaagaa gaagggctcc catcacatca                            40

SEQ ID NO: 46          moltype = DNA  length = 40
FEATURE                Location/Qualifiers
misc_feature           1..40
                       note = EMX1 ON read
source                 1..40
                       mol_type = other DNA
                       organism = synthetic construct
SEQUENCE: 46
cctgagtccg agcagaagaa agaagggctc ccatcacatc                            40

SEQ ID NO: 47          moltype = DNA  length = 40
FEATURE                Location/Qualifiers
misc_feature           1..40
                       note = EMX1 ON read
source                 1..40
                       mol_type = other DNA
                       organism = synthetic construct
```

```
SEQUENCE: 47
cctgagtccg agcagaagaa gaagggctcc catcacatca                              40

SEQ ID NO: 48            moltype = DNA   length = 34
FEATURE                  Location/Qualifiers
misc_feature             1..34
                         note = EMX1 ON read
source                   1..34
                         mol_type = other DNA
                         organism = synthetic construct
SEQUENCE: 48
cctgagtccg agcagaaggg ctcccatcac atca                                    34

SEQ ID NO: 49            moltype = DNA   length = 37
FEATURE                  Location/Qualifiers
misc_feature             1..37
                         note = EMX1 ON read
source                   1..37
                         mol_type = other DNA
                         organism = synthetic construct
SEQUENCE: 49
cctgagtccg agcagaagaa gggctcccat cacatca                                 37

SEQ ID NO: 50            moltype = DNA   length = 39
FEATURE                  Location/Qualifiers
misc_feature             1..39
                         note = EMX1 ON read
source                   1..39
                         mol_type = other DNA
                         organism = synthetic construct
SEQUENCE: 50
cctgagtccg agcagaagag aagggctccc atcacatca                               39

SEQ ID NO: 51            moltype = DNA   length = 38
FEATURE                  Location/Qualifiers
misc_feature             1..38
                         note = EMX1 ON read
source                   1..38
                         mol_type = other DNA
                         organism = synthetic construct
SEQUENCE: 51
cctgagtccg agcagaagaa agggctccca tcacatca                                38

SEQ ID NO: 52            moltype = DNA   length = 40
FEATURE                  Location/Qualifiers
misc_feature             1..40
                         note = EMX1 ON read
source                   1..40
                         mol_type = other DNA
                         organism = synthetic construct
SEQUENCE: 52
cctgagtccg agcagaagaa gcagaagggc tcccatcaca                              40

SEQ ID NO: 53            moltype = DNA   length = 29
FEATURE                  Location/Qualifiers
misc_feature             1..29
                         note = EMX1 ON read
source                   1..29
                         mol_type = other DNA
                         organism = synthetic construct
SEQUENCE: 53
cctgagtccg agcagaaggg ctcccatca                                          29

SEQ ID NO: 54            moltype = DNA   length = 37
FEATURE                  Location/Qualifiers
misc_feature             1..37
                         note = EMX1 ON read
source                   1..37
                         mol_type = other DNA
                         organism = synthetic construct
SEQUENCE: 54
cctgagtccg agcacaggaa gggctcccat cacatca                                 37

SEQ ID NO: 55            moltype = DNA   length = 18
FEATURE                  Location/Qualifiers
misc_feature             1..18
                         note = EMX1 ON read
source                   1..18
                         mol_type = other DNA
```

```
                        organism = synthetic construct
SEQUENCE: 55
cctgagtcca tcacatca                                                           18

SEQ ID NO: 56           moltype = DNA  length = 20
FEATURE                 Location/Qualifiers
misc_feature            1..20
                        note = EMX1 ON read
source                  1..20
                        mol_type = other DNA
                        organism = synthetic construct
SEQUENCE: 56
cctgagctcc catcacatca                                                         20

SEQ ID NO: 57           moltype = DNA  length = 27
FEATURE                 Location/Qualifiers
misc_feature            1..27
                        note = EMX1 ON read
source                  1..27
                        mol_type = other DNA
                        organism = synthetic construct
SEQUENCE: 57
cctgaaagaa gggctcccat cacatca                                                 27

SEQ ID NO: 58           moltype = DNA  length = 40
FEATURE                 Location/Qualifiers
misc_feature            1..40
                        note = EMX1 ON read
source                  1..40
                        mol_type = other DNA
                        organism = synthetic construct
SEQUENCE: 58
cctgagtccg agcagaagaa gagaagggct cccattacat                                   40

SEQ ID NO: 59           moltype = DNA  length = 36
FEATURE                 Location/Qualifiers
misc_feature            1..36
                        note = EMX1 ON read
source                  1..36
                        mol_type = other DNA
                        organism = synthetic construct
SEQUENCE: 59
cctgagtccg agcagagaag ggctcccatc acatca                                       36

SEQ ID NO: 60           moltype = DNA  length = 40
FEATURE                 Location/Qualifiers
misc_feature            1..40
                        note = EMX1 ON read
source                  1..40
                        mol_type = other DNA
                        organism = synthetic construct
SEQUENCE: 60
cctgagtccg agcagaagaa aagaagggct cccatcacat                                   40

SEQ ID NO: 61           moltype = DNA  length = 29
FEATURE                 Location/Qualifiers
misc_feature            1..29
                        note = EMX1 ON read
source                  1..29
                        mol_type = other DNA
                        organism = synthetic construct
SEQUENCE: 61
cctgagtcag aagggctccc atcacatca                                               29

SEQ ID NO: 62           moltype = DNA  length = 40
FEATURE                 Location/Qualifiers
misc_feature            1..40
                        note = EMX1 ON read
source                  1..40
                        mol_type = other DNA
                        organism = synthetic construct
SEQUENCE: 62
cctgagtccg agcagaagaa gagaagggct cccatcacat                                   40

SEQ ID NO: 63           moltype = DNA  length = 40
FEATURE                 Location/Qualifiers
misc_feature            1..40
                        note = EMX1 ON read
source                  1..40
```

```
                    mol_type = other DNA
                    organism = synthetic construct
SEQUENCE: 63
cctgagtccg agcagaagaa gaagaagaag aagaagaaga                              40

SEQ ID NO: 64       moltype = DNA   length = 40
FEATURE             Location/Qualifiers
misc_feature        1..40
                    note = EMX1 ON read
source              1..40
                    mol_type = other DNA
                    organism = synthetic construct
SEQUENCE: 64
cctgagtccg agcggaagaa agaagggctc ccatcacatc                              40

SEQ ID NO: 65       moltype = DNA   length = 18
FEATURE             Location/Qualifiers
misc_feature        1..18
                    note = EMX1 ON read
source              1..18
                    mol_type = other DNA
                    organism = synthetic construct
SEQUENCE: 65
cctgctccca tcacatca                                                      18

SEQ ID NO: 66       moltype = DNA   length = 40
FEATURE             Location/Qualifiers
misc_feature        1..40
                    note = EMX1 OT-1 read
source              1..40
                    mol_type = other DNA
                    organism = synthetic construct
SEQUENCE: 66
tcagagttag agcagaagaa gaaaggcatg gagtaaaggc                              40

SEQ ID NO: 67       moltype = DNA   length = 40
FEATURE             Location/Qualifiers
misc_feature        1..40
                    note = EMX1 OT-1 read
source              1..40
                    mol_type = other DNA
                    organism = synthetic construct
SEQUENCE: 67
tcagagttag agcagaagaa agaaaggcat ggagtaaagg                              40

SEQ ID NO: 68       moltype = DNA   length = 37
FEATURE             Location/Qualifiers
misc_feature        1..37
                    note = EMX1 OT-1 read
source              1..37
                    mol_type = other DNA
                    organism = synthetic construct
SEQUENCE: 68
tcagagttag agcagaagaa aggcatggag taaaggc                                 37

SEQ ID NO: 69       moltype = DNA   length = 26
FEATURE             Location/Qualifiers
misc_feature        1..26
                    note = EMX1 OT-1 read
source              1..26
                    mol_type = other DNA
                    organism = synthetic construct
SEQUENCE: 69
tcagagttag agcatggagt aaaggc                                             26

SEQ ID NO: 70       moltype = DNA   length = 34
FEATURE             Location/Qualifiers
misc_feature        1..34
                    note = EMX1 OT-1 read
source              1..34
                    mol_type = other DNA
                    organism = synthetic construct
SEQUENCE: 70
tcagagttag agcagaaagg catggagtaa aggc                                    34

SEQ ID NO: 71       moltype = DNA   length = 27
FEATURE             Location/Qualifiers
misc_feature        1..27
                    note = EMX1 OT-1 read
```

```
source                         1..27
                               mol_type = other DNA
                               organism = synthetic construct
SEQUENCE: 71
tcagagttag agcagaagag taaaggc                                              27

SEQ ID NO: 72                  moltype = DNA   length = 33
FEATURE                        Location/Qualifiers
misc_feature                   1..33
                               note = EMX1 OT-1 read
source                         1..33
                               mol_type = other DNA
                               organism = synthetic construct
SEQUENCE: 72
tcagagttag agcagaaggc atggagtaaa ggc                                       33

SEQ ID NO: 73                  moltype = DNA   length = 31
FEATURE                        Location/Qualifiers
misc_feature                   1..31
                               note = EMX1 OT-1 read
source                         1..31
                               mol_type = other DNA
                               organism = synthetic construct
SEQUENCE: 73
tcagagttag agaaaggcat ggagtaaagg c                                         31

SEQ ID NO: 74                  moltype = DNA   length = 26
FEATURE                        Location/Qualifiers
misc_feature                   1..26
                               note = EMX1 OT-1 read
source                         1..26
                               mol_type = other DNA
                               organism = synthetic construct
SEQUENCE: 74
tcagaagaaa ggcatggagt aaaggc                                               26

SEQ ID NO: 75                  moltype = DNA   length = 35
FEATURE                        Location/Qualifiers
misc_feature                   1..35
                               note = EMX1 OT-1 read
source                         1..35
                               mol_type = other DNA
                               organism = synthetic construct
SEQUENCE: 75
tcagagttag agcagaagaa gcatggagta aaggc                                     35

SEQ ID NO: 76                  moltype = DNA   length = 33
FEATURE                        Location/Qualifiers
misc_feature                   1..33
                               note = EMX1 OT-1 read
source                         1..33
                               mol_type = other DNA
                               organism = synthetic construct
SEQUENCE: 76
tcagagttag agagaaaggc atggagtaaa ggc                                       33

SEQ ID NO: 77                  moltype = DNA   length = 36
FEATURE                        Location/Qualifiers
misc_feature                   1..36
                               note = EMX1 OT-1 read
source                         1..36
                               mol_type = other DNA
                               organism = synthetic construct
SEQUENCE: 77
tcagagttag agcagagaaa ggcatggagt aaaggc                                    36

SEQ ID NO: 78                  moltype = DNA   length = 29
FEATURE                        Location/Qualifiers
misc_feature                   1..29
                               note = EMX1 OT-1 read
source                         1..29
                               mol_type = other DNA
                               organism = synthetic construct
SEQUENCE: 78
tcagagttag aaaggcatgg agtaaaggc                                            29

SEQ ID NO: 79                  moltype = DNA   length = 29
FEATURE                        Location/Qualifiers
misc_feature                   1..29
```

```
                    note = EMX1 OT-1 read
source              1..29
                    mol_type = other DNA
                    organism = synthetic construct
SEQUENCE: 79
tcagagttag agcagaagaa agtaaaggc                                         29

SEQ ID NO: 80       moltype = DNA   length = 40
FEATURE             Location/Qualifiers
misc_feature        1..40
                    note = EMX1 OT-1 read
source              1..40
                    mol_type = other DNA
                    organism = synthetic construct
SEQUENCE: 80
tcagagttag agcagaagaa gaaaggtatg gagtaaaggc                              40

SEQ ID NO: 81       moltype = DNA   length = 37
FEATURE             Location/Qualifiers
misc_feature        1..37
                    note = EMX1 OT-1 read
source              1..37
                    mol_type = other DNA
                    organism = synthetic construct
SEQUENCE: 81
tcagagttag agcatgagaa aggcatggag taaaggc                                 37

SEQ ID NO: 82       moltype = DNA   length = 40
FEATURE             Location/Qualifiers
misc_feature        1..40
                    note = EMX1 OT-1 read
source              1..40
                    mol_type = other DNA
                    organism = synthetic construct
SEQUENCE: 82
tcagagttag agcagaagaa aagaaaggca tggagtaaag                              40

SEQ ID NO: 83       moltype = DNA   length = 40
FEATURE             Location/Qualifiers
misc_feature        1..40
                    note = EMX1 OT-1 read
source              1..40
                    mol_type = other DNA
                    organism = synthetic construct
SEQUENCE: 83
tcagagttag agcagaagaa gaaaggcatg gggtaaaggc                              40

SEQ ID NO: 84       moltype = DNA   length = 40
FEATURE             Location/Qualifiers
misc_feature        1..40
                    note = EMX1 OT-1 read
source              1..40
                    mol_type = other DNA
                    organism = synthetic construct
SEQUENCE: 84
tcagagttag agcagaagaa aaccactacc tgagcaccca                              40

SEQ ID NO: 85       moltype = DNA   length = 40
FEATURE             Location/Qualifiers
misc_feature        1..40
                    note = EMX1 OT-1 read
source              1..40
                    mol_type = other DNA
                    organism = synthetic construct
SEQUENCE: 85
tcagagttag agcagaagaa gaagaaaggc atggagtaaa                              40

SEQ ID NO: 86       moltype = DNA   length = 40
FEATURE             Location/Qualifiers
misc_feature        1..40
                    note = EMX1 OT-1 read
source              1..40
                    mol_type = other DNA
                    organism = synthetic construct
SEQUENCE: 86
tcagagttag agcagaagaa ctgagcaccc agtccgccct                              40

SEQ ID NO: 87       moltype = DNA   length = 33
FEATURE             Location/Qualifiers
```

```
misc_feature               1..33
                           note = EMX1 OT-1 read
source                     1..33
                           mol_type = other DNA
                           organism = synthetic construct
SEQUENCE: 87
tcagagttag agcagaagaa atggagtaaa ggc                                    33

SEQ ID NO: 88              moltype = DNA  length = 40
FEATURE                    Location/Qualifiers
misc_feature               1..40
                           note = EMX1 OT-2 read
source                     1..40
                           mol_type = other DNA
                           organism = synthetic construct
SEQUENCE: 88
caagagtcta agcagaagaa gaagagagcc actacccaac                             40

SEQ ID NO: 89              moltype = DNA  length = 40
FEATURE                    Location/Qualifiers
misc_feature               1..40
                           note = EMX1 OT-2 read
source                     1..40
                           mol_type = other DNA
                           organism = synthetic construct
SEQUENCE: 89
caagagtcta agcagaagaa agaagagagc cactacccaa                             40

SEQ ID NO: 90              moltype = DNA  length = 37
FEATURE                    Location/Qualifiers
misc_feature               1..37
                           note = EMX1 OT-2 read
source                     1..37
                           mol_type = other DNA
                           organism = synthetic construct
SEQUENCE: 90
caagagtcta agcagaagaa gagagccact acccaac                                37

SEQ ID NO: 91              moltype = DNA  length = 39
FEATURE                    Location/Qualifiers
misc_feature               1..39
                           note = EMX1 OT-2 read
source                     1..39
                           mol_type = other DNA
                           organism = synthetic construct
SEQUENCE: 91
caagagtcta agcagaagag aagagagcca ctacccaac                              39

SEQ ID NO: 92              moltype = DNA  length = 40
FEATURE                    Location/Qualifiers
misc_feature               1..40
                           note = EMX1 OT-2 read
source                     1..40
                           mol_type = other DNA
                           organism = synthetic construct
SEQUENCE: 92
caagagccta agcagaagaa gaagagagcc actacccaac                             40

SEQ ID NO: 93              moltype = DNA  length = 40
FEATURE                    Location/Qualifiers
misc_feature               1..40
                           note = EMX1 OT-2 read
source                     1..40
                           mol_type = other DNA
                           organism = synthetic construct
SEQUENCE: 93
caagagtcta agcagaagaa gaggagagcc actacccaac                             40

SEQ ID NO: 94              moltype = DNA  length = 40
FEATURE                    Location/Qualifiers
misc_feature               1..40
                           note = EMX1 OT-2 read
source                     1..40
                           mol_type = other DNA
                           organism = synthetic construct
SEQUENCE: 94
cgagagtcta agcagaagaa gaagagagcc actacccaac                             40

SEQ ID NO: 95              moltype = DNA  length = 40
```

```
                              -continued

FEATURE                 Location/Qualifiers
misc_feature            1..40
                        note = EMX1 OT-2 read
source                  1..40
                        mol_type = other DNA
                        organism = synthetic construct
SEQUENCE: 95
caagggtcta agcagaagaa gaagagagcc actacccaac                          40

SEQ ID NO: 96           moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 96
caagagtcta agcagaagaa ggagagagcc actacccaac                          40

SEQ ID NO: 97           moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 97
caagagtcta agcagaggaa gaagagagcc actacccaac                          40

SEQ ID NO: 98           moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 98
caagagtcta agcaggagaa gaagagagcc actacccaac                          40

SEQ ID NO: 99           moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 99
caagagtcta agcagaagaa gaagagggcc actacccaac                          40

SEQ ID NO: 100          moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 100
caagagtcta agcagaagag gaagagagcc actacccaac                          40

SEQ ID NO: 101          moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 101
caagagtcta agcagaagga gaagagagcc actacccaac                          40

SEQ ID NO: 102          moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 102
caggagtcta agcagaagaa gaagagagcc actacccaac                          40
```

-continued

```
SEQ ID NO: 103          moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 103
caagagtcta agcagaagaa gagggagcc actacccaac                           40

SEQ ID NO: 104          moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 104
caagagtcta ggcagaagaa gagagagcc actacccaac                           40

SEQ ID NO: 105          moltype = DNA   length = 40
FEATURE                 Location/Qualifiers
misc_feature            1..40
                        note = EMX1 OT-2 read
source                  1..40
                        mol_type = other DNA
                        organism = synthetic construct
SEQUENCE: 105
caagagtcta agcggaagaa gagagagcc actacccaac                           40

SEQ ID NO: 106          moltype = DNA   length = 23
FEATURE                 Location/Qualifiers
misc_feature            1..23
                        note = Primer
source                  1..23
                        mol_type = other DNA
                        organism = synthetic construct
SEQUENCE: 106
ccatctcatc cctgcgtgtc tcc                                            23

SEQ ID NO: 107          moltype = DNA   length = 44
FEATURE                 Location/Qualifiers
misc_feature            1..44
                        note = Adaptor Sequence
source                  1..44
                        mol_type = other DNA
                        organism = synthetic construct
SEQUENCE: 107
ccatctcatc cctgcgtgtc tccgactcag ctaaggtaac gatt                     44

SEQ ID NO: 108          moltype = DNA   length = 43
FEATURE                 Location/Qualifiers
misc_feature            1..43
                        note = Adaptor Sequence
source                  1..43
                        mol_type = other DNA
                        organism = synthetic construct
SEQUENCE: 108
atcgttacct tagctgagtc ggagacacgc agggatgaga tgg                      43

SEQ ID NO: 109          moltype = DNA   length = 21
FEATURE                 Location/Qualifiers
misc_feature            1..21
                        note = Adaptor Sequence
source                  1..21
                        mol_type = other DNA
                        organism = synthetic construct
SEQUENCE: 109
atcaccgact gcccatagag a                                              21

SEQ ID NO: 110          moltype = DNA   length = 45
FEATURE                 Location/Qualifiers
misc_feature            1..45
                        note = Adaptor Sequence
source                  1..45
                        mol_type = other DNA
                        organism = synthetic construct
SEQUENCE: 110
aacccactac gcctccgctt tcctctctat gggcagtcgg tgatt                    45
```

```
SEQ ID NO: 111         moltype = DNA  length = 23
FEATURE                Location/Qualifiers
misc_feature           1..23
                       note = Adaptor Sequence
source                 1..23
                       mol_type = other DNA
                       organism = synthetic construct
SEQUENCE: 111
aacccactac gcctccgctt tcc                                              23
```